United States Patent
Brehm et al.

(10) Patent No.: US 11,778,994 B2
(45) Date of Patent: Oct. 10, 2023

(54) NSG MICE LACKING MHC CLASS I AND CLASS II

(71) Applicants: The Jackson Laboratory, Bar Harbor, ME (US); University of Massachusetts, Boston, MA (US)

(72) Inventors: Michael A. Brehm, Dudley, MA (US); Michael V. Wiles, Mount Desert, ME (US); Dale L. Greiner, Hubbardston, MA (US); Leonard D. Shultz, Bar Harbor, ME (US)

(73) Assignees: The Jackson Laboratory, Bar Harbor, ME (US); University of Massachusetts, Boston, MA (US)

( * ) Notice: Subject to any disclaimer, the term of this patent is extended or adjusted under 35 U.S.C. 154(b) by 598 days.

(21) Appl. No.: 16/612,450

(22) PCT Filed: May 14, 2018

(86) PCT No.: PCT/US2018/032548
§ 371 (c)(1),
(2) Date: Nov. 11, 2019

(87) PCT Pub. No.: WO2018/209344
PCT Pub. Date: Nov. 15, 2018

(65) Prior Publication Data
US 2020/0060245 A1    Feb. 27, 2020

Related U.S. Application Data

(60) Provisional application No. 62/649,099, filed on Mar. 28, 2018, provisional application No. 62/505,264, filed on May 12, 2017.

(51) Int. Cl.
*A01K 67/027* (2006.01)

(52) U.S. Cl.
CPC ...... *A01K 67/0276* (2013.01); *A01K 67/0278* (2013.01); *A01K 2207/12* (2013.01); *A01K 2217/075* (2013.01); *A01K 2217/15* (2013.01); *A01K 2227/105* (2013.01); *A01K 2267/03* (2013.01)

(58) Field of Classification Search
None
See application file for complete search history.

(56) References Cited

U.S. PATENT DOCUMENTS

| | | | |
|---|---|---|---|
| 2005/0066375 A1 | 3/2005 | Thiam et al. | |
| 2010/0011450 A1* | 1/2010 | Garcia | C12N 15/8509 800/21 |
| 2019/0110450 A1 | 4/2019 | Serreze et al. | |

FOREIGN PATENT DOCUMENTS

| | | |
|---|---|---|
| CN | 101022824 A | 8/2007 |
| CN | 102971420 A | 3/2013 |
| CN | 103442768 A | 12/2013 |
| CN | 104651299 A | 5/2015 |
| CN | 104812775 A | 7/2015 |
| CN | 104918483 A | 9/2015 |
| EP | 1878342 A1 | 1/2008 |
| JP | 2007-244268 A | 9/2007 |
| JP | 2009-542253 A | 12/2009 |
| WO | WO 92/11753 A1 | 7/1992 |
| WO | WO 2006/007529 A2 | 1/2006 |
| WO | WO 2008/010100 A1 | 1/2008 |

(Continued)

OTHER PUBLICATIONS

King et al Clinical and Experimental Immunology, vol. 157,pp. 104-118) (Year: 2009).*
Ashizawa et al Clinical and Cancer Research, 23, 149-159 (Year: 2016).*
Ashizawa et al Clinical Cancer Research, 23(1), 149-158 (Year: 2017).*
Covassin et al Clin Exp Immunol;166(2):269-80. (Year: 2011).*
Covassin et al Clinical and Experimental Immunology, 174, 372-388 (Year: 2013).*
Grusby et al Science, 253, 1417-1420 (Year: 1991).*
Pino et al Methods in Molecular Biology , 602(Mouse Models for Drug Discovery), 105-117, abstract (Year: 2010).*
Covassin et al (lin Exp Immunol ;166(2):269-80 (Year: 2011).*
Anderson et al., The NOD Mouse: A Model of Immune Dysregulation. Annu Rev Immunol. 2005;23:447-85. doi: 10.1146/annurev.immunol.23.021704.115643.
Brehm et al., Generation of improved humanized mouse models for human infectious diseases. J Immunol Methods. Aug. 2014;410:3-17. doi: 10.1016/j.jim.2014.02.011. Epub Mar. 4, 2014.
Dolatshad et al., A versatile transgenic allele for mouse overexpression studies. Mamm Genome. Dec. 2015;26(11-12):598-608. doi: 10.1007/s00335-015-9602-y. Epub Sep. 14, 2015.

(Continued)

*Primary Examiner* — Anoop K Singh
(74) *Attorney, Agent, or Firm* — Wolf, Greenfield & Sacks, P.C.

(57) ABSTRACT

A NOD.Cg-Prkdc$^{scid}$H2rg$^{tm1}$ $^{Wjl}$/SzJ.(NOD-scid-IL2rγ$^{null}$, NSG) mouse which is genetically modified such that the en NSG mouse lacks functional major histocompatibility complex I (MHC I) and lacks functional major histocompatibility complex II (MHC II) is provided according to aspects of the present, invention. According to specific aspects the genetically modified NSG mouse, is a NOD.Cg-Prkdc$^{scid}$H2-K1$^{tm1\ Bpe}$ H2-Ab1$^{em1\ Mvw}$ H2-D1$^{tm1\ Bpe}$ H2rg$^{tm\ Wjl}$/SzJ (NSG-K$^b$ D$^b$)$^{null}$(IA$^{null}$)) mouse, NSG-RIP-DTR (K$^b$ D$^b$)$^{null}$(IA$^{null}$) mouse, or a NOD.Cg-B2m$^{tm1Une}$PrKdc$^{scid}$H2$^{dlAb1-Ea}$H2rg$^{tm1}$ $^{Wjl}$/SzJ (NSG-B2M$^{null}$(IA IE$^{null}$)) mouse. Human, immune cells and/or human: tumor cells are administered to a genetically modified immunodeficient mouse according to aspects described herein and assays of one or more test substances can be performed using the provided mice.

12 Claims, 24 Drawing Sheets

(56) References Cited

FOREIGN PATENT DOCUMENTS

| WO | WO 2008/124142 A1 | 10/2008 |
|---|---|---|
| WO | WO 2011/130512 A1 | 10/2011 |
| WO | WO 2012/099973 A2 | 7/2012 |
| WO | WO 2014/018625 A1 | 1/2014 |
| WO | WO 2014/071397 A2 | 5/2014 |
| WO | WO 2018/102546 A1 | 6/2018 |

OTHER PUBLICATIONS

Erlich et al., HLA DR-DQ Haplotypes and Genotypes and Type 1 Diabetes Risk: Analysis of the Type 1 Diabetes Genetics Consortium Families. Diabetes. Apr. 2008;57(4):1084-92. doi: 10.2337/db07-1331. Epub Feb. 5, 2008.
Jarchum et al., In Vivo Cytotoxicity of Insulin-Specific CD8+ T-cells in HLA-A*0201 Transgenic NOD mice. Diabetes. Oct. 2007;56(10):2551-60. Epub Jul. 9, 2007.
Johnson et al., Inhibition of Autoimmune Diabetes in Nonobese Diabetic Mice by Transgenic Restoration of H2-E MHC Class II Expression: Additive, but Unequal, Involvement of Multiple APC Subtypes. J Immunol. Aug. 15, 2001;167(4):2404-10.
King, The use of animal models in diabetes research. Br J Pharmacol. Jun. 2012;166(3):877-94. doi: 10.1111/j.1476-5381.2012.01911.x.
Ledford, CRISPR Editing Wreaks Chromosomal Mayhem in Human Embryos. Nature. Jul. 2, 2020;583:17-18.
Lee et al., Unexpected CRISPR on-target effects. Nat Biotechnol. Sep. 2018;36(8):703-704. 2 pages. doi: 10.1038/nbt.4207. Epub Jul. 30, 2018.
Li et al., Identification of autoreactive CD8+ T cell responses targeting chromogranin A in humanized NOD mice and type 1 diabetes patients. Clin Immunol. Jul. 2015;159(1):63-71. doi: 10.1016/j.clim.2015.04.017. Epub May 6, 2015.
Marron et al., Functional evidence for the mediation of diabetogenic T cell responses by HLA-A2.1 MHC class I molecules through transgenic expression in NOD mice. Proc Natl Acad Sci U S A. Oct. 15, 2002;99(21):13753-8. Epub Oct. 2, 2002.
Niens et al, Prevention of "Humanized" Diabetogenic CD8 T-cell Responses in HLA-Transgenic NOD mice by a Multipeptide Coupled-Cell approach. Diabetes. Apr. 2011;60(4):1229-36. doi: 10.2337/db10-1523. Epub Feb. 23, 2011.
Pascolo et al., HLA-A2.1-restricted Education and Cytolytic Activity of CD8(+) T Lymphocytes from $\beta 2$ Microglobulin ($\beta 2$m) HLA-A2.1 Monochain Transgenic H-2D$^b$ $\beta 2$m Double Knockout Mice. J Exp Med. Jun. 16, 1997;185(12):2043-51.
Schaefer et al., Unexpected mutations after CRISPR-Cas9 editing in vivo. Nat Methods. May 30, 2017;14(6):547-548. doi: 10.1038/nmeth.4293. Author Manuscript, pages.
Schloss et al., HLA-B*39:06 Efficiently Mediates Type 1 Diabetes in a Mouse Model Incorporating Reduced Thymic Insulin Expression. J Immunol. May 15, 2018;200(10):3353-3363. doi: 10.4049/jimmunol.1701652. Epub Apr. 9, 2018.
Sellers et al., Immunological Variation Between Inbred Laboratory Mouse Strains: Points to Consider in Phenotyping Genetically Immunomodified Mice. Vet Pathol. Jan. 2012;49(1):32-43. doi: 10.1177/0300985811429314. Epub Nov. 30, 2011.
Serreze et al., "Humanized" HLA Transgenic NOD Mice to Identify Pancreatic $\beta$ Cell Autoantigens of Potential Clinical Relevance to Type 1 Diabetes. Ann N.Y. Acad Sci. Apr. 2007;1103:103-11. Epub Mar. 21, 2007.
Serreze et al., Bridging Mice to Men: Using HLA Transgenic Mice to Enhance the Future Prediction and Prevention of Autoimmune Type 1 Diabetes in Humans. Methods Mol Biol. 2016;1438:137-51. doi: 10.1007/978-1-4939-3661-8_9.
Serreze et al., Loss of Intra-Islet CD20 Expression May Complicate Efficacy of B-Cell-Directed Type 1 Diabetes Therapies. Diabetes. Nov. 2011;60(11):2914-21. 8 pages. doi: 10.2337/db11-0705. Epub Sep. 16, 2011.
Serreze et al., Major Histocompatibility Complex Class I-Deficient NOD-$\beta 2$m$^{null}$ Mice are Diabetes and Insulitis Resistant. Diabetes. Mar. 1994;43(3):505-9.
Shi et al., Germ line deletion of the CD1 locus exacerbates diabetes in the NOD mouse. Proc Natl Acad Sci U S A. Jun. 5, 2001;98(12):6777-82.
Simecek et al., Genetic Analysis of Substrain Divergence in Non-Obese Diabetic (NOD) Mice. G3 (Bethesda). Mar. 3, 2015;5(5):771-5. doi: 10.1534/g3.115.017046.
Takai et al., HLA-A*0201-Restricted T Cells From Humanized NOD Mice Recognize Autoantigens of Potential Clinical Relevance to Type 1 Diabetes. J Immunol. Mar. 1, 2006;176(5):3257-65.
Tong et al., CAR Technology and Its Application in Treatment of Multiple Myeloma. Chinese Journal of Experimental Hematology. Feb. 20, 2016. 279-284.
Wang et al., CD1-restricted NK T cells Protect Nonobese Diabetic Mice from Developing Diabetes. J Exp Med. Aug. 6, 2001;194(3):313-19.
Wang et al., Immune system of mice. Chinese Journal of Immunology. Mar. 20, 2016. 289-298.
International Search Report and Written Opinion dated Sep. 10, 2018 in connection with Application No. PCT/US2018/032548.
International Preliminary Report on Patentability dated Nov. 21, 2019 in connection with Application No. PCT/US2018/032548.
Ashizawa et al., Antitumor Effect of Programmed Death-1 (PD-1) Blockade in Humanized the; NOG-MHC Double Knockout Mouse. Clin Cancer Res. Jan. 1, 2017;23(1):149-158. doi: 10.1158/1078-0432.CCR-16-0122. Epub Jul. 25, 2016.
Bosma et al., The mouse mutation severe combined immune deficiency (scid) is on chromosome 16. Immunogenetics. 1989;29(1):54-7.
Brehm et al., 1-NOD-scid IL2rgnull (NSG) mice deficient in murine MHC Class I and Class II expression support engraftment of functional human T cells in the absence of acute xenogeneic GVHD following injection of PBMC. AACR Annual Meeting. Apr. 18, 2018. https://www.abstractsonline.com/pp8/#!/4562/presentation/3784 [last accessed Feb. 10, 2020]. Abstract only, 1pg.
Cosgrove et al., Mice lacking MHC class II molecules. Cell. Sep. 6, 1991;66(5):1051-66.
Covassin et al., Human immune system development and survival of non-obese diabetic (NOD)-scid IL2r?(null) (NSG) mice engrafted with human thymus and autologous haematopoietic stem cells. Clin Exp Immunol. Dec. 2013;174(3):372-88. doi: 10.1111/cei.12180.
Covassin et al., Human peripheral blood CD4 T cell-engrafted non-obese diabetic-scid IL2r?(null) H2-Ab1 (tm1Gru) Tg (human leucocyte antigen D-related 4) mice: a mouse model of; human allogeneic graft-versus-host disease. Clin Exp Immunol. Nov. 2011;166(2):269-80. doi: 10.1111/j.1365-2249.2011.04462.x.
Dai et al., Stress-impaired transcription factor expression and insulin secretion in transplanted human islets. J Clin Invest. May 2, 2016;126(5):1857-70. doi: 10.1172/JCI83657. Epub Apr. 11, 2016.
Ito et al., NOD/SCID/gamma(c)(null) mouse: an excellent recipient mouse model for engraftment of human cells. Blood. Nov. 1, 2002;100(9):3175-82.
King et al., Human peripheral blood leucocyte non-obese diabetic-severe combined immunodeficiency interleukin-2 receptor gamma chain gene mouse model of xenogeneic graft-versus-host-like disease and the role of host major histocompatibility complex. Clin Exp Immunol. Jul. 2009;157(1):104-18. doi: 10.1111/j.1365-2249.2009.03933.x.
Madsen et al., Mice lacking all conventional MHC class II genes. Proc Natl Acad Sci USA. Aug. 31, 1999;96(18):10338-43.
Pearson et al., Non-obese diabetic-recombination activating gene-1 (NOD-Rag1 null) interleukin (IL)-2 receptor common gamma chain (IL2r gamma null) null mice: a radioresistant model for human lymphohaematopoietic engraftment. Clin Exp Immunol. Nov. 2008;154(2):270-84. doi: 10.1111/j.1365-2249.2008.03753.x. Epub Sep. 8, 2008.
Perarnau et al., Single H2Kb, H2Db and double H2KbDb knockout mice: peripheral CD8+ T cell repertoire and anti-lymphocytic choriomeningitis virus cytolytic responses. Eur J Immunol. Apr. 1999;29(4):1243-52.

(56) References Cited

OTHER PUBLICATIONS

Schultz et al., Human lymphoid and myeloid cell development in NOD/LtSz-scid IL2R gamma null mice engrafted with mobilized human hemopoietic stem cells. J Immunol. May 15, 2005;174(10):6477-89.

Vugmeyster et al., Major histocompatibility complex (MHC) class I KbDb −/− deficient mice possess functional CD8+ T cells and natural killer cells. Proc Natl Acad Sci U S A. Oct. 13, 1998;95(21):12492-7.

Yaguchi et al., Human PBMC-transferred murine MHC class I/II-deficient NOG mice enable long-term evaluation of human immune responses. Cell Mol Immunol. Nov. 2018;15(11):953-962. doi: 10.1038/cmi.2017.106. Epub Nov. 20, 2017.

Yaguchi et al., MHC class I/II deficient NOG mice are useful for analysis of human T/B cell responses for humantumor immunology research. J ImmunoTher Cancer. Nov. 8-10, 2013;1(1):P39. Poster Presentation, 1pg.

Beier et al., Perinatal lethality (ple): a mutation caused by integration of a transgene into distal mouse chromosome 15. Genomics. May 1989;4(4):498-504. doi: 10.1016/0888-7543(89)90272-3.

Dobie et al., Variegated transgene expression in mouse mammary gland is determined by the transgene integration locus. Proc Natl Acad Sci U S A. Jun. 25, 1996;93(13):6659-64. doi: 10.1073/pnas.93.13.6659.

Garrick et al., Repeat-induced gene silencing in mammals. Nat Genet. Jan. 1998;18(1):56-9. doi: 10.1038/ng0198-56.

Hatada et al., The influence of chromosomal location on the expression of two transgenes in mice. J Biol Chem. Jan. 8, 1999;274(2):948-55. doi: 10.1074/jbc.274.2.948.

Palmiter et al., Germ-line transformation of mice. Annu Rev Genet. 1986;20:465-99. doi: 10.1146/annurev.ge.20.120186.002341.

\* cited by examiner

A. Blood

Spleen

A. Survival of mice co-injected with PBMC and tumor

B. Tumor Growth

NSG MICE LACKING MHC CLASS I AND CLASS II

REFERENCE TO RELATED APPLICATIONS

This application claims priority from U.S. Provisional Patent Application Ser. No. 62/505,264, filed May 12, 2017 and 62/649,099, filed Mar. 28, 2018, the entire content of both of which is incorporated herein by reference.

GOVERNMENT SUPPORT

This application is a national stage filing under 35 U.S.C. § 371 of international application number PCT/US2018/032548, filed May 14, 2018, which was published under PCT Article 21(2) in English and claims priority from U.S. Provisional Patent Application Serial Nos. 62/505,264, filed May 12, 2017 and 62/649,099, filed Mar. 28, 2018, the entire content of each of which is incorporated herein by reference.

FIELD OF THE INVENTION

Generally described are mouse models of functional human cells and tissues. According to specific aspects, genetically modified immunodeficient mice are provided that are deficient in MHC class I and MHC class II. According to further specific aspects, genetically modified immunodeficient mice are provided that are deficient in MHC class I and MHC class II and which include 1) engrafted functional human T cells and 2) allogeneic or xenogeneic cells, such as human patient-derived tumor cells.

BACKGROUND OF THE INVENTION

Humanized mice, e.g. immunodeficient mice engrafted with functional human cells and tissues, have been widely used to model human immune cell function in vivo. A major limitation for studying human T cell function in such mouse models has been the rapid development of graft versus host disease (GVHD) that not only shortens the experimental time window, but also confounds the analysis of human T cell function due to the underlying ongoing acute GVHD that eventually kills the mice. These issues have hindered studies of human T cell function.

Some attempts were made to generate humanized mouse models lacking the major histocompatibility complex (MHC) class I or class II. For example, Vugmeyster et al. disclose a mouse model deficient in MHC molecules encoded by the H-2K and H 2D genes ($K^bD^b$ $^{-/-}$ mice) (Vugmeyster et al., Proc. Natl. Acad. Sci. USA 95: 12492-12497, 1998). Ashizawa et al. describe a humanized immunodeficient NOG mouse (NOD/Shi-scid-IL2rγ$^{null}$) [NOD/Shi-Prkdc$^{scid}$-IL2rγ$^{null}$] knockout of the MHC Class I/II (Ashizawa et al., Clin Cancer Res; 23(1), 149-158, 2017).

There is a continuing need for mouse models of functional human cells and tissues.

SUMMARY OF THE INVENTION

A NOD.Cg-Prkdc$^{scid}$ Il2rg$^{tm1Wjl}$/SzJ (NOD-scid-IL2rγ$^{null}$, NSG) mouse which genetically modified such that the NSG mouse lacks functional major histocompatibility complex I (MHC I) and lacks functional major histocompatibility complex II (MHC II) is provided according to aspects of the present invention. According to specific aspects the genetically modified NSG mouse is a NOD.Cg-Prkdc$^{scid}$ H2-K1$^{tm1Bpe}$ H2-Ab1$^{em1Mvw}$ H2-D1$^{tm1Bpe}$ Il2rg$^{tm1Wjl}$/SzJ (NSG-K$^b$ D$^b$)$^{null}$ (IA$^{null}$)) mouse, NSG-RIP-DTR (K$^b$ D$^b$)$^{null}$ (IA$^{null}$) mouse, or a NOD.Cg-B2m$^{tm1Une}$ Prkdc$^{scid}$ H2$^{dlAb1-Ea}$ Il2rg$^{tm1Wjl}$/SzJ (NSG-B2M$^{null}$ IA IE$^{null}$)) mouse.

A NOD.Cg-Prkdc$^{scid}$ Il2rg$^{tm1Wjl}$/SzJ (NOD-scid-IL2rγ$^{null}$, NSG) mouse which genetically modified such that the NSG mouse lacks functional major histocompatibility complex 1 (MHC I) and lacks functional major histocompatibility complex II (MHC II) is provided according to aspects of the present invention which includes human immune cells. According to specific aspects the genetically modified NSG mouse is a NOD.Cg-Prkdc$^{scid}$ H2-K1$^{tm1Bpe}$ H2-Ab1$^{em1Mvw}$ H2-D1$^{tm1Bpe}$ Il2rg$^{tm1Wjl}$/SzJ (NSG-K$^b$ D$^b$)$^{null}$ (IA$^{null}$)) mouse which includes human immune cells, NSG-RIP-DTR (K$^b$ D$^b$)$^{null}$ (IA$^{null}$) mouse which includes human immune cells, or a NOD.Cg-B2m$^{tm1Une}$ Prkdc$^{scid}$ H2$^{dlAb1-Ea}$ Il2rg$^{tm1Wjl}$/SzJ (NSG-B2M$^{null}$ (IA IE$^{null}$)) mouse which includes human immune cells.

A NOD.Cg-Prkdc$^{scid}$ Il2rg$^{tm1Wjl}$/SzJ (NOD-scid-IL2rγ$^{null}$, NSG) mouse which genetically modified such that the NSG mouse lacks functional major histocompatibility complex I (MHC I) and lacks functional major histocompatibility complex II (MHC II) is provided according to aspects of the present invention which includes human peripheral blood mononuclear cells. According to specific aspects the genetically modified NSG mouse is a NOD.Cg-Prkdc$^{scid}$ H2-K1$^{tm1Bpe}$ H2-Ab1$^{em1Mvw}$ H2-D1$^{tm1Bpe}$ Il2rg$^{tm1Wjl}$/SzJ (NSG-K$^b$ D$^b$)$^{null}$ (IA$^{null}$)) mouse which includes human peripheral blood mononuclear cells, NSG-RIP-DTR (K$^b$ D$^b$)$^{null}$ (IA$^{null}$) mouse which includes human peripheral blood mononuclear cells, or a NOD.Cg-B2m$^{tm1Une}$ Prkdc$^{scid}$ H2$^{dlAb1-Ea}$ Il2rg$^{tm1Wjl}$/SzJ (NSG-B2M$^{null}$ (IA IE$^{null}$)) mouse which includes human peripheral blood mononuclear cells.

A NOD.Cg-Prkdc$^{scid}$ Il2rg$^{tm1Wjl}$/SzJ (NOD-scid-IL2rγ$^{null}$, NSG) mouse which genetically modified such that the NSG mouse lacks functional major histocompatibility complex I (MHC I) and lacks functional major histocompatibility complex II (MHC II) is provided according to aspects of the present invention which includes human T cells. According to specific aspects the genetically modified NSG mouse is a NOD.Cg-Prkdc$^{scid}$ H2-K1$^{tm1Bpe}$ H2-Ab1$^{em1Mvw}$ H2-D1$^{tm1Bpe}$ Il2rg$^{tm1Wjl}$/SzJ (NSG-K$^b$ D$^b$)$^{null}$ (IA$^{null}$)) mouse which includes human T cells, NSG-RIP-DTR (K$^b$ D$^b$)$^{null}$ (IA$^{null}$) mouse which includes human T cells, or a NOD.Cg-B2m$^{tm1Une}$ Prkdc$^{scid}$ H2$^{dlAb1-Ea}$ Il2rg$^{tm1Wjl}$/SzJ (NSG-B2M$^{null}$ (IA IE$^{null}$)) mouse which includes human T cells.

A NOD.Cg-Prkdc$^{scid}$ Il2rg$^{tm1Wjl}$/SzJ (NOD-scid-IL2rγ$^{null}$, NSG) mouse which genetically modified such that the NSG mouse lacks functional major histocompatibility complex I (MHC I) and lacks functional major histocompatibility complex II (MHC II) is provided according to aspects of the present invention which includes human immune cells and human tumor cells. According to specific aspects the genetically modified NSG mouse is a NOD.Cg-Prkdc$^{scid}$ H2-K1$^{tm1Bpe}$ H2-Ab1$^{em1Mvw}$ H2-D1$^{tm1Bpe}$ Il2rg$^{tm1Wjl}$/SzJ (NSG-K$^b$ D$^b$)$^{null}$ (IA$^{null}$)) mouse which includes human immune cells and human tumor cells, NSG-RIP-DTR (K$^b$ D$^b$)$^{null}$ (IA$^{null}$) mouse which includes human immune cells and human tumor cells, or a NOD.Cg-B2m$^{tm1Une}$ Prkdc$^{scid}$ H2$^{dlAb1-Ea}$ Il2rg$^{tm1Wjl}$/SzJ (NSG-B2M$^{null}$ (IA IE$^{null}$)) mouse which includes human immune cells and human tumor cells.

A NOD.Cg-Prkdc$^{scid}$ Il2rg$^{tm1Wjl}$/SzJ (NOD-scid-IL2rγ$^{null}$, NSG) mouse which genetically modified such that the NSG mouse lacks functional major histocompatibility complex I (MHC I) and lacks functional major histocompatibility complex II (MHC II) is provided according to aspects of the present invention which includes human peripheral blood mononuclear cells and human tumor cells. According to specific aspects the genetically modified NSG mouse is a NOD.Cg-Prkdc$^{scid}$ H2-K1$^{tm1Bpe}$ H2-Ab1$^{em1Mvw}$ H2-D1$^{tm1Bpe}$ Il2rg$^{tm1Wjl}$/SzJ (NSG-K$^b$ D$^b)^{null}$ (IA$^{null}$)) mouse which includes human peripheral blood mononuclear cells and human tumor cells, NSG-RIP-DTR (K$^b$ D$^b)^{null}$ (IA$^{null}$) mouse which includes human peripheral blood mononuclear cells and human tumor cells, or a NOD.Cg-B2m$^{tm1Une}$ Prkdc$^{scid}$ H2$^{dlAb1-Ea}$ Il2rg$^{tm1Wjl}$/SzJ (NSG-B2M$^{null}$ (IA IE$^{null}$)) mouse which includes human peripheral blood mononuclear cells and human tumor cells.

A NOD.Cg-Prkdc$^{scid}$ Il2rg$^{tm1Wjl}$/SzJ (NOD-scid-IL2rγ$^{null}$, NSG) mouse which genetically modified such that the NSG mouse lacks functional major histocompatibility complex I (MHC I) and lacks functional major histocompatibility complex II (MHC II) is provided according to aspects of the present invention which includes human T cells and human tumor cells. According to specific aspects the genetically modified NSG mouse is a NOD.Cg-Prkdc$^{scid}$ H2-K1$^{tm1Bpe}$ H2-Ab1$^{em1Mvw}$ H2-D1$^{tm1Bpe}$ Il2rg$^{tm1Wjl}$/SzJ (NSG-K$^b$ D$^b)^{null}$ (IA$^{null}$)) mouse which includes human T cells and human tumor cells, NSG-RIP-DTR (K$^b$ D$^b)^{null}$ (IA$^{null}$) mouse which includes human T cells and human tumor cells, or a NOD.Cg-B2m$^{tm1Une}$ Prkdc$^{scid}$ H2$^{dlAb1-Ea}$ Il2rg$^{tm1Wjl}$/SzJ (NSG-B2M$^{null}$(IA IE$^{null}$)) mouse which includes human T cells and human tumor cells.

An NSG-(K$^b$ D$^b)^{null}$ (IA$^{null}$)) mouse of the present invention is characterized by clearance of no more than 60%, such as clearance of no more than 70%, 80%, or 90%, of administered human IgG in a time period of 2 days following administration of the human IgG.

An immunodeficient mouse genetically modified such that the mouse lacks functional major histocompatibility complex I (MHC I) and lacks functional major histocompatibility complex II (MHC II), with the proviso that the immunodeficient mouse is not a NOD/Shi-scid-IL2rγ$^{null}$ mouse characterized by β2m (component of MHC I) knockout and IAβ (light chain of MHC II) knockout. According to particular aspects, the mouse further includes human immune cells such as human peripheral blood mononuclear cells and such as human T cells. According to particular aspects, the mouse further includes human immune cells such as human peripheral blood mononuclear cells and such as human T cells and further includes human tumor cells.

A method for modeling an effect of a human immune system, or one or more components thereof, in a genetically modified immunodeficient mouse is provided which includes administering a test substance to genetically modified immunodeficient mouse of the present invention; and assaying the effect of the human immune system, or one or more components thereof, in the genetically modified immunodeficient mouse. The test substance can be, but is not limited to an anti-tumor antibody, an immunotherapeutic agent, an immune checkpoint inhibitor, including, but not limited to, a PD-1 inhibitor, PD-L1 inhibitor, or a CTLA-4 inhibitor. The test substance can be an immune checkpoint inhibitor selected from atezolizumab, avelumab, durvalumab, ipilimumab, nivolumab, or pembrolizumab, or an antigen-binding fragment of any one of the foregoing. The test substance can be an anti-cancer agent.

A method for modeling an effect of human T cells in a genetically modified immunodeficient mouse is provided which includes administering a test substance to genetically modified immunodeficient mouse of the present invention; and assaying the effect of the human T cells in the genetically modified immunodeficient mouse. The test substance can be, but is not limited to an anti-tumor antibody, an immunotherapeutic agent, an immune checkpoint inhibitor, including, but not limited to, a PD-1 inhibitor, PD-L1 inhibitor, or a CTLA-4 inhibitor. The test substance can be an immune checkpoint inhibitor selected from atezolizumab, avelumab, durvalumab, ipilimumab, nivolumab, or pembrolizumab, or an antigen-binding fragment of any one of the foregoing. The test substance can be an anti-cancer agent.

A method for modeling an effect of a human immune system, or one or more components thereof, in a genetically modified immunodeficient mouse is provided wherein the genetically modified immunodeficient mouse is a NOD.Cg-Prkdc$^{scid}$ H2-K1$^{tm1Bpe}$ H2-Ab1$^{em1Mvw}$ H2-D1$^{tm1Bpe}$ Il2rg$^{tm1Wjl}$/SzJ (NSG-K$^b$ D$^b)^{null}$ (IA$^{null}$)) mouse, NSG-RIP-DTR (K$^b$ D$^b)^{null}$ (IA$^{null}$) mouse, or a NOD.Cg-B2m$^{tm1Une}$ Prkdc$^{scid}$ H2$^{dlAb1-Ea}$ Il2rg$^{tm1Wjl}$/SzJ (NSG-B2M$^{null}$ (IA IE$^{null}$)) mouse, wherein the method includes administering a test substance to the genetically modified immunodeficient mouse; and assaying the effect of the human immune system, or one or more components thereof, in the genetically modified immunodeficient mouse. The test substance can be, but is not limited to an anti-tumor antibody, an immunotherapeutic agent, an immune checkpoint inhibitor, including, but not limited to, a PD-1 inhibitor, PD-L1 inhibitor, or a CTLA-4 inhibitor. The test substance can be an immune checkpoint inhibitor selected from atezolizumab, avelumab, durvalumab, ipilimumab, nivolumab, or pembrolizumab, or an antigen-binding fragment of any one of the foregoing. The test substance can be an anti cancer agent.

A method for modeling an effect of human leukocytes in a genetically modified immunodeficient mouse is provided wherein the genetically modified immunodeficient mouse is a NOD.Cg-Prkdc$^{scid}$ H2-K1$^{tm1Bpe}$ H2-Ab1$^{em1Mvw}$ H2-D1$^{tm1Bpe}$ Il2rg$^{tm1Wjl}$/SzJ (NSG-K$^b$ D$^b)^{null}$ (IA$^{null}$)) mouse, NSG-RIP-DTR (K$^b$ D$^b)^{null}$ (IA$^{null}$) mouse, or a NOD.Cg-B2m$^{tm1Une}$ Prkdc$^{scid}$ H2$^{dlAb1-Ea}$ Il2rg$^{tm1Wjl}$/SzJ (NSG-B2M$^{null}$ (IA IE$^{null}$)) mouse, wherein the method includes administering a test substance to the genetically modified immunodeficient mouse; and assaying the effect of the human leukocytes in the genetically modified immunodeficient mouse. The test substance can be, but is not limited to an anti-tumor antibody, an immunotherapeutic agent, an immune checkpoint inhibitor, including, but not limited to, a PD-1 inhibitor, PD-L1 inhibitor, or a CTLA-4 inhibitor. The test substance can be an immune checkpoint inhibitor selected from atezolizumab, avelumab, durvalumab, ipilimumab, nivolumab, or pembrolizumab, or an antigen-binding fragment of any one of the foregoing. The test substance can be an anti-cancer agent.

A method for modeling an effect of human PMBC in a genetically modified immunodeficient mouse is provided wherein the genetically modified immunodeficient mouse is a NOD.Cg-Prkdc$^{scid}$ H2-K1$^{tm1Bpe}$ H2-Ab1$^{em1Mvw}$ H2-D1$^{tm1Bpe}$ Il2rg$^{tm1Wjl}$/SzJ (NSG-K$^b$ D$^b)^{null}$ (IA$^{null}$)) mouse, NSG-RIP-DTR (K$^b$ D$^b)^{null}$ (IA$^{null}$) mouse, or a NOD.Cg-B2m$^{tm1Une}$ Prkdc$^{scid}$ H2$^{dlAb1-Ea}$ Il2rg$^{tm1Wjl}$/SzJ (NSG-B2M$^{null}$ (IA IE$^{null}$)) mouse, wherein the method includes administering a test substance to the genetically modified immunodeficient mouse; and assaying the effect of the human PMBC in the genetically modified immunodeficient mouse. The test substance can be, but is not limited to an anti-tumor antibody, an immunotherapeutic agent, an immune checkpoint inhibitor, including, but not limited to, a PD-1 inhibitor, PD-L1 inhibitor, or a CTLA-4 inhibitor. The test substance can be an immune checkpoint inhibitor selected from atezolizumab, avelumab, durvalumab, ipilimumab, nivolumab, or pembrolizumab, or an antigen-binding fragment of any one of the foregoing. The test substance can be an anti-cancer agent.

A method for modeling an effect of a human T cell in a genetically modified immunodeficient mouse is provided wherein the genetically modified immunodeficient mouse is a NOD.Cg-Prkdc$^{scid}$ H2-K1$^{tm1Bpe}$ H2-Ab1$^{em1Mvw}$ H2-D1$^{tm1Bpe}$ Il2rg$^{tm1Wjl}$/SzJ (NSG-K$^b$ D$^b)^{null}$ (IA$^{null}$)) mouse, NSG-RIP-DTR (K$^b$ D$^b)^{null}$ (IA$^{null}$) mouse, or a NOD.Cg-B2m$^{tm1Une}$ Prkdc$^{scid}$ H2$^{dlAb1-Ea}$ Il2rg$^{tm1Wjl}$/SzJ (NSG-B2M$^{null}$ (IA IE$^{null}$)) mouse, wherein the method includes administering a test substance to the genetically modified immunodeficient mouse; and assaying the effect of the human T cell in the genetically modified immunodeficient mouse. The test substance can be, but is not limited to an anti-tumor antibody, an immunotherapeutic agent, an immune checkpoint inhibitor, including, but not limited to, a PD-1 inhibitor, PD-L1 inhibitor, or a CTLA-4 inhibitor. The test substance can be an immune checkpoint inhibitor selected from atezolizumab, avelumab, durvalumab, ipilimumab, nivolumab, or pembrolizumab, or an antigen-binding fragment of any one of the foregoing. The test substance can be an anti-cancer agent.

BRIEF DESCRIPTION OF THE DRAWINGS

FIG. 1A is a graph showing that monocyte derived dendritic cells were identified in viable cells as CD11b+, Ly6Gdim, CD11c+ and Ly6C−.

FIG. 1B is a graph showing results of evaluation of monocyte derived dendritic cells recovered from each strain for expression of mouse H2K$^d$ and H2K$^b$. Representative staining is shown for all stains (N=2).

FIG. 1C is a graph showing results of evaluation of monocyte derived dendritic cells recovered from each strain for expression of mouse H2 IA$^{g7}$ and H2 IA$^b$. Representative staining is shown for all stains (N=2).

FIG. 3A is a graph showing % survival when NSG, NSG-(IA$^{null}$), NSG-(K$^b$ D$^b)^{null}$, and NSG-(K$^b$ D$^b)^{null}$ (IA$^{null}$) mice were used as recipients of PBMC. The data are representative of 3 independent experiments. Survival distributions between groups were tested using the log rank statistic.

FIG. 3B is a graph showing % survival when NSG, NSG-(IA IE)$^{null}$, NSG-B2M$^{null}$, and NSG-B2M$^{null}$(IA IE)$^{null}$ mice were used as recipients of PBMC. The data are representative of 3 independent experiments. Survival distributions between groups were tested using the log rank statistic.

FIG. 4A is a graph showing human cell chimerism levels as monitored in the blood of NSG, NSG-(IA$^{null}$), NSG-(K$^b$ D$^b)^{null}$, and NSG-(K$^b$ D$^b)^{null}$ (IA$^{null}$) mice injected with PBMC over a 10 week time period. The data are representative of 3 independent experiments. A 2-way ANOVA was used to determine significant differences between groups at each time point. Week 6; NSG vs NSG-(K$^b$ D$^b)^{null}$ p<0.01 and NSG vs NSG-(K$^b$ D$^b)^{null}$ (IA$^{null}$) p<0.001; NSG-(IA$^{null}$) vs NSG-(K$^b$ D$^b)^{null}$ p<0.01, and NSG-(IA$^{null}$) vs NSG-(K$^b$ D$^b)^{null}$ (IA$^{null}$) p<0.001.

FIG. 4B is a graph showing human cell chimerism levels as monitored in the spleens of NSG, NSG-(IA$^{null}$), NSG-(K$^b$ D$^b)^{null}$, and NSG-(K$^b$ D$^b)^{null}$ (IA$^{null}$) mice injected with PBMC when mice were euthanized. A one-way ANOVA was used to determine significant differences between groups. * represents p<0.05, ** represents p<0.01.

FIG. 4C is a graph showing human cell chimerism levels as monitored in the blood of NSG, NSG-(IA IE)$^{null}$, NSG-B2M$^{null}$, and NSG-B2M$^{null}$ (IA IE)$^{null}$ mice injected with PBMC over a 10 week time period. The data are representative of 3 independent experiments. A 2-way ANOVA was used to determine significant differences between groups at each time point. Week 4; NSG vs NSG-B2M$^{null}$ (IA IE)$^{null}$ p<0.01, NSG-(IA IE)$^{null}$ vs NSG-B2M$^{null}$ (IA IE)$^{null}$ p<0.01, and NSG-B2M$^{null}$ vs NSG-B2M$^{null}$ (IA IE)$^{null}$ p<0.05. Week 6; NSG vs NSG-B2M$^{null}$ (IA IE)$^{null}$ p<0.05, NSG-(IA IE)$^{null}$ vs NSG-B2M$^{null}$ p<0.05, NSG-(IA IE)$^{null}$ vs NSG-B2M$^{null}$ (IA IE)$^{null}$ p<0.01. Week 8; NSG vs NSG-B2M$^{null}$ p<0.001, NSG vs NSG-B2M$^{null}$ (IA IE)$^{null}$ p<0.01, NSG-(IA IE)$^{null}$ vs NSG-B2M$^{null}$ p<0.001, NSG-(IA IE)$^{null}$ vs NSG-B2M$^{null}$ (IA IE)$^{null}$ p<0.01. Week 10; NSG vs NSG-B2M$^{null}$ p<0.01, NSG vs NSG-B2M$^{null}$ (IA IE)$^{null}$ p<0.01, and NSG-(IA IE)$^{null}$ vs NSG-B2M$^{null}$ p<0.01, NSG-(IA IE)$^{null}$ vs NSG-B2M$^{null}$ (IA IE)$^{null}$ p<0.01.

FIG. 4D is a graph showing human cell chimerism levels as monitored in the spleens of NSG, NSG-(IA IE)$^{null}$, NSG B2M$^{null}$, and NSG B2M$^{null}$ (IA IE)$^{null}$ mice injected with PBMC when mice were euthanized. A one-way ANOVA was used to determine significant differences between groups. ** represents p<0.01.

FIG. 5A is a graph showing human CD3+ cells (% of CD45) when NSG (N=7), NSG-(IA$^{null}$) (N=5), NSG-(K$^b$ D$^b)^{null}$ (N=7), and NSG-(K$^b$ D$^b)^{null}$ (IA$^{null}$) (N=8) mice were used as recipients of PBMC. The data are representative of 3 independent experiments. A 2-way ANOVA was used to determine significant differences between groups at each time point. * represents p<0.05.

FIG. 5B is a graph showing human CD20+ cells (% of CD45) when NSG (N=7), NSG-(IA$^{null}$) (N=5), NSG-(K$^b$ D$^b)^{null}$ (N=7), and NSG-(K$^b$ D$^b)^{null}$ (IA$^{null}$) (N=8) mice were used as recipients of PBMC. The data are representative of 3 independent experiments. A 2-way ANOVA was used to determine significant differences between groups at each time point. * represents p<0.05.

FIG. 5C is a graph showing human CD3+ cells (% of CD45) when NSG (N=6), NSG-(IA IE)$^{null}$ (N=6), NSG-B2M$^{null}$ (N=5), and NSG-B2M$^{null}$ (IA IE)$^{null}$ (N=7) mice were used as recipients of PBMC. The data are representative of 3 independent experiments. A 2-way ANOVA was used to determine significant differences between groups at each time point. * represents p<0.05.

FIG. 5D is a graph showing human CD20+ cells (% of CD45) when NSG (N=6), NSG-(IA IE)$^{null}$ (N=6), NSG-B2M$^{null}$ (N=5), and NSG-B2M$^{null}$ (IA IE)$^{null}$ (N=7) mice were used as recipients of PBMC. The data are representative of 3 independent experiments. A 2-way ANOVA was used to determine significant differences between groups at each time point. * represents p<0.05.

FIG. 6A is a graph showing levels of CD4 and CD8 T cells determined by flow cytometry and expressed as a ratio of CD4 to CD8 T cells.

FIG. 6B is a graph showing PD-1 expression by CD4 T cells determined by flow cytometry for NSG, NSG-(IA$^{null}$), NSG-(K$^b$ D$^b$)$^{null}$, and NSG-(K$^b$ D$^b$)$^{null}$ (IA$^{null}$) mice injected with PBMC.

FIG. 6C is a graph showing PD-1 expression by CD8 T cells determined by flow cytometry for NSG, NSG-(IA$^{null}$), NSG-(K$^b$ D$^b$)$^{null}$, and NSG-(K$^b$ D$^b$)$^{null}$ (IA$^{null}$) mice injected with PBMC.

FIGS. 6D-6F are graphs showing representative CD4, CD8, and PD1 staining.

FIGS. 6G and 6H are graphs showing CD4 and CD8 T cells, respectively, that were evaluated for expression of CD45RA and CCR7 by flow cytometry. Percentages of T cell subsets are shown with CD45RA+/CCR7+ cells labeled as naïve, CD45RA-/CCR7+ cells labeled as central memory, CD45RA-/CCR7- cells labeled as effector/effector memory, and CD45RA+/CCR7- cells labeled as TEMRA.

FIG. 7A is a graph showing levels of CD4 and CD8 T cells as determined by flow cytometry and expressed as a ratio of CD4 to CD8 T cells.

FIG. 7B is a graph showing PD-1 expression by CD4 cells as determined by flow cytometry for NSG, NSG-(IA IE)$^{null}$, NSG-B2M$^{null}$, and NSG-B2M (IA IE)$^{null}$ mice injected with PBMC.

FIG. 7C is a graph showing PD-1 expression by CD8 cells as determined by flow cytometry for NSG, NSG-(IA IE)$^{null}$, NSG-B2M$^{null}$, and NSG-B2M$^{null}$ (IA IE)$^{null}$ mice injected with PBMC.

FIGS. 7D-7F are graphs showing representative CD4, CD8, and PD1 staining.

FIGS. 7G and 7H are graphs showing CD4 and CD8 T cells, respectively, that were evaluated for expression of CD45RA and CCR7 by flow cytometry. Percentages of T cell subsets are shown with CD45RA+/CCR7+ cells labeled as naïve, CD45RA-/CCR7+ cells labeled as central memory, CD45RA-/CCR7- cells labeled as effector/effector memory, and CD45RA+/CCR7- cells labeled as TEMRA.

FIG. 8A is a graph showing results of treatment of NSG-RIP-DTR (K$^b$D$^b$)$^{null}$ (IA$^{null}$) mice with 40 ng of diphtheria toxin (DT) 6 days prior to PBMC injection, and then implanted with human islets (4000 IEQ) by intrasplenic injection. On day 0, one group of mice was injected IP with 50×10$^6$ human PBMC, and one group was untreated. Blood glucose levels were monitored, and mice with blood glucose levels over 300 mg/dl for 2 consecutive tests were considered diabetic.

FIG. 8B is a graph showing results of monitoring mice for levels of human cell chimerism by determining the proportion of CD45+ cells in the peripheral blood over 6 weeks and spleen at 7 weeks.

FIGS. 8C and 8D are graphs showing levels of CD3+/CD4+ and CD3+/CD8+ T cells in peripheral blood and spleen, respectively;

FIG. 8E is a graph showing levels of circulating human C-peptide in plasma as determined by ELISA at week 6.

FIG. 8F is a graph showing total insulin content from spleens of islet engrafted mice as determined at week 7 by ELISA.

FIGS. 9A-9C are graphs showing levels of human CD45+ cells (FIG. 9A), CD3+ T cells (FIG. 9B) and CD4+/CD25+/CD127-/FOXP3+ Treg (FIG. 9C) as determined by flow cytometry. A 2-way ANOVA was used to determine significant differences between groups. * represents p<0.005, and ** represents p<0.001.

FIG. 9D shows representative staining of CD4+ T cells for CD25, CD127 and FOXP3 for the indicated groups.

FIG. 9E is a graph showing % survival of recipient mice was monitored, and survival distributions between the indicated groups was tested using the log rank statistic.

FIG. 9F is a graph showing levels of CD4 and CD8 T cell determined by flow cytometry and expressed as a ratio of CD4 to CD8 T cells. Closed black triangles represent NSG mice, open black triangles represent NSG mice injected with AAV-IL2, closed circles represent NSG-$(K^b D^b)^{null}$ $(IA^{null})$ mice and open circles represent NSG-$(K^b D^b)^{null}$ $(IA^{null})$ mice injected with AAV-IL2.

FIG. 9G is a graph showing results of evaluation of CD8 T cells for expression of CD45RA and CCR7 by flow cytometry. Percentages of T cell subsets are shown with CD4SRA+/CCR7+ cells labeled as naïve, CD45RA−/CCR7+ cells labeled as central memory, CD45RA−/CCR7− cells labeled as effector/effector memory, and CD45RA+/CCR7− cells labeled as TEMRA. Closed black triangles represent NSG mice, open black triangles represent NSG mice injected with AAV-IL2, closed circles represent NSG-$(K^b D^b)^{null}$ $(IA^{null})$ mice and open circles represent NSG-$(K^b D^b)^{null}$ $(IA^{null})$ mice injected with AAV-IL2.

FIG. 9H is a graph showing Granzyme B expression by CD8 T cells as determined by flow cytometry and representative staining is shown. A t-test was used to determine significant differences between mice treated with AAV-IL2 and controls. * represents p<0.005, ** represents p<0.001. The data are representative of 3 independent experiments.

DETAILED DESCRIPTION OF THE INVENTION

Figure 1A:
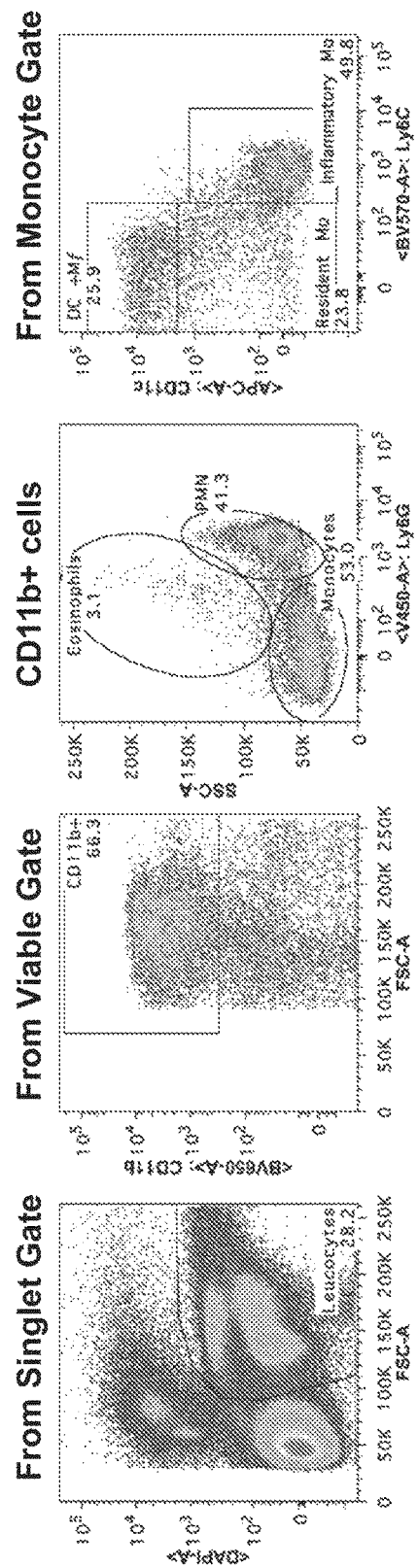
FIGS. 1A-1C show representative flow cytometry of MHC class I and class II expression in NSG-(K$^b$ D$^b)^{null}$ (IA$^{null}$) and NSG-B2M$^{null}$ (IA IE)$^{null}$ mice. Spleens from NSG, NSG-(K$^b$ D$^b)^{null}$ (IA$^{null}$) and NSG-B2M$^{null}$ (IA IE)$^{null}$ knockout mice were disaggregated by enzymatic and mechanical digestion.

Scientific and technical terms used herein are intended to have the meanings commonly understood by those of ordinary skill in the art. Such terms are found defined and used in context in various standard references illustratively including J. Sambrook and D. W. Russell, Molecular Cloning: A Laboratory Manual, Cold Spring Harbor Laboratory Press; 3rd Ed., 2001; F. M. Ausubel, Ed., Short Protocols in Molecular Biology, Current Protocols; 5th Ed., 2002; B. Alberts et al., Molecular Biology of the Cell, 4th Ed., Garland, 2002; D. L. Nelson and M. M. Cox, Lehninger Principles of Biochemistry, 4th Ed., W.H. Freeman & Company, 2004; A. Nagy, M. Gertsenstein, K. Vintersten, R. Behringer, Manipulating the Mouse Embryo: A Laboratory Manual, 3rd edition, Cold Spring Harbor Laboratory Press; Dec. 15, 2002, ISBN-10: 0879695919; Kursad Turksen (Ed.), Embryonic stem cells: methods and protocols in Methods Mol Biol. 2002; 185, Humana Press; Current Protocols in Stem Cell Biology, ISBN; 9780470151808; Chu, E. and Devita, V. T., Eds., Physicians' Cancer Chemotherapy Drug Manual, Jones & Bartlett Publishers, 2005; J. M. Kirkwood et al., Eds., Current Cancer Therapeutics, 4th Ed., Current Medicine Group, 2001; Remington: The Science and Practice of Pharmacy, Lippincott Williams & Wilkins, 21st Ed., 2005; L. V. Allen, Jr. et al., Ansel's Pharmaceutical Dosage Forms and Drug Delivery Systems, 8th Ed., Philadelphia, Pa.: Lippincott, Williams & Wilkins, 2004; and L. Brunton et al., Goodman & Gilman's The Pharmacological Basis of Therapeutics, McGraw-Hill Professional, 12th Ed., 2011.

The singular terms "a," "an," and "the" are not intended to be limiting and include plural referents unless explicitly stated otherwise or the context clearly indicates otherwise.

The term "functional" as used generally herein refers to a protein, complex, cell, or other substance that retains the biological function of the corresponding native protein, complex, cell, or other substance By contrast, the term "non-functional" as used generally herein refers to a protein, complex, cell, or other substance that does not retain the biological function of the corresponding native protein, complex, cell, or other substance.

Genetically modified immunodeficient mice that are deficient in MHC class 1 and MHC class II are provided by the present invention.

According to aspects, a genetically modified immunodeficient mouse is provided which includes in its genome at least one mutation effective to reduce or eliminate expression of functional MHC I α protein and/or reduce or eliminate expression of functional β2-microglobulin such that MHC I is not present or is non functional in the mouse; and which includes in its genome at least one mutation effective to reduce or eliminate expression of functional MHC II α protein and/or expression of functional MHC II β protein such that MHC II is not present or is non-functional in the mouse.

According to aspects, the genetically modified immunodeficient mouse is a genetically modified NSG mouse. NSG MHC I/II knockout mice according to aspects of the present invention are useful in various applications, including study of human immunity in the absence of GVHD and evaluation of antibody-based therapeutics.

MHC I

The terms "MHC I" and "MHC class I" are used interchangeably to refer to a complex formed by MHC I α protein and β2-microglobulin protein.

MHC I α protein includes an extracellular domain (which has three subdomains: α1, α2, and α3), a transmembrane domain, and a cytoplasmic tail. The α1 and α2 subdomains form the peptide-binding cleft, while the α3 subdomain interacts with β2-microglobulin. The terms "H2-K", "H2-D" and "H2-L", refer to mouse MHC I α protein subclasses, all of which are encoded on mouse Chromosome 17.

β2-microglobulin associates noncovalently with the α3 subdomain of MHC I α protein. The gene encoding mouse β2-microglobulin is encoded on Chromosome 2 (Chr2: 122147686-122153083 bp, + strand, GRCm38).

MHC II

The terms "MHC II" and "MHC class II" are used interchangeably to refer to a complex formed by two noncovalently associated proteins: an MHC II α protein and an MHC II β protein. The terms "H-2A" and "H-2E" (often abbreviated as I-A and I-E, respectively) refer to subclasses of MHC II. The MHC II α protein and MHC II β proteins span the plasma membrane and each contains an extracellular domain, a transmembrane domain, and a cytoplasmic domain. The extracellular portion of the MHC II α protein includes MHC II α1 and MHC II α2 domains, and the extracellular portion of the MHC II β protein includes MHC II β1 and MHC II β2 domains.

The term "functional" as used herein in reference to a functional MHC I α protein, a functional β2-microglobulin protein, a functional MHC II α protein, a functional MHC II β protein, functional MHC I or functional MHC II, refers to MHC I α protein, β2-microglobulin protein, MHC II α protein, MHC II β protein, MHC I or MHC II that retains the biological function of the corresponding native MHC I α protein, β2-microglobulin protein, MHC II α protein, MHC II β protein, MHC I or MHC II.

By contrast, the term "non-functional" as used herein in reference to a non functional MHC I α protein, β2-microglobulin protein, MHC II α protein, MHC II β protein, MHC I or MHC II, refers to an MHC protein or MHC complex that does not retain the biological function of the corresponding native MHC I α protein, β2-microglobulin protein, MHC II α protein, MHC II β protein, MHC I or MHC II.

The term "native" as used herein refers to an unmutated protein or nucleic acid.

As used herein, the term "genetically modified" refers to modification of genomic DNA in a mouse that disrupts expression of at least one of: functional MHC I α protein, and functional β2-microglobulin; and at least one of: functional MHC II α protein and functional MHC II β protein such that the mouse that lacks functional MHC I and functional MHC II.

The term "expression" refers to transcription of a nucleic acid sequence to produce a corresponding mRNA and/or translation of the mRNA to produce the corresponding protein.

As used herein, the term "target gene" refers to a nucleic acid sequence that defines a mouse MHC I α gene, mouse β2-microglobulin gene, mouse MHC II α gene or mouse MHC II β gene.

Any of various methods can be used to produce a genetically modified immunodeficient mouse whose genome includes a genetic modification that disrupts expression of at least one of: functional MHC I α protein, and functional β2-microglobulin; and at least one of: functional MHC II α protein and functional MHC II β protein such that the mouse that lacks functional MHC I and functional MHC II.

Genetic modifications are produced using standard methods of genetic engineering such as, but not limited to, chemical mutagenesis, irradiation, homologous recombination and transgenic expression of antisense RNA. Such techniques are well-known in the art and further include, but are not limited to, pronuclear microinjection and transformation of embryonic stem cells. Methods for generating genetically modified animals whose genome includes a gene mutation that can be used include, but are not limited to, those described in J. P. Sundberg and T. Ichiki, Eds., Genetically Engineered Mice Handbook, CRC Press; 2006; M. H. Hofker and J. van Deursen, Eds., Transgenic Mouse Methods and Protocols, Humana Press, 2002; A. L. Joyner, Gene Targeting: A Practical Approach, Oxford University Press, 2000; Manipulating the Mouse Embryo: A Laboratory Manual, 3rd edition, Cold Spring Harbor Laboratory Press; Dec. 15, 2002, ISBN-10: 0879695919; Kursad Turksen (Ed.), Embryonic stem cells: methods and protocols in Methods Mol Biol. 2002; 185, Humana Press; Current Protocols in Stem Cell Biology, ISBN: 978047015180; Meyer et al. PNAS USA, vol. 107 (34), 15022-15026.

According to preferred aspects, in addition to the lack of functional endogenous MHC I and MHC II, no non-endogenous MHC I or MHC II is expressed in a genetically modified immunodeficient mouse of the present invention. In particular, no human lymphocyte compatibility genes are present or expressed in a genetically modified immunodeficient mouse of the present invention according to preferred embodiments.

"Endogenous," as used herein in relation to genes and the proteins they encode, refers to genes present in the genome of the mouse at their native gene locus.

Homology-based recombination gene modification strategies can be used to genetically modify an immunodeficient mouse by "knock-out" or other mutation of a gene encoding an endogenous protein or proteins e.g., at least one of: MHC I α protein, and β2-microglobulin; and at least one of: MHC II α protein and MHC II β protein.

Homology-based recombination gene modification strategies include gene editing approaches such as those using homing endonucleases, integrases, meganucleases, transposons, nuclease-mediated processes using a zinc finger nuclease (ZFN), a Transcription Activator-Like (TAL), a Clustered Regularly Interspaced Short Palindromic Repeats (CRISPR)-Cas, or a Drosophila Recombination-Associated Protein (DRAP) approach. See, for example, Cerbini et al., PLoS One. 2015; 10(1): e0116032; Shen et al., PLoS ONE 8(10): e77696; and Wang et al., Protein & Cell, February 2016, Volume 7, Issue 2, pp 152-156.

Genomic editing is performed, for example, by methods described herein, and as detailed in J. P. Sundberg and T. Ichiki, Eds., Genetically Engineered Mice Handbook, CRC Press; 2006; M. H. Hofker and J. van Deursen, Eds., Transgenic Mouse Methods and Protocols, Humana Press, 2002; A. L. Joyner, Gene Targeting: A Practical Approach, Oxford University Press, 2000; Manipulating the Mouse Embryo: A Laboratory Manual, 3rd edition, Cold Spring Harbor Laboratory Press; Dec. 15, 2002, ISBN-10: 0879695919; Kursad Turksen (Ed.), Embryonic stem cells: methods and protocols in Methods Mol. Biol. 2002; 185, Humana Press; Current Protocols in Stem Cell Biology, ISBN: 978047015180; Meyer et al., PNAS USA, 2010, vol. 107 (34), 15022-15026; and Doudna, J. et al. (eds.) CRISPR-Cas: A Laboratory Manual, 2016, CSHP. A brief description of several genomic editing techniques is described herein.

Nuclease Techniques for Genetic Modification

A genetic modification method, such as but not limited to, a nuclease genetic editing technique, can be used to introduce a desired DNA sequence into the genome at a predetermined target site, such as methods using a homing endonuclease, integrase, meganuclease, transposon, nuclease-mediated process using a zinc finger nuclease (ZFN), a Transcription Activator-Like (TAL), a Clustered Regularly Interspaced Short Palindromic Repeats (CRISPR)-Cas, or Drosophila Recombination-Associated Protein (DRAP). Briefly, a genetic modification method that can be used includes introducing into an ES cell, iPS cell, somatic cell, fertilized oocyte or embryo, RNA molecules encoding a targeted TALEN, ZFN, CRISPR or DRAP and at least one oligonucleotide, then selecting for an ES cell, iPS cell, somatic cell, fertilized oocyte or embryo with the desired genetic modification.

For example, a desired nucleic acid sequence can be introduced into the genome of a mouse at a predetermined target site by a nuclease technique, such as, but not limited to, CRISPR methodology, TAL (transcription activator-like Effector methodology, Zinc Finger-Mediated Genome Editing or DRAP to produce a genetically modified mouse provided according to embodiments of the present invention.

As used herein, the terms "target site" and "target sequence" in the context of a nuclease genetic editing technique refer to a nucleic acid sequence that defines a portion of a chromosomal sequence to be edited and to which a nuclease is engineered to recognize and bind, provided sufficient conditions for binding exist.

CRISPR-Cas System

CRISPRs (Clustered Regularly Interspaced Short Palindromic Repeats) are loci containing multiple short direct repeats that are found in the genomes of approximately 40% of sequenced bacteria and 90% of sequenced archaea and confer resistance to foreign DNA elements, see Horvath, 2010, Science, 327: 167-170; Barrangou et al., 2007, Science, 315: 1709-1712; and Makarova et al, 2011, Nature Reviews Microbiology. 9: 467-477.

CRISPR repeats range in size from 24 to 48 base pairs. They usually show some dyad symmetry, implying the formation of a secondary structure such as a hairpin, but are not truly palindromic. CRISPR repeats are separated by spacers of similar length.

The CRISPR-associated (cas) genes are often associated with CRISPR repeat-spacer arrays. More than forty different Cas protein families have been described (Haft et al. 2005, PLoS Comput Biol. 1 (6): e60). Particular combinations of cas genes and repeat structures have been used to define 8 CRISPR subtypes, some of which are associated with an additional gene module encoding repeat-associated mysterious proteins (RAMPs).

There are diverse CRISPR systems in different organisms, and one of the simplest is the type II CRISPR system from *Streptococcus pyogenes*: only a single gene encoding the Cas9 protein and two RNAs, a mature CRISPR RNA (crRNA) and a partially complementary trans-acting RNA (tracrRNA), are necessary and sufficient for RNA-guided silencing of foreign DNAs (Gasiunas et al., 2012, PNAS 109: E2579-E2586; Jinek et al, 2012, Science 337: 816-821). Maturation of crRNA requires tracrRNA and RNase III (Deltcheva et al. 2011, Nature 471: 602-607). However, this requirement can be bypassed by using an engineered small guide RNA (sgRNA) containing a designed hairpin that mimics the tracrRNA-crRNA complex (Jinek et al., 2012, Science 337: 816-821). Base pairing between the sgRNA and target DNA causes double-strand breaks (DSBs) due to the endonuclease activity of Cas9. Binding specificity is determined by both sgRNA-DNA base pairing and a short DNA motif (protospacer adjacent motif [PAM] sequence: NGG) juxtaposed to the DNA complementary region (Marraffini & Sontheimer, 2010, Nature Reviews Genetics, 11: 181-190). For example, the CRISPR system requires a minimal set of two molecules, the Cas9 protein and the sgRNA, and therefore can be used as a host-independent gene-targeting platform. The Cas9/CRISPR can be harnessed for site-selective RNA-guided genome editing, such as targeting insertion see for example, Carroll, 2012, Molecular Therapy 20: 1658-1660; Chang et al., 2013, Cell Research 23: 465-472; Cho et al., 2013, Nature Biotechnol 31: 230-232; Cong et al., 2013, Science 339: 819-823; Hwang et al., 2013, Nature Biotechnol 31: 227-229; Jiang et al., 2013, Nature Biotechnol 31: 233-239; Mali et al., 2013, Science 339: 823-826; Qi et al., 2013, Cell 152: 1173-1183; Shen et al., 2013, Cell Research 23: 720-723; and Wang et al., 2013, Cell 153: 910-918). In particular, Wang et al. 2013, Cell 153: 910-918 describe targeted insertion using the CRISPR/Cas9 system combined with oligonucleotides.

Generation of a genetically modified immunodeficient mouse according to aspects of the present invention may include injection or transfection of appropriate nucleic acids, such as an expression construct encoding cas9 and an expression construct encoding a guide RNA specific for the gene to be targeted, for use in CRISPR, into a preimplantation embryo or stem cells, such as embryonic stem (ES) cells or induced pluripotent stem (iPS) cells. Optionally, cas9 and the guide RNA are encoding in a single expression construct.

TAL (Transcription Activator-Like) Effectors

Transcription activator-like (TAL) effectors or TALE (transcription activator-like effector) are derived from a plant pathogenic bacteria genus, *Xanthomonas*, and these proteins mimic plant transcriptional activators and manipulate the plant transcript, see Kay et al., 2007, Science, 318:648-651.

TAL effectors contain a centralized domain of tandem repeats, each repeat containing approximately 34 amino acids, which are key to the DNA binding specificity of these proteins. In addition, they contain a nuclear localization sequence and an acidic transcriptional activation domain, for a review see Schornack et al., 2006, J. Plant Physiol., 163(3): 256-272; Scholze and Boch, 2011, Curr Opin Microbiol, 14:47-53.

Specificity of TAL effectors depends on the sequences found in the tandem repeats. The repeated sequence includes approximately 102 bp and the repeats are typically 91-100% homologous with each other (Bones et al., 1989, Mol Gen Genet 218: 127-136). Polymorphism of the repeats is usually located at positions 12 and 13 and there appears to be a one-to-one correspondence between the identity of the hypervariable diresidues at positions 12 and 13 with the identity of the contiguous nucleotides in the TAL-effector's target sequence, see Moscou and Bogdanove 2009, Science 326: 1501; and Hoch et al., 2009, Science 326:1509-1512. The two hypervariable residues are known as repeat variable diresidues (RVDs), whereby one RVD recognizes one nucleotide of DNA sequence and ensures that the DNA binding domain of each TAL-effector can target large recognition sites with high precision (15-30 nt). Experimentally, the code for DNA recognition of these TAL-effectors has been determined such that an HD sequence at positions 12 and 13 leads to a binding to cytosine (C), NG binds to T, NI to A, C, G or T, NN binds to A or G, and IG binds to T. These DNA binding repeats have been assembled into proteins with new combinations and numbers of repeats, to make artificial transcription factors that are able to interact with new sequences and activate the expression of a reporter gene in plant cells (Boch et al., 2009, Science 326:1509-1512). These DNA binding domains have been shown to have general applicability in the field of targeted genomic editing or targeted gene regulation in all cell types, see Gaj et al., Trends in Biotechnol, 2013, 31(7):397-405. Moreover, engineered TAL effectors have been shown to function in association with exogenous functional protein effector domains such as a nuclease, not naturally found in natural *Xanthomonas* TAL-effect or proteins in mammalian cells. TAL nucleases (TALNs or TALENs) can be constructed by combining TALs with a nuclease, e.g. FokI nuclease domain at the N-terminus or C-terminus, Kim et al. 1996, PNAS 93:1156-1160; Christian et al., 2010, Genetics 186:757-761; Li et al., 2011, Nucleic Acids Res 39: 6315-6325; and Miller et al., 2011, Nat Biotechnol 29: 143-148. The functionality of TALENs to cause deletions by NHEJ has been shown in rat, mouse, zebrafish, *Xenopus*, medaka, rat and human cells, Ansai et al., 2013, Genetics, 193: 739-749; Carlson et al., 2012, PNAS, 109: 17382-17387; Hockemeyer et al., 2011, Nature Biotechnol., 29: 731-734; Lei et al., 2012, PNAS, 109: 17484-17489; Moore et al., 2012, PLoS ONE, 7: e37877; Stroud et al., 2013, J. Biol. Chem., 288: 1685-1690; Sung et al., 2013, Nature Biotechnol 31: 23-24; Wefers et al., 2013, PNAS 110: 3782-3787.

For TALEN, methods of making such are further described in U.S. Pat. Nos. 8,420,782; 8,450,471; 8,450,107; 8,440,432; 8,440,431 and U.S. Patent Publication Nos. US20130137161 and US20130137174.

Other useful endonucleases may include, for example, HhaI, HindIII, NotI, BbvCI, EcoRI, Bg/I, and AlwI. The fact that some endonucleases (e.g., FokI) only function as dimers can be capitalized upon to enhance the target specificity of the TAL effector. For example, in some cases each FokI monomer can be fused to a TAL effector sequence that recognizes a different DNA target sequence, and only when the two recognition sites are in close proximity do the inactive monomers come together to create a functional enzyme. By requiring DNA binding to activate the nuclease, a highly site-specific restriction enzyme can be created.

In some embodiments, the TALEN may further include a nuclear localization signal or sequence (NLS). A NLS is an amino acid sequence that facilitates targeting the TALEN nuclease protein into the nucleus to introduce a double stranded break at the target sequence in the chromosome.

Nuclear localization signals are known in the art, see, for example, Makkerh et al. 1996, Curr Biol. 6:1025-1027. NLS include the sequence from SV40 Large T-antigen, Kalderon 1984, Cell, 39: 499-509; the NLS from nucleoplasmin, described in detail in Dingwall et al., 1988, J Cell Biol., 107, 841-9. Further examples are described in McLane and Corbett 2009, IUBMB Life, 61, 697-70; Dopie et al. 2012, PNAS, 109, E544-E552.

The cleavage domain may be obtained from any endonuclease or exonuclease. Non-limiting examples of endonucleases from which a cleavage domain may be derived include, but are not limited to, restriction endonucleases and homing endonucleases. See, for example, 2002-2003 Catalog, New England Biolabs, Beverly, Mass.; and Belfort et al. (1997) Nucleic Acids Res. 25:3379-3388. Additional enzymes that cleave DNA are known, e.g., SI Nuclease; mung bean nuclease; pancreatic DNase I; micrococcal nuclease; yeast HO endonuclease. See also Linn et al. (eds.) Nucleases, Cold Spring Harbor Laboratory Press, 1993. One or more of these enzymes, or functional fragments thereof, may be used as a source of cleavage domains.

Zinc Finger-Mediated Genome Editing

The use of zinc finger nucleases (ZFN) for gene editing, such as for targeted insertion via a homology-directed repair process, has been well established. For example, see Carbery et al., 2010, Genetics, 186: 451-459; Cui et al., 2011, Nature Biotechnol., 29: 64-68; Hauschild et al., 2011, PNAS, 108: 12013-12017; Orlando et al., 2010, Nucleic Acids Res., 38: e152-e152; and Porteus & Carroll, 2005, Nature Biotechnology, 23: 967-973.

Components of the ZFN-mediated process include a zinc finger nuclease with a DNA binding domain and a cleavage domain. Such are described for example in Beerli et al. (2002) Nature Biotechnol., 20:135-141; Pabo et al. (2001) Ann. Rev. Biochem., 70:313-340; Isalan et al. (2001) Nature Biotechnol. 19:656-660; Segal et al. (2001) Curr Opin. Biotechnol., 12:632-637; and Choo et al. (2000) Curr Opin. Struct. Biol., 10:411-416; and U.S. Pat. Nos. 6,453,242 and 6,534,261. Methods to design and select a zinc finger binding domain to a target sequence are known in the art, see for example Sera, et al., Biochemistry 2002, 41, 7074-7081; U.S. Pat. Nos. 6,607,882; 6,534,261 and 6,453,242.

In some embodiments, the zinc finger nuclease may further include a nuclear localization signal or sequence (NLS). A NLS is an amino acid sequence that facilitates targeting the zinc finger nuclease protein into the nucleus to introduce a double stranded break at the target sequence in the chromosome. Nuclear localization signals are known in the art. See, for example, Makkerh et al. (1996) Current Biology 6:1025-1027 and others described herein.

The cleavage domain may be obtained from any endonuclease or exonuclease. Non-limiting examples of endonucleases from which a cleavage domain may be derived include, but are not limited to, restriction endonucleases and homing endonucleases. See, for example, 2002-2003 Catalog, New England Biolabs, Beverly, Mass.; and Belfort et al. (1997) Nucleic Acids Res. 25:3379-3388. Additional enzymes that cleave DNA are known (e.g., SI Nuclease; mung bean nuclease; pancreatic DNase I; micrococcal nuclease; yeast HO endonuclease). See also Linn et al. (eds.) Nucleases, Cold Spring Harbor Laboratory Press, 1993. One or more of these enzymes (or functional fragments thereof) may be used as a source of cleavage domains. A cleavage domain also may be derived from an enzyme or portion thereof, as described above, that requires dimerization for cleavage activity.

Two zinc forger nucleases may be required for cleavage, as each nuclease includes a monomer of the active enzyme dimer. Alternatively, a single zinc finger nuclease may include both monomers to create an active enzyme dimer. Restriction endonucleases (restriction enzymes) are present in many species and are capable of sequence-specific binding to DNA (at a recognition site), and cleaving DNA at or near the site of binding. Certain restriction enzymes (e.g., Type IIS) cleave DNA at sites removed from the recognition site and have separable binding and cleavage domains. For example, the Type IIS enzyme FokI catalyzes double stranded cleavage of DNA, at 9 nucleotides from its recognition site on one strand and 13 nucleotides from its recognition site on the other. See, for example, U.S. Pat. Nos. 5,356,802; 5,436,150 and 5,487,994; as well as Li et al. (1992) PNAS 89:4275-4279; Li et al. (1993) PNAS 90:2764-2768; Kim et al. (1994) PNAS 91:883-887; Kim et al. (1994) J. Biol. Chem. 269:31, 978-31, 982. Thus, a zinc finger nuclease may include the cleavage domain from at least one Type IIS restriction enzyme and one or more zinc finger binding domains, which may or may not be engineered. Exemplary Type IIS restriction enzymes are described for example in International Publication WO 07/014275, the disclosure of which is incorporated by reference herein in its entirety. Additional restriction enzymes also contain separable binding and cleavage domains, and these also are contemplated by the present disclosure. See, for example, Roberts et al. (2003) Nucleic Acids Res. 31: 418-420. An exemplary Type IIS restriction enzyme, whose cleavage domain is separable from the binding domain, is FokI. This particular enzyme is active as a duper (Bitinaite et al. 1998, PNAS 95: 10,570-10,575). Accordingly, for the purposes of the present disclosure, the portion of the FokI enzyme used in a zinc finger nuclease is considered a cleavage monomer. Thus, for targeted double stranded cleavage using a FokI cleavage domain, two zinc finger nucleases, each including a FokI cleavage monomer, may be used to reconstitute an active enzyme dimer. Alternatively, a single polypeptide molecule containing a zinc finger binding domain and two FokI cleavage monomers may also be used. In certain embodiments, the cleavage domain may include one or more engineered cleavage monomers that minimize or prevent homodimerization, as described, for example, in U.S. Patent Publication Nos. 20050064474, 20060188987, and 20080131962, each of which is incorporated by reference herein in its entirety. By way of non-limiting example, amino acid residues at positions 446, 447, 479, 483, 484, 486, 487, 490, 491, 496, 498, 499, 500, 531, 534, 537 and 538 of FokI are all targets for influencing dimerization of the FokI cleavage half-domains. Exemplary engineered cleavage monomers of FokI that form obligate heterodimers include a pair in which a first cleavage monomer includes mutations at amino acid residue positions 490 and 538 of FokI and a second cleavage monomer that includes mutations at amino-acid residue positions 486 and 499. Thus, in one embodiment, a mutation at amino acid position 490 replaces Glu (E) with Lys (K); a mutation at amino acid residue 538 replaces Ile (I) with Lys (K); a mutation at amino acid residue 486 replaces Gln (Q) with Glu (E); and a mutation at position 499 replaces Ile (I) with Lys (K). Specifically, the engineered cleavage monomers may be prepared by mutating positions 490 from E to K and 538 from I to K in one cleavage monomer to produce an engineered cleavage monomer designated "E490K:I538K" and by mutating positions 486 from Q to E and 499 from I to L in another cleavage monomer to produce an engineered cleavage monomer designated "Q486E:I499L." The above described engineered cleavage monomers are obligate heterodimer mutants in which aberrant cleavage is minimized or abolished. Engineered cleavage monomers may be prepared using a suitable method, for example, by site-directed mutagenesis of wild-type cleavage monomers (FokI) as described in U.S. Patent Publication No. 20050064474.

The zinc finger nuclease described above may be engineered to introduce a double stranded break at the targeted site of integration. The double stranded break may be at the targeted site of integration, or it may be up to 1, 2, 3, 4, 5, 10, 15, 20, 25, 30, 35, 40, 45, 50, 100 or 1000 nucleotides away from the site of integration. In some embodiments, the double stranded break may be up to 1, 2, 3, 4, 5, 10, 15, or 20 nucleotides away from the site of integration. In other embodiments, the double stranded break may be up to 10, 15, 20, 25, 30, 35, 40, 45 or 50 nucleotides away from the site of integration. In yet other embodiments, the double stranded break may be up to 50, 100 or 1000 nucleotides away from the site of integration.

The DRAP technology has been described in U.S. Pat. Nos. 6,534,643; 6,858,716 and 6,830,910 and Watt et al., 2006.

Generation of a genetically modified immunodeficient mouse whose genome includes a genetic modification, wherein the genetic modification renders the mouse deficient in MHC I and MHC II can be achieved by introduction of a gene targeting vector into a preimplantation embryo or stem cells, such as embryonic stem (ES) cells or induced pluripotent stem (iPS) cells.

The term "gene targeting vector" refers to a double-stranded recombinant DNA molecule effective to recombine with and mutate a specific chromosomal locus, such as by insertion into or replacement of the targeted gene.

For targeted gene disruption, e.g. mutation, a gene targeting vector is made using recombinant DNA techniques and includes 5' and 3' sequences which are homologous to the stem cell endogenous target gene. The gene targeting vector optionally and preferably further includes a selectable marker such as neomycin phosphotransferase, hygromycin or puromycin. Those of ordinary skill in the art are capable of selecting sequences for inclusion in a gene targeting vector and using these with no more than routine experimentation. Gene targeting vectors can be generated recombinantly or synthetically using well-known methodology.

For methods of DNA injection of a gene targeting vector into a preimplantation embryo, the gene targeting vector is linearized before injection into non human preimplantation embryos. Preferably, the gene targeting vector is injected into fertilized oocytes. Fertilized oocytes are collected from superovulated females the day after mating (0.5 dpc) and injected with the expression construct. The injected oocytes are either cultured overnight or transferred directly into oviducts of 0.5-day p.c. pseudopregnant females. Methods for superovulation, harvesting of oocytes, gene targeting vector injection and embryo transfer are known in the art and described in Manipulating the Mouse Embryo: A Laboratory Manual, 3rd edition, Cold Spring Harbor Laboratory Press; Dec. 15, 2002, ISBN-10: 0879695919. Offspring can be tested for the presence of target gene disruption, e.g. mutation, by DNA analysis, such as PCR, Southern blot or sequencing. Mice having a disrupted, e.g. mutated, target gene can be tested for expression of the target protein such as by using ELISA or Western blot analysis and/or mRNA expression such as by RT-PCR.

Alternatively the gene targeting vector may be transfected into stem cells (ES cells or iPS cells) using well-known methods, such as electroporation, calcium-phosphate precipitation and lipofection.

Mouse ES cells are grown in media optimized for the particular line. Typically ES media contains 15% fetal bovine serum (FBS) or synthetic or semi-synthetic equivalents, 2 mM glutamine, 1 mM Na Pyruvate, 0.1 mM non-essential amino acids, 50 U/ml penicillin and streptomycin, 0.1 mM 2-mercaptoethanol and 1000 U/ml LIF (plus, for some cell lines chemical inhibitors of differentiation) in Dulbecco's Modified Eagle Media (DMEM). A detailed description is known in the art (Tremml et al., 2008, Current Protocols in Stem Cell Biology, Chapter 1:Unit 1C.4. For review of inhibitors of ES cell differentiation, see Buehr, M., et al. (2003). Genesis of embryonic stem cells. Philosophical Transactions of the Royal Society B: Biological Sciences 358, 1397-1402.

The cells are screened for target gene disruption, e.g. mutation, by DNA analysis, such as PCR, Southern blot or sequencing. Cells with the correct homologous recombination event disrupting the target gene can be tested for expression of the target protein such as by using ELISA or Western blot analysis and/or mRNA expression such as by RT-PCR If desired, the selectable marker can be removed by treating the stem cells with Cre recombinase. Alter Cre recombinase treatment the cells are analyzed for the presence of the nucleic acid encoding the target protein.

Selected stem cells with the correct genomic event disrupting the target gene can be injected into preimplantation embryos. For microinjection, ES or iPS cell are rendered to single cells using a mixture of trypsin and EDTA, followed by resuspension in ES media. Groups of single cells are selected using a finely drawn-out glass needle (20-25 micrometer inside diameter) and introduced through the embryo's zona pellucida and into the blastocysts cavity (blastocoel) using an inverted microscope fitted with micromanipulators. As an alternative to blastocyst injection, stem cells can be injected into early stage embryos (e.g. 2-cell, 4-cell, 8-cell, premorula or morula). Injection may be assisted with a laser or piezo pulses drilled opening the zona pellucida. Approximately 9-10 selected stem cells (ES or iPS cells) are injected per blastocysts, or 8-cell stage embryo, 6-9 stem cells per 4-cell stage embryo, and about 6 stem cells per 2-cell stage embryo. Following stem cell introduction, embryos are allowed to recover for a few hours at 37° C. in 5% $CO_2$, 5% $O_2$ in nitrogen or cultured overnight before transfer into pseudopregnant recipient females. In a further alternative to stem cell injection, stem cells can be aggregated with morula stage embryos. All these methods are well established and can be used to produce stem cell chimeras. For a more detailed description see Manipulating the Mouse Embryo: A Laboratory Manual, 3rd edition (A. Nagy, M. Gertsenstein, K. Vintersten, R. Behringer, Cold Spring Harbor Laboratory Press; Dec. 15, 2002, ISBN-10: 0879695919, Nagy et al., 1990, Development 110, 815-821; U.S. Pat. No. 7,576,259: Method for making genetic modifications, U.S. Pat. Nos. 7,659,442, 7,294,754, Kraus et al. 2010, Genesis 48, 394-399).

Pseudopregnant embryo recipients are prepared using methods known in the art. Briefly, fertile female mice between 6-8 weeks of age are mated with vasectomized or sterile males to induce a hormonal state conductive to supporting surgically introduced embryos. At 2.5 days post coitum (dpc) up to 15 of the stem cell containing blastocysts are introduced into the uterine horn very near to the uterus-oviduct junction. For early stage embryos and morula, such embryos are either cultured in vitro into blastocysts or implanted into 0.5 dpc or 1.5 dpc pseudopregnant females according to the embryo stage into the oviduct. Chimeric pups from the implanted embryos are born 16 days after the transfer depending on the embryo age at implantation. Chimeric males are selected for breeding. Offspring can be analyzed for transmission of the ES cell genome by coat color and nucleic acid analysis, such as PCR, Southern blot or sequencing. Further, the expression of the target gene can be analyzed for target mRNA or protein expression such as by protein analysis, e.g. immunoassay, or functional assays, to confirm target gene disruption. Offspring having the target gene disruption, e.g. mutation, are intercrossed to create non-human animals homozygous for the target gene disruption. The transgenic mice are crossed to the immunodeficient mice to create a congenic immunodeficient strain with the target gene disruption.

Methods of assessing a genetically modified mouse to determine whether the target gene is disrupted such that the mouse lacks the capacity to express the target gene are well-known and include standard techniques such as nucleic acid assays, spectrometric assays, immunoassays and functional assays.

One or more standards can be used to allow quantitative determination of target protein in a sample.

Assays for assessment of functional target protein in an animal having a putative disruption of the target gene can be performed. Assays for assessment of function of the target protein in an animal having a putative disruption of the target gene are described herein.

Optionally, a genetically modified immunodeficient mouse according to aspects of the present invention is produced by selective breeding. A first parental strain of mouse which has a first desired genotype may be bred with a second parental strain of mouse which has a second desired genotype to produce offspring which are genetically modified mice having the first and second desired genotypes. For example, a first mouse which is immunodeficient may be bred with a second mouse which has an MHC I gene disruption such that expression of MHC I is absent or reduced to produce offspring which are immunodeficient and have an MHC I gene disruption such that expression of MHC I is absent or reduced. In further examples, an NSG mouse may be bred with a mouse which has a target gene disruption such that expression of the target gene is absent or reduced to produce offspring which are immunodeficient and have a target gene disruption such that expression of the target protein is absent or reduced.

Aspects of the invention provide a genetically modified immunodeficient mouse that includes a target gene disruption in substantially all of their cells, as well as a genetically modified mouse that include a target gene disruption in some, but not all their cells.

Immunodeficiency

The term "immunodeficient non-human animal" refers to a non-human animal characterized by one or more of: a lack of functional immune cells, such as T cells and B cells; a DNA repair defect; a defect in the rearrangement of genes encoding antigen-specific receptors on lymphocytes; and a lack of immune functional molecules such as IgM, IgG1, IgG2a, IgG2b, IgG3 and IgA.

According to aspects of the present invention, a genetically modified immunodeficient non-human animal whose genome includes a genetic modification, wherein the genetic modification renders the non-human animal deficient in MHC I and MHC II activity, provided according to aspects of the present invention is a mouse. While description herein refers primarily to aspects of the present invention in which the genetically modified immunodeficient non-human animal is a mouse, the genetically modified immunodeficient non-human animal can also be a mammal such as a rat, gerbil, guinea pig, hamster, rabbit, pig, sheep, or non-human primate.

The term "immunodeficient mouse" refers to a mouse characterized by one or more of: a lack of functional immune cells, such as T cells and B cells; a DNA repair defect; a defect in the rearrangement of genes encoding antigen-specific receptors on lymphocytes; and a lack of immune functional molecules such as IgM, IgG1, IgG2a, IgG2b, IgG3 and IgA. Immunodeficient mice can be characterized by one or more deficiencies in a gene involved in immune function, such as Rag1 and Rag2 (Oettinger, M. A et al., Science, 248:1517-1523, 1990; and Schatz, D. G. et al., Cell, 59:1035-1048, 1989) Immunodeficient mice may have any of these or other defects which result in abnormal immune function in the mice.

A particularly useful immunodeficient mouse strain is NOD.Cg-Prkdc$^{scid}$ Il2rg$^{tm1Wjl}$/SzJ, commonly referred to as NOD scid gamma (NSG) mice, described in detail in Shultz L D et al., 2005, J. Immunol, 174:6477-89. NSG is representative of the mouse substrain developed at The Jackson Laboratory. Other similar mouse substrains may be used to make NSG and are intended to be encompassed by the present invention. Other useful immunodeficient mouse strains include NOD.Cg-Rag1$^{tm1Mom}$ Il2rg$^{tm1Wjl}$/SzJ, see Shultz L D et al., 2008, Clin Exp Immunol 154(2):270-84 commonly referred to as NRG mice; and NOD.Cg-Prkdc$^{scid}$ Il2rg$^{tm1Sug}$/JicTac or NOD/Shi-scid-IL2r$\gamma^{null}$, commonly referred to as NOG mice, such as described in detail in Ito, M. et al., Blood 100, 3175-3182 (2002).

The term "severe combined immune deficiency (SCID)" refers to a condition characterized by absence of T cells and lack of B cell function.

Common forms of SCID include: X-linked SCID which is characterized by gamma chain gene mutations in the IL2RG gene and the lymphocyte phenotype T(−) B(+) NK(−); and autosomal recessive SCID characterized by Jak3 gene mutations and the lymphocyte phenotype T(−) B(+) NK(−), ADA gene mutations and the lymphocyte phenotype T(−) B(−) NK(−), IL-7R alpha-chain mutations and the lymphocyte phenotype T(−) B(+) NK(+), CD3 delta or epsilon mutations and the lymphocyte phenotype T(−) B(+) NK(+), RAG1/RAG2 mutations and the lymphocyte phenotype T(−) B(−) NK(+), Artemis gene mutations and the lymphocyte phenotype T(−) B(−) NK(+), CD45 gene mutations and the lymphocyte phenotype T(−) B(+) NK(+).

In further aspects, a genetically modified immunodeficient mouse has a defect in its endogenous gene encoding DNA-dependent protein kinase, catalytic subunit (Prkdc) which causes the mouse to express a defective endogenous DNA-dependent protein kinase, catalytic subunit and/or a reduced amount of endogenous DNA-dependent protein kinase, catalytic subunit, or the mouse may not express endogenous DNA-dependent protein kinase, catalytic subunit at all. The immunodeficient mouse can optionally be Prkdc null such that it lacks a functional endogenous Prkdc gene).

A genetically modified mouse according to aspects of the present invention has the severe combined immunodeficiency mutation (Prkdc$^{scid}$), commonly referred to as the scid mutation. The scid mutation is well-known and located on mouse chromosome 16 as described in Bosma, et al, Immunogenetics 29:54-56, 1989. Mice homozygous for the scid mutation are characterized by an absence of functional T cells and B cells, lymphopenia, hypoglobulinemia and a normal hematopoetic microenvironment. The scid mutation can be detected, for example, by detection of markers for the scid mutation using well-known methods, such as PCR or flow cyotometry.

A genetically modified mouse according to aspects of the present invention has an IL2 receptor gamma chain deficiency. The term "IL2 receptor gamma chain deficiency" refers to decreased IL2 receptor gamma chain. Decreased IL2 receptor gamma chain can be due to gene deletion or mutation. Decreased IL2 receptor gamma chain can be detected, for example, by detection of IL2 receptor gamma chain gene deletion or mutation and/or detection of decreased IL2 receptor gamma chain expression using well-known methods.

According to aspects of the present invention, a genetically modified immunodeficient NSG mouse is provided whose genome includes a genetic modification, wherein the genetic modification renders the immunodeficient mouse deficient in MHC I and MHC II, such that the genetically modified immunodeficient NSG mouse lacks functional MHC I and lacks functional MHC II.

According to aspects of the present invention, a genetically modified immunodeficient NRG mouse is provided whose genome includes a genetic modification, wherein the genetic modification renders the immunodeficient mouse deficient in MHC I and MHC II, such that the genetically modified immunodeficient NRG mouse lacks functional MHC I and lacks functional MHC II.

According to aspects of the present invention, a genetically modified immunodeficient NOG mouse is provided whose genome includes a genetic modification, wherein the genetic modification renders the immunodeficient mouse deficient in MHC I and MHC II, such that the genetically modified immunodeficient NOG mouse lacks functional MHC I and lacks functional MHC II. with the proviso that the immunodeficient mouse is not a NOD/Shi-scid-IL2rγ$^{null}$ mouse characterized by β2m (component of MHC I) knockout and IAβ (light chain of MHC II) knockout.

NSG-($K^b$ $D^b$)$^{null}$ ($IA^{null}$) Mice

According to aspects of the present invention, a genetically modified immunodeficient mouse deficient in MHC class I and MHC class II is a NOD.Cg-Prkdc$^{scid}$ H2-K1$^{tm1Bpe}$ H2-Ab1$^{em1Mvw}$ H2-D1$^{tm1Bpe}$ Il2rg$^{tm1Wjl}$/SzJ (abbreviated as NSG-($K^b$ $D^b$)$^{null}$ ($IA^{null}$) mouse which lacks functional MHC I and lacks functional MHC II. The NSG-($K^b$ $D^b$)$^{null}$ ($IA^{null}$) mouse lacks functional MHC I due to a homozygous null mutation of H2-K and H2-D MHC I α protein subclasses (abbreviated ($K^b$ $D^b$)$^{null}$ ($IA^{null}$). The NSG-($K^b$ $D^b$)$^{null}$ ($IA^{null}$) mouse lacks functional MHC II due to a homozygous null mutation of H-2A subclass of MHC II (abbreviated as $IA^{null}$).

Although both NSG-($K^b$ $D^b$)$^{null}$ ($IA^{null}$) and NSG-B2M$^{null}$ (IA IE)$^{null}$ mice lack functional MHC I and MHC II, unexpectedly, human IgG clearance in NSG-($K^b$ $D^b$)$^{null}$ ($IA^{null}$) mice differs significantly from that of NSG-B2M$^{null}$ (IA IE)$^{null}$ mice. While NSG-($K^b$ $D^b$)$^{null}$ ($IA^{null}$) mice exhibit a slow human IgG clearance pattern (similar to that observed in NSG mice; note that NSG mice have functional MHC I and MHC II), the NSG-B2M$^{null}$ (IA IE)$^{null}$ mice exhibits a rapid IgG clearance (see FIG. 2) such that it renders this mouse model not suitable for use in antibody testing. An NSG-($K^b$ $D^b$)$^{null}$ ($IA^{null}$)) mouse of the present invention is characterized by clearance of no more than 60%, such as clearance of no more than 70%, 80%, or 90%, of administered human IgG in a time period of 2 days following administration of the human IgG. About 90% of human IgG was cleared in NSG-($K^b$ $D^b$)$^{null}$ ($IA^{null}$) mice after about 2 weeks. The term "clearance" used in reference to human IgG administered to a mouse refers to a process of removal of functional human IgG from the mouse.

NSG-B2M$^{null}$(IA IE)$^{null}$ Mice

According to aspects of the present invention, a genetically modified immunodeficient mouse deficient in MHC class I and MHC class II which lacks functional MHC I and lacks functional MHC II is a NOD.Cg-Prkdc$^{scid}$ H2-K1$^{tm1Bpe}$ H2-Ab1$^{em1Mvw}$ H2-D1$^{tm1Bpe}$ Il2rg$^{tm1Wjl}$ Tg(Ins2-HBEGF) 6832Ugfm/Sz (abbreviated as NSG-B2M$^{null}$ (IA IE)$^{null}$) mouse. The NSG-B2M$^{null}$ (IA IE)$^{null}$ mouse lacks functional MHC I due to a homozygous null mutation of β2 microglobulin (abbreviated B2M$^{null}$). The NSG-B2M$^{null}$ (IA IE)$^{null}$ mouse lacks functional MHC II due to a homozygous null mutation of H-2A and H-2E subclasses of MHC II (abbreviated as (IA IE)$^{null}$).

Rapid clearance of human IgG in NSG-B2M$^{null}$ (IA IE)$^{null}$) mice was observed. About 90% of human IgG was cleared in NSG-B2M$^{null}$ (IA IE$^{null}$) mice after about 2 days, see FIG. 2.

NSG-RIP-DTR ($K^b$ $D^b$)$^{null}$ ($IA^{null}$) Mice

According to aspects of the present invention, a genetically modified immunodeficient mouse deficient in MHC class I and MHC class II which lacks functional MHC I and lacks functional MHC II is a NOD.Cg-Prkdc$^{scid}$ H2-K1$^{tm1Bpe}$ H2-Ab1$^{em1Mvw}$ H2-D1$^{tm1Bpe}$ Il2rg$^{tm1Wjl}$ Tg(Ins2-HBEGF) 6832Ugfm/Sz transgenic mouse, abbreviated as NSG-RIP-DTR ($K^b$ $D^b$)$^{null}$ ($IA^{null}$), which expresses the diphtheria toxin receptor under the control of the rat insulin promoter on an NSG background. Injection of diphtheria toxin (DT) into mice expressing the diphtheria toxin receptor under the control of the rat insulin promoter leads to mouse pancreatic beta cell death and hyperglycemia. The NSG-RIP-DTR ($K^b$ $D^b$)$^{null}$ ($IA^{null}$) strain permits the complete and specific ablation of mouse pancreatic beta cells, avoiding the broadly toxic effects of diabetogenic drugs such as streptozotocin.

Mouse Model Including Allogeneic and/or Xenogeneic Cells

A genetically modified immunodeficient mouse according to aspects of the present invention further includes allogeneic and/or xenogeneic cells or tissues. Increased survival of genetically modified immunodeficient mice of the present invention to which allogeneic and/or xenogeneic cells or tissues have been administered observed due to reduction or absence of graft versus host disease (GVHD) since the mice lack functional MHC I and functional MHC II. For example, the genetically modified immunodeficient mice lacking functional MHC I and functional MHC II survive longer following administration of allogeneic and/or xenogeneic cells or tissues to the genetically modified immunodeficient mice than in immunodeficient mice of the same type which do not lack functional MHC I and functional MHC II.

The allogeneic and/or xenogeneic cells or tissues administered to a genetically modified immunodeficient mouse lacking functional MHC I and functional MHC II are not limited with respect to source or type. Administration of the allogeneic and/or xenogeneic cells or tissues to a genetically modified immunodeficient mouse lacking functional MHC I and functional MHC II provides a mouse model for various uses depending on the type of allogeneic and/or xenogeneic cells or tissues administered. Xenogeneic cells or tissues administered include, but are not limited to, human pancreatic cells; human pancreatic islets; human pancreatic beta cells; stem cells, such as but not limited to human CD34+ cells; human patient-derived primary human tumor cells; human tumor cell line cells; human hepatocytes; human hematopoietic cells; isolated or mixed populations of human differentiated blood cells such as leukocytes, red blood cells, lymphocytes, monocytes, neutrophils, eosinophils, basophils, platelets. NK cells, human peripheral blood mononuclear cells (PBMC), and combinations of two or more types of cells or tissues.

Allogeneic and/or xenogeneic cells or tissues administered include, but are not limited to, non-human pancreatic cells; non-human pancreatic islets; non-human pancreatic beta cells; stem cells, such as but not limited to non-human CD34+ cells; non-non-human primary tumor cells; non-human tumor cell line cells; non human hepatocytes; non-human hematopoietic cells; isolated or mixed populations of non human differentiated blood cells such as leukocytes, red blood cells, lymphocytes, monocytes, neutrophils, eosinophils, basophils, platelets, NK cells, and non-human peripheral blood mononuclear cells, and combinations of two or more types of cells or tissues.

Optionally, allogeneic and/or xenogeneic cells or tissues administered to a genetically modified immunodeficient mouse lacking functional MHC I and functional MHC II are genetically modified.

According to particular aspects of the present invention, human T cells are administered to an immunodeficient genetically modified mouse lacking functional MHC I and functional MHC II. The human T cells can be administered as an isolated population of human T cells, as a population of human stem cells or human precursor cells that will differentiate into human T cells in the mouse, or as a mixed population of cells of which human T cells are a subset.

According to particular aspects of the present invention, human tumor cells are administered to an immunodeficient genetically modified mouse lacking functional MHC I and functional MHC II. The human tumor cells can be administered as an isolated population of human tumor cells, such as but not limited to, human patient-derived primary human tumor cells or human tumor cell line cells, or as a mixed population of cells of which human tumor cells are a subset.

According to particular aspects of the present invention, human tumor cells are administered to an immunodeficient genetically modified mouse lacking functional MHC I and functional MHC II. The human tumor cells can be administered as an isolated population of human tumor cells, such as but not limited to, human patient-derived primary human tumor cells or human tumor cell line cells, or as a mixed population of cells of which human tumor cells are a subset.

Allogeneic and/or xenogeneic cells or tissues can be administered into genetically modified immunodeficient mouse of the present invention via various routes, such as, but not limited to, intravenous or intraperitoneal administration.

The allogeneic and/or xenogeneic cells or tissues can be administered one or more times to the genetically modified immunodeficient mouse. Increased survival of a genetically modified immunodeficient mouse lacking functional MHC I and functional MHC II of the present invention to which allogeneic and/or xenogeneic cells or tissues have been administered is due to reduction or absence of graft versus host disease (GVHD).

According to aspects of the present invention, differentiated allogeneic and/or xenogeneic cells or tissues are introduced to an immunodeficient genetically modified mouse lacking functional MHC I and functional MHC II by administration of one or more types of stem cells which engraft in the immunodeficient genetically modified mouse and produce differentiated cells or tissues by differentiation of the stem cells in the mouse.

The number of allogeneic and/or xenogeneic cells administered is not considered limiting. Thus, the number of administered allogeneic and/or xenogeneic cells is generally in the range of $1\times10^3$ to $1\times10^8$ (1,000 to 100,000,000), although more or fewer can be used.

Thus, a method according to aspects of the present invention can include administering about $1\times10^3$ (1000) to about $1\times10^8$ (100,000,000), about $1\times10^4$ (10,000) to about $1\times10^8$ (100,000,000), about $1\times10^4$ (10,000) to about $1\times10^7$ (10,000,000), about $1\times10^5$ (100,000) to about $1\times10^7$ (10,000,000), about $1\times10^3$ (1,000) to about $1\times10^4$ (10,000), about $5\times10^3$ (5,000) to about $5\times10^4$ (50,000), about $1\times10^4$ (10,000) to about $1\times10^5$ (100,000), about $5\times10^4$ (50,000), to about $5\times10^5$ (500,000), about $1\times10^6$ (1,000,000) to about $1\times10^8$ (100,000,000), about $5\times10^6$ (5,000,000) to about $1\times10^8$ (100,000,000), about $1\times10^7$ (10,000,000), to about $1\times10^8$ (100,000,000), about $2\times10^4$ (20,000) to about $5\times10^5$ (500,000), or about $5\times10^4$ (50,000) to about $2\times10^5$ (200,000), allogeneic and/or xenogeneic cells to the immunodeficient genetically modified mouse. The method can include administering at least about $1\times10^2$ (100), about $2\times10^2$ (200), about $3\times10^2$ (300), about $4\times10^2$ (400), about $5\times10^2$ (500), about $6\times10^2$ (600), about $7\times10^2$ (700), about $8\times10^2$ (800), about $9\times10^2$ (900), about $1\times10^3$ (1000), about $2\times10^3$ (2000), about $3\times10^3$ (3000), about $4\times10^3$ (4000), about $5\times10^3$ (5000), about $6\times10^3$ (6000), about $7\times10^3$ (7000), about $8\times10^3$ (8000), about $9\times10^3$ (9000), about $1\times10^4$ (10,000), about $2\times10^4$ (20,000), about $3\times10^4$ (30,000), about $4\times10^4$ (40,000), about $5\times10^4$ (50,000), about $6\times10^4$ (60,000), about $7\times10^4$ (70,000), about $8\times10^4$ (80,000), about $9\times10^4$ (90,000), about $1\times10^5$ (100,000), about $2\times10^5$ (200,000), about $3\times10^5$ (300,000), about $4\times10^5$ (400,000), about $5\times10^5$ (500,000), about $6\times10^5$ (600,000), about $7\times10^5$ (700,000), about $8\times10^5$ (800,000), about $9\times10^5$ (900,000), about $1\times10^6$ (1,000,000), about $2\times10^6$ (2,000,000), about $3\times10^6$ (3,000,000), about $4\times10^6$ (4,000,000), about $5\times10^6$ (5,000,000), about $6\times10^6$ (6,000,000), about $7\times10^6$ (7,000,000), about $8\times10^6$ (8,000,000), about $9\times10^6$ (9,000,000), about $1\times10^7$ (10,000,000), about $2\times10^7$ (20,000,000), about $3\times10^7$ (30,000,000), about $4\times10^7$ (40,000,000), about $5\times10^7$ (50,000,000), about $6\times10^7$ (60,000,000), about $7\times10^7$ (70,000,000), about $8\times10^7$ (80,000,000), about $9\times10^7$ (90,000,000), or about $1\times10^8$ (100,000,000), allogeneic and/or xenogeneic cells to the immunodeficient genetically modified mouse. Those of ordinary skill will be able to determine a number of allogeneic and/or xenogeneic cells to be administered to a specific mouse using no more than routine experimentation.

Administering allogeneic and/or xenogeneic cells to a mouse can include administering a composition comprising allogeneic and/or xenogeneic cells to the mouse. The composition can further include, for example, water, a tonicity-adjusting agent (e.g., a salt such as sodium chloride), a pH buffer (e.g., citrate), and/or a sugar (e.g., glucose).

Engraftment of allogeneic and/or xenogeneic hematopoietic stem cells in genetically modified immunodeficient animals is characterized by the presence of differentiated allogeneic and/or xenogeneic cells, such as hematopoietic cells in the genetically modified immunodeficient mice of the present invention. Engraftment of allogeneic and/or xenogeneic cells can be assessed by any of various methods, such as, but not limited to, flow cytometric analysis of cells in the animals to which the allogeneic and/or xenogeneic are administered at one or more time points following the administration of the cells.

Tumor Xenograft

Various aspects of the invention relate to administering xenogeneic tumor cells to a genetically modified immunodeficient mouse of the present invention.

Xenogeneic tumor cells administered to a genetically modified immunodeficient mouse of the present invention can be any of various tumor cells, including but not limited to, cells of a tumor cell line and primary tumor cells. The xenogeneic tumor cells may be derived from any of various organisms, preferably mammalian, including human, non-human primate, rat, guinea pig, rabbit, cat, dog, horse, cow, goat, pig and sheep.

According to specific aspects of the present invention, the xenogeneic tumor cells are human tumor cells. According to specific aspects of the present invention, the human tumor cells are present in a sample obtained from the human, such as, but not limited to, in a blood sample, tissue sample, or sample obtained by biopsy of a human tumor.

Tumor cells obtained from a human can be administered directly to a genetically modified immunodeficient mouse of the present invention or may be cultured in vitro prior to administration to the genetically modified immunodeficient mouse.

As used herein, the term "tumor" refers to cells characterized by unregulated growth including, but not limited to, pre-neoplastic hyperproliferation, cancer in-situ, neoplasms, metastases and solid and non-solid tumors. Examples of tumors are those caused by cancer include, but are not limited to, lymphoma, leukemia, squamous cell cancer, small-cell lung cancer, non-small cell lung cancer, adenocarcinoma of the lung, squamous carcinoma of the lung, cancer of the peritoneum, adrenal cancer, anal cancer, bile duct cancer, bladder cancer, brain cancer, breast cancer, triple negative breast cancer, central or peripheral nervous system cancers, cervical cancer, colon cancer, colorectal cancer, endometrial cancer, esophageal cancer, gall bladder cancer, gastrointestinal cancer, glioblastoma, head and neck cancer, kidney cancer, liver cancer, nasopharyngeal cancer, nasal cavity cancer, oropharyngeal cancer, oral cavity cancer, osteosarcoma, ovarian cancer, pancreatic cancer, parathyroid cancer, pituitary cancer, prostate cancer, retinoblastoma, sarcoma, salivary gland cancer, skin cancer, small intestine cancer, stomach cancer, testicular cancer, thymus cancer, thyroid cancer, uterine cancer, vaginal cancer and vulval cancer.

Administering the tumor cells to the genetically modified immunodeficient mouse can be any method that is suitable as recognized in the art. For example, administration can include administering cells into an organ, body cavity, or blood vessel such as by injection or implantation, such as subcutaneous and/or intraperitoneal implantation. The tumor cells may be administered as a tumor mass, clumps of tumor cells or as dissociated cells.

Tumor cells can be administered by various routes, such as, but not limited to, by subcutaneous injection, intraperitoneal injection or injection into the tail vein.

Engraftment of xenogeneic tumor cells can be assessed by any of various methods, such as, but not limited to, visual inspection of the mouse for signs of tumor formation.

Any of various methods can be used to measure growth of xenogeneic tumors, including but not limited to, measurement in living mice, measurement of tumors excised from living mice or measurement of tumors in situ or excised from dead mice. Measurements can be obtained using a measuring instrument such as a caliper, measurement using one or more imaging techniques such as ultrasonography, computed tomography, positron emission tomography, fluorescence imaging, bioluminescence imaging, magnetic resonance imaging and combinations of any two or more of these or other tumor measurement methods. The number of tumor cells in a sample obtained from a mouse bearing xenogeneic tumor cells can be used to measure tumor growth, particularly for non-solid tumors. For example, the number of non-solid tumor cells in a blood sample can be assessed to obtain a measurement of growth of a non-solid tumor in a mouse.

The number of tumor cells administered is not considered limiting. A single tumor cell can expand into a detectable tumor in the genetically modified immunodeficient animals described herein. The number of administered tumor cells is generally in the range of $10^3$ (1,000)-$1\times10^8$ (100,000,000), tumor cells, although more or fewer can be administered.

Thus, a method according to aspects of the present invention can include administering about $1\times10^2$ (100) to about $1\times10^8$ (100,000,000), about $1\times10^3$ (1,000) to about $1\times10^5$ (100,000), about $1\times10^4$ (10,000) to about $1\times10^6$ (1,000,000), about $1\times10^5$ (100,000) to about $1\times10^7$ (10,000,000), about $1\times10^3$ (1000) to about $1\times10^4$ (10,000), about $5\times10^3$ (5,000) to about $5\times10^4$ (50,000), about $1\times10^4$ (10,000) to about $1\times10^5$ (100,000), about $5\times10^4$ (50,000) to about $5\times10^5$ (500,000), about $1\times10^5$ (100,000) to about $1\times10^6$ (1,000,000), about $5\times10^5$ (500,000), to about $5\times10^6$ (5,000,000), about $1\times10^6$ (1,000,000) to about $1\times10^7$ (10,000,000), about $2\times10^4$ (20,000) to about $5\times10^5$ (500,000), or about $5\times10^4$ (50,000) to about $2\times10^5$ (200,000) xenogeneic tumor cells, such as human tumor cells, to the genetically modified immunodeficient mouse. The method can include administering at least about $1\times10^2$ (100), about $2\times10^2$ (200), about $3\times10^2$ (300), about $4\times10^2$ (400), about $5\times10^{22}$ (500), about $6\times10^2$ (600), about $7\times10^2$ (700), about $8\times10^2$ (800), about $9\times10^2$ (900), about $1\times10^3$ (1,000), about $2\times10^3$ (2,000), about $3\times10^3$ (3,000), about $4\times10^3$ (4000), about $5\times10^3$ (5,000), about $6\times10^3$ (6,000), about $7\times10^3$ (7,000), about $8\times10^3$ (8,000), about $9\times10^3$ (9,000), about $1\times10^4$ (10,000), about $2\times10^4$ (20,000), about $3\times10^4$ (30,000), about $4\times10^4$ (40,000), about $5\times10^4$ (50,000), about $6\times10^4$ (60,000), about $7\times10^4$ (70,000), about $8\times10^4$ (80,000), about $9\times10^4$ (90,000), about $1\times10^3$ (100,000), about $2\times10^5$ (200,000), about $3\times10^5$ (300,000), about $4\times10^8$ (400,000), about $5\times10^8$ (500,000), about $6\times10^8$ (600,000), about $7\times10^8$ (700,000), about $8\times10^5$ (800,000), about $9\times10^8$ (900,000), about $1\times10^6$ (1,000,000), about $2\times10^6$ (2,000,000), about $3\times10^6$ (3,000,000), about $4\times10^6$ (4,000,000), about $5\times10^6$ (5,000,000), about $6\times10^6$ (6,000,000), about $7\times10^6$ (7,000,000), about $8\times10^6$ (8,000,000), about $9\times10^6$ (9,000,000), or about $1\times10^7$ (10,000,000), xenogencic tumor cells, such as human tumor cells, to the immunodeficient QUAD mouse. The method can include administering about $1\times10^2$ (100), about $2\times10^2$ (200), about $3\times10^2$ (300), about $4\times10^2$ (400), about $5\times10^2$ (500), about $6\times10^2$ (600), about $7\times10^2$ (700), about $8\times10^2$ (800), about $9\times10^2$ (900), about $1\times10^3$ (1,000), about $2\times10^3$ (2,000), about $3\times10^3$ (3,000), about $4\times10^3$ (4,000), about $5\times10^3$ (5,000), about $6\times10^3$ (6,000), about $7\times10^3$ (7,000), about 8×10³ (8,000), about 9×10³ (9,000), about 1×10⁴ (10,000), about 2×10⁴ (20,000), about 3×10⁴ (30,000), about 4×10⁴ (40,000), about 5×10⁴ (50,000), about 6×10⁴ (60,000), about 7×10⁴ (70,000), about 8×10⁴ (80,000), about 9×10⁴ (90,000), about 1×10⁸ (100,000), about 2×10⁵ (200,000), about 3×10⁸ (300,000), about 4×10⁸ (400,000), about 5×10⁵ (500,000), about 6×10⁵ (600,000), about 7×10⁸ (700,000), about 8×10⁵ (800,000), about 9×10⁸ (900,000), about 1×10⁶ (1,000,000), about 2×10⁶ (2,000,000), about 3×10⁶ (3,000,000), about 4×10⁶ (4,000,000), about 5×10⁶ (5,000,000), about 6×10⁶ (6,000,000), about 7×10⁶ (7,000,000), about 8×10⁶ (8,000,000), about 9×10⁶ (9,000,000), about 1×10 (10,000,000), or about 1×10⁸ (100,000,000), xenogeneic tumor cells, such as human tumor cells, to the genetically modified immunodeficient mouse. Those of ordinary skill will be able to determine a number of xenogeneic tumor cells that should be administered to a specific mouse using no more than routine experimentation.

According to aspects of the present invention, xenogeneic tumor cells and xenogeneic leukocytes are administered to a genetically modified immunodeficient mouse. The xenogeneic tumor cells and xenogeneic leukocytes can be administered at the same time or at different times.

According to aspects of the present invention, the tumor cells are derived from the same species as the administered leukocytes. According to aspects, both the tumor cells and the leukocytes administered to a genetically modified immunodeficient mouse of the present invention are human cells.

According to aspects of the present invention, xenogeneic tumor cells and xenogeneic T cells are administered to a genetically modified immunodeficient mouse. The xenogeneic tumor cells and xenogeneic T cells can be administered at the same time or at different times.

According to aspects of the present invention, the tumor cells are derived from the same species as the administered T cells. According to aspects, both the tumor cells and the T cells administered to a genetically modified immunodeficient mouse of the present invention are human cells.

According to aspects of the present invention, xenogeneic tumor cells and xenogeneic PBMC are administered to a genetically modified immunodeficient mouse. The xenogeneic tumor cells and xenogeneic PBMC can be administered at the same time or at different times.

According to aspects of the present invention, the tumor cells are derived from the same species as the administered PBMC. According to aspects, both the tumor cells and the PBMC administered to a genetically modified immunodeficient mouse of the present invention are human cells.

Conditioning

Engraftment of xenogeneic cells in an immunodeficient genetically modified mouse according to aspects of the present invention includes "conditioning" of the immunodeficient genetically modified mouse prior to administration of the xenogeneic cells, for example by sub-lethal irradiation of the recipient animal with high frequency electromagnetic radiation, or gamma radiation, or treatment with a radiomimetic drug such as busulfan or nitrogen mustard. Conditioning is believed to reduce numbers of host immune cells, such as hematopoietic cells, and create appropriate microenvironmental factors for engraftment of xenogeneic immune cells, such as, but not limited to, leukocytes, T cells, PBMC or other cells, and/or create microenvironmental niches for engraftment of xenogeneic immune cells. Standard methods for conditioning are known in the art, such as described herein and in J. Hayakawa et ed., 2009, Stem Cells, 27(1): 175-182.

Methods are provided according to aspects of the present invention which include administration of xenogeneic immune cells, such as, but not limited to, leukocytes, T cells, PBMC or other cells, to an immunodeficient genetically modified mouse without "conditioning" the immunodeficient genetically modified mouse prior to administration of the xenogeneic immune cells, such as, but not limited to, leukocytes, T cells, PBMC, or other cells. Methods are provided according to aspects of the present invention which include administration of xenogeneic immune cells, such as, but not limited to, leukocytes, T cells, PBMC, or other cells, to an immunodeficient genetically modified mouse without "conditioning" by radiation or radiomimetic drugs of the immunodeficient genetically modified mouse prior to administration of the xenogeneic xenogeneic immune cells.

Assays

Methods of assaying an effect of a putative therapeutic agent are provided according to aspects of the present invention which include administering an amount of the putative therapeutic agent to a genetically modified immunodeficient mouse including allogeneic and/or xenogeneic cells or tissues; and measuring the effect of the putative therapeutic agent.

A putative therapeutic agent used in a method of the present invention can be any chemical entity, illustratively including a synthetic or naturally occurring compound or a combination of a synthetic or naturally occurring compound, a small organic or inorganic molecule, a protein, a peptide, a nucleic acid, a carbohydrate, an oligosaccharide, a lipid or a combination of any of these.

Standards suitable for assays are well-known in the art and the standard used can be any appropriate standard.

Assay results can be analyzed using statistical analysis by any of various methods, exemplified by parametric or non-parametric tests, analysis of variance, analysis of covariance, logistic regression for multivariate analysis, Fisher's exact test, the chi-square test, Student's T-test, the Mann-Whitney test, Wilcoxon signed ranks test, McNemar test, Friedman test and Page's L trend test. These and other statistical tests are well-known in the art as detailed in Hicks, C M, Research Methods for Clinical Therapists: Applied Project Design and Analysis, Churchill Livingstone (publisher); 5th Ed., 2009; and Freund, R J et al., Statistical Methods, Academic Press; 3rd Ed., 2010.

Methods and genetically modified immunodeficient mice provided according to aspects of the present invention have various utilities such as, in vivo testing of substances directed against human cancer.

Methods for identifying anti-tumor activity of a test substance according to aspects of the present invention include providing a genetically modified immunodeficient mouse; administering xenogeneic tumor cells to the genetically modified immunodeficient mouse, wherein the xenogeneic tumor cells form a solid or non-solid tumor in the genetically modified immunodeficient mouse; administering a test substance to the genetically modified immunodeficient mouse; assaying a response of the xenogeneic tumor and/or tumor cells to the test substance, wherein an inhibitory effect of the test substance on the tumor and/or tumor cells identifies the test substance as having anti-tumor activity.

Methods for identifying anti-tumor activity of a test substance according to aspects of the present invention include providing a genetically modified immunodeficient mouse, wherein the genetically modified immunodeficient mouse has engrafted xenogeneic PMBC; administering xenogeneic tumor cells to the genetically modified immunodeficient mouse, wherein the xenogeneic tumor cells form a solid or non-solid tumor in the genetically modified immunodeficient mouse; administering a test substance to the genetically modified immunodeficient mouse; assaying a response of the xenogeneic tumor and/or tumor cells to the test substance, wherein an inhibitory effect of the test substance on the tumor and/or tumor cells identifies the test substance as having anti-tumor activity.

Methods for identifying anti-tumor activity of a test substance according to aspects of the present invention include providing a genetically modified immunodeficient mouse, wherein the genetically modified immunodeficient mouse has engrafted human PBMC; administering human tumor cells to the genetically modified immunodeficient mouse, wherein the human tumor cells form a solid or non-solid tumor in the genetically modified immunodeficient mouse; administering a test substance to the genetically modified immunodeficient mouse; assaying a response of the human tumor and/or tumor cells to the test substance, wherein an inhibitory effect of the test substance on the tumor and/or tumor cells identifies the test substance as having anti-tumor activity.

A genetically modified immunodeficient mouse used in an assay for identifying anti-tumor activity of a test substance according to aspects of the present invention is an NSG-($K^b$ $D^b$)$^{null}$ ($IA^{null}$) mouse; or NSG-B2M$^{null}$ ($IA$ $IE^{null}$)) mouse.

The term "inhibitory effect" as used herein refers to an effect of the test substance to inhibit one or more of: tumor growth, tumor cell metabolism and tumor cell division.

Assaying a response of the xenogeneic tumor and/or tumor cells to the test substance includes comparing the response to a standard to determine the effect of the test substance on the xenogeneic tumor cells according to aspects of methods of the present invention, wherein an inhibitory effect of the test substance on the xenogeneic tumor cells identifies the test substance as an anti-tumor composition. Standards are well-known in the art and the standard used can be any appropriate standard. In one example, a standard is a compound known to have an anti-tumor effect. In a further example, non-treatment of a comparable xenogeneic tumor provides a base level indication of the tumor growth without treatment for comparison of the effect of a test substance. A standard may be a reference level of expected tumor growth previously determined in an individual comparable mouse or in a population of comparable mice and stored in a print or electronic medium for recall and comparison to an assay result.

Assay results can be analyzed using statistical analysis by any of various methods to determine whether the test substance has an inhibitory effect on a tumor, exemplified by parametric or non-parametric tests, analysis of variance, analysis of covariance, logistic regression for multivariate analysis, Fisher's exact test, the chi-square test, Student's T-test, the Mann-Whitney test, Wilcoxon signed ranks test, McNemar test, Friedman test and Page's L trend test. These and other statistical tests are well-known in the art as detailed in Hicks, C M, Research Methods for Clinical Therapists: Applied Project Design and Analysis, Churchill Livingstone (publisher); 5$^{th}$ Ed., 2009; and Freund, R J et al., Statistical Methods, Academic Press; 3$^{rd}$ Ed., 2010.

A test substance used in a method of the present invention can be any chemical entity, illustratively including a synthetic or naturally occurring compound or a combination of a synthetic or naturally occurring compound, a small organic or inorganic molecule, an antibody (murine, chimeric or humanized), an antibody fragment (Fab, F(ab)'2), a protein, a peptide, a nucleic acid, a carbohydrate, an oligosaccharide, a lipid or a combination of any of these.

According to aspects of the present invention, the test substance is an immunotherapeutic agent, such as an antibody (murine, chimeric or humanized), an antibody fragment (Fab, F(ab)'2) or a combination of any of these, or non-immunotherapeutic agent such as a synthetic or naturally occurring compound, a combination of a synthetic or naturally occurring compound, a small organic or inorganic molecule, a protein or a peptide which is not an antibody or antigen binding fragment, a nucleic acid, a carbohydrate, an oligosaccharide, a lipid or a combination of any of these.

According to aspects of the present invention, a test substance is an anti cancer agent. According to aspects of the present invention, the anti-cancer agent is an anti-cancer immunotherapeutic agent, such as an anti-cancer antibody or antigen binding fragment thereof. According to aspects of the present invention, the anti-cancer agent is a non-immunotherapeutic agent such as a synthetic or naturally occurring compound, a combination of a synthetic or naturally occurring compound, a small organic or inorganic molecule, a protein or a peptide which is not an antibody or antigen binding fragment, a nucleic acid, a carbohydrate, an oligosaccharide, a lipid or a combination of any of these.

Anti-cancer agents are described, for example, in Brunton et al., (eds.), Goodman and Gilman's The Pharmacological Basis of Therapeutics, 12$^{th}$ Ed., Macmillan Publishing Co., 2011.

Anti-cancer agents illustratively include acivicin, aclarubicin, acodazole, acronine, adozelesin, aldesleukin, alitretinoin, allopurinol, altretamine, ambomycin, ametantrone, amifostine, aminoglutethimide, amsacrine, anastrozole, anthramycin, arsenic trioxide, asparaginase, asperlin, azacitidine, azetepa, azotomycin, batimastat, benzodepa, bicalutamide, bisantrene, bisnafide dimesylate, bizelesin, bleomycin, brequinar, bropirimine, busulfan, cactinomycin, calusterone, capecitabine, caracemide, carbetimer, carboplatin, carmustine, carubicin, carzelesin, cedefingol, celecoxib, chlorambucil, cirolemycin, cisplatin, cladribine, cobimetinib, crisnatol mesylate, cyclophosphamide, cytarabine, dacarbazine, dactinomycin, daunorubicin, decitabine, dexormaplatin, dezaguanine, dezaguanine mesylate, diaziquone, docetaxel, doxorubicin, droloxifene, dromostanolone, duazomycin, edatrexate, eflornithine, elsamitrucin, enloplatin, enpromate, epipropidine, epirubicin, erbulozole, esorubicin, estramustine, etanidazole, etoposide, etoprine, fadrozole, fazarabine, fenretinide, floxuridine, fludarabine, fluorouracil, flurocitabine, fosquidone, fostriecin, fulvestrant, gemcitabine, hydroxyurea, idarubicin, ifosfamide, ilmofosine, interleukin II (IL-2, including recombinant interleukin II or rIL2), interferon alfa-2a, interferon alfa-2b, interferon alfa-n1, interferon alfa-n3, interferon beta-Ia, interferon gamma-Ib, iproplatin, irinotecan, lanreotide, letrozole, leuprolide, liarozole, lometrexol, lomustine, losoxantrone, masoprocol, maytansine, mechlorethamine hydrochlride, megestrol, melengestrol acetate, melphalan, menogaril, mercaptopurine, methotrexate, metoprine, meturedepa, mitindomide, mitocarcin, mitocromin, mitogillin, mitomalcin, mitomycin, mitosper, mitotane, mitoxantrone, mycophenolic acid, nelarabine, nocodazole, nogalamycin, ormnaplatin, oxisuran, paclitaxel, pegaspargase, peliomycin, pentamustine, peplomycin, perfosfamide, pipobroman, piposulfan, piroxantrone hydrochloride, plicamycin, plomestane, porfimer, porfiromycin, prednimustine, procarbazine, puromycin, pyrazofurin, riboprine, rogletimide, safingol, semustine, simtrazene, sparfosate, sparsomycin, spirogermanium, spiromustine, spiroplatin, streptonigrin, streptozocin, sulofenur, talisomycin, tamoxifen, tecogalan, tegafur, teloxantrone, temoporfin, teniposide, teroxirone, testolactone, thiamiprine, thioguanine, thiotepa, tiazofurin, tirapazamine, topotecan, toremifene, trestolone, triciribine, trimetrexate, triptorelin, tubulozole, uracil mustard, uredepa, vapreotide, vemurafenib, verteporfin, vinblastine, vincristine sulfate, vindesine, vinepidine, vinglycinate, vinleurosine, vinorelbine, vinrosidine, vinzolidine, vorozole, zeniplatin, zinostatin, zoledronate, zorubicin, and the like.

According to aspects of the present invention, an anti-cancer agent is an anti-cancer immunotherapeutic agent, also called an anti-cancer antibody. An anti-cancer immunotherapeutic agent used can be any antibody, or effective portion of an antibody, effective to inhibit at least one type of tumor, particularly a human tumor. Anti-cancer immunotherapeutic agents include, but are not limited to, 3F8, 8H9, abagovomab, abituzumab, adalimumab, adecatumumab, aducanumab, afutuzumab, alacizumab pegol, alemtuzumab, amatuximab, anatumomab mafenatox, anetumab ravtansine, apolizumab, arcitumomab, ascrinvacumab, atezolizumab, bavituximab, belimumab, bevacizumab, bivatuzumab mertansine, brentuximab vedotin, brontictuzumab, cantuzumab mertansine, cantuzumab ravtansine, capromab pendetide, catumaxomab, cetuximab, citatuzumab bogatox, cixutumumab, clivatuzumab tetraxetan, coltuximab ravtansine, conatumumab, dacetuzumab, dalotuzumab, demcizumab, denintuzumab mafodotin, depatuxizumab mafodotin, durvalumab, dusigitumab, edrecolomab, elotuzumab, emactuzumab, emibetuzumab, enoblituzumab, enfortumab vedotin, enavatuzumab, epratuzumab, ertumaxomab, etaracizumab, farletuzumab, ficlatuzumab, figitumumab, flanvotumab, futuximab, galiximab, ganitumab, gemtuzumab, girentuximab, glembatumumab vedotin, ibritumomab tiuxetan, igovomab, imab362, imalumab, imgatuzumab, indatuximab ravtansine, indusatumab vedotin, inebilizumab, inotuzumab ozogamicin, intetumumab, ipilimumab, iratumumab, isatuximab, labetuzumab, lexatumumab, lifastuzumab vedotin, lintuzumab, lirilumab, lorvotuzumab mertansine, lucatumumab, lumiliximab, lumretuzumab, mapatumumab, margetuximab, matuzumab, milatuzumab, mirvetuximab soravtansine, mitumomab, mogamulizumab, moxetumomab pasudotox, nacolomab tafenatox, naptumomab estafenatox, narnatumab, necitumumab, nesvacumab, nimotuzumab, nivolumab, ocaratuzumab, ofatumumab, olaratumab, onartuzumab, ontuxizumab, oregovomab, oportuzumab monatox, otlertuzumab, panitumumab, pankomab, parsatuzumab, patritumab, pembrolizumab, pemtumomab, pertuzumab, pidilizumab, pinatuzumab vedotin, polatuzumab vedotin, pritumumab, racotumomab, radretumab, ramucirumab, rilotumumab, rituximab, robatumumab, sacituzumab govitecan, samalizumab, seribantumab, sibrotuzumab, siltuximab, sofituzumab vedotin, tacatuzumab tetraxetan, tarextumab, tenatumomab, teprotumumab, tetulomab, tigatuzumab, tositumomab, tovetumab, trastuzumab, tremelimumab, tucotuzumab celmoleukin, ublituximab, utomilumab, vandortuzumab vedotin, vantictumab, vanucizumab, varlilumab, vesencumab, volociximab, vorsetuzumab mafodotin, votumumab, zalutumumab, zatuximab, and the like.

According to aspects of the present invention, a test substance is one that specifically binds one or more of: 1) a cell-surface protein such as a cluster of differentiation (CD) cell-surface molecule; 2) an intracellular protein such as a kinase; and 3) an extracellular protein such as a shed cell-surface receptor or the soluble ligand of a cell-surface receptor.

According to aspects of the present invention, a test substance is one that specifically binds a protein that is expressed by leukocytes (e.g., lymphocytes or myeloid-lineage leukocytes). In a further option, a test substance is one that specifically binds a ligand of a leukocyte. In a still further option, a test substance is one that specifically binds a molecule that is expressed by a cancer cell.

According to aspects of the present invention, a test substance can specifically bind PD-1, PD-L1, or CTLA-4. According to aspects of the present invention, a test substance can be an immune checkpoint inhibitor such as a PD-1 inhibitor, PD-L1 inhibitor, or CTLA-4 inhibitor. According to aspects of the present invention, an immune checkpoint inhibitor is an antibody that specifically binds to PD-1, PD-L1, or CTLA-4 and is a PD-1 inhibitor, PD-L1 inhibitor, or CTLA-4 inhibitor, respectively. According to aspects of the present invention, a test substance is an immune checkpoint inhibitor selected from atezolizumab, avelumab, durvalumab, ipilimumab, nivolumab, pembrolizumab, and an antigen-binding fragment of any one of the foregoing.

The test substance can be administered by any suitable route of administration, such as, but not limited to, oral, rectal, buccal, nasal, intramuscular, vaginal, ocular, otic, subcutaneous, transdermal, intratumoral, intravenous, and intraperitoneal.

Embodiments of inventive compositions and methods are illustrated in the following examples. These examples are provided for illustrative purposes and are not considered limitations on the scope of inventive compositions and methods.

EXAMPLES

Mice

All mice used in these studies were raised in breeding colonies at the Jackson Laboratory. NOD.Cg-Prkdc$^{scid}$ Il2rg$^{tm1Wjl}$/SzJ.(NOD-scid-IL2r$\gamma^{null}$, NSG) mice have been described previously in Shultz L D, et al., 2005, J Immunol 174:6477-6489.

NSG mice were maintained through sib matings. NOD.Cg-Prkdc$^{scid}$ H2-K1$^{tm1Bpe}$ H2-Ab1$^{em1Mvw}$ H2-D1$^{tm1Bpe}$ Il2rg$^{tm1Wjl}$/SzJ (abbreviated as NSG-(NSG-K$^b$ D$^b)^{null}$ (IA$^{null}$)) mice were developed using TALEN. Exon 2 of the H2-Ab1 gene was targeted in NOD.Cg-Prkdc$^{scid}$ H2-K1$^{tm1Bpe}$ H2-D1$^{tm1Bpe}$ Il2rg$^{tm1Wjl}$/SzJ (abbreviated as NSG-(K$^b$ D$^b)^{null}$, see Covassin L, et al., 2013, Clin Exp Immunol 174:372-388) embryos. The offspring carrying the null IA$^b$ allele (H2-Ab1$^{em1Mvw}$) were identified by PCR and the null IA$^b$ allele was fixed to homozygosity. NSG-(K$^b$ D$^b)^{null}$ (IA$^{null}$) mice are maintained through homozygous sib mating.

NOD.Cg-B2m$^{tm1Une}$ Prkdc$^{scid}$ H2$^{dlAb1-Ea}$ Il2rg$^{tm1Wjl}$/SzJ (abbreviated as NSG-B2M$^{null}$ (IA IE)$^{null}$ were made by intercrossing NOD.Cg-B2m$^{tm1Une}$ Prkdc$^{scid}$ Il2rg$^{tm1Wjl}$/SzJ (abbreviated as NSG-B2M$^{null}$) mice (see King M A, et al., 2009, Clin Exp Immunol 157:104-118) with NOD.Cg-Prkdc$^{scid}$H2$^{dlAb1-Ea}$ Il2rg$^{tm1Wjl}$/SzJ (see Madsen L, et al., 1999, Proc Natl Acad Sci USA 96:10338-10343) and intercrossing the F1 progeny followed by selecting the NSG mice doubly homozygous for the B2m$^{tm1Une}$ and H2$^{dlAb1-Ea}$ alleles. The NSG-B2M$^{null}$ (IA IE$^{null}$) mice were maintained through sib mating.

To create the NOD.Cg-Prkdc$^{scid}$ H2-K1$^{tm1Bpe}$ H2-Ab1$^{em1Mvw}$ H2-D1$^{tm1Bpe}$ Il2rg$^{tm1Wjl}$ Tg(Ins2-HBEGF) 6832Ugfm/Sz transgene, abbreviated as the NSG-RIP-DTR (K$^b$ D$^b)^{null}$ (IA$^{null}$) strain, the Tg(Ins2-HBEGF)68321Ugfm, abbreviated as RIP-DTR transgene, was backcrossed onto the NSG strain (Dai C, et al., 2016, J Clin Invest 126:1857-1870; and Yang C, et al., 2015. Diabetes Metab Syndr Obes 8:387-398) and then crossed the NSG-DTR strain with the NSG-($K^b$ $D^b$)$^{null}$ (IA$^{null}$) strain to create the NSG-RIP-DTR ($K^d$ $D^b$)$^{null}$ (IA$^{null}$) strain. These mice are maintained by sib mating of mice homozygous for the disrupted alleles and for the transgene.

All animals were housed in a specific pathogen free facility in microisolator cages, given autoclaved food and maintained on acidified autoclaved water at The Jackson Laboratory or alternated weekly between acidified autoclaved water and sulfamethoxazole-trimethoprim medicated water (Goldline Laboratories, Ft. Lauderdale, Fla.) at the University of Massachusetts Medical School.

Antibodies and Flow Cytometry

The phenotypes of murine cells in the NSG MHC knockout mice were determined as described in detail in Shultz L D, et al., 2005, J Immunol 174:6477-6489. Anti-murine monoclonal antibodies (mAb) were purchased as FITC, PE, APC, or PerCP conjugates in order to accommodate four-color flow cytometric analysis. Immune competent NOD/ShiLtJ (NOD) and C57BL/6 (B6) mice were run with each experiment to ensure correct MHC staining. The B6 mice were included to control for carryover of the linked MHC II gene region adjacent to the classically knocked out Ea genes, which was made in 129 embryonic stem cells and back-crossed to NSG to make NSG-B2M$^{null}$ (IA IE$^{null}$) mice. Spleens were snipped into small pieces in 1 mL of 200 U/ml Collagenase D in DMEM without serum on ice. Two additional nil of Collagenase D solution were added and the spleens were vortexed. They were incubated in a 37° C. water bath for 30 minutes with occasional vortexing and mixing. The cells were washed and suspended in Geys RBC lysing buffer, mixed and incubated 1 minute on ice. Cells were washed with FACS buffer and stained for 30 minutes at 4° C., washed twice with FACS buffer, suspended in 250 μls of FACS buffer and stained with propidium iodide, and 100,000 events were then analyzed on a BD Biosciences LSR II flow cytometer. Anti-mouse antibodies used were anti-H2Kb (clone AF6-885), H2Kd (SF1-1.1), CD11b (M1/70), CD11c (N418), I-Ab,d IEk,d (M5/114), Ly6G (1A8), Ly6c (HK1.4), and I-Ag7 (10-2.16).

Human immune cell populations were monitored in PBMC-engrafted mice using mAbs specific for the following human antigens; CD45 (clone HI30), CD3 (clone UCHT1), CD4 (clone RPA-T4), CD8 (clone RPA-T8), CD20 (clone 2H7) CD45RA (clone HI100), CCR7 (clone G043H7), PD1 (clone EH12.2H7) and granzyme B (clone GB11) purchased from eBioscience, BD Bioscience (San Jose, Calif.) or BioLegend (San Diego, Calif.). Mouse cells were identified and excluded from analysis by staining with a mAb specific for murine CD45 (clone 30-F11, BD Biosciences).

Single-cell suspensions of spleen were prepared from engrafted mice, and whole blood was collected in heparin. Single cell suspensions of 1×10$^6$ cells or 100 μl of whole blood were washed with FACS buffer (PBS supplemented with 2% fetal bovine serum (FBS) and 0.02% sodium azide) and then pre-incubated with rat anti-mouse FcR11b mAb (clone 2.4G2, BD Biosciences) to block binding to mouse Fc receptors. Specific mAbs were then added to the samples and incubated for 30 min at 4° C. Stained samples were washed and fixed with 2% paraformaldehyde for cell suspensions or treated with BD FACS lysing solution for whole blood. At least 50,000 events were acquired on LSRII or FACSCalibur instruments (BD Biosciences). For human cell phenotyping, mouse cells were identified and excluded from analysis by staining with a mAb specific for murine CD45 (clone 30-F11, BD Biosciences). Data analysis was performed with FlowJo (Tree Star, Inc., Ashland, Oreg.) software.

Collection of Human Peripheral Blood Mononuclear Cells (PBMC)

Human PBMCs were obtained from healthy volunteers. PBMCs were collected in heparin and purified by Ficoll-hypaque density centrifugation and suspended in RPMI for injection into mice at the cell doses indicated. In some experiments pheresis leukopaks were obtained from the Blood Bank at the University of Massachusetts Medical Center as anonymous discarded units.

GVHD Protocol

Mice were injected intraperitoneally with various doses of PBMC. Mice were weighed 2 to 3 times weekly and the appearance of GVHD-like symptoms including weight loss (>20%), hunched posture, ruffled fur, reduced mobility, and tachypnea were used to determine time of euthanasia and is indicated as time of survival.

Human Islet Transplantation

Human islets designated for research were obtained from Prodo Laboratories, Inc. (Irvine, Calif.). Human IEQ (4000) were transplanted into the spleen of NSG-RIP-DZR ($K^b$ $D^b$)$^{null}$ (IA) mice. NSG-RIP-UTR ($K^b$ $D^b$)$^{null}$ (IA$^{null}$) mice were treated with 40 ng diphtheria toxin 2-4 days prior to islet transplantation. Hyperglycemia (>400 mg/dl) was confirmed using an Accu-Chek Active glucometer (Hoffmann-La Roche, Basel, Switzerland). Blood glucose levels were then determined at twice-weekly intervals following transplantation to monitor islet graft function. C-peptide levels were detected in plasma using an ELISA kit specific for human C-peptide (Alpco, Salem, N.H.). Total insulin content within transplanted spleens was determined as previously described (Harlan D M, et al., 1995, Diabetes, 44:816-823) using an ELISA kit specific for human insulin (Alpco, Salem, N.H.).

dsAAV Vectors

The dsAAV vectors were engineered and packaged as previously described He Y, et al., 2013, Hum. Gene Ther., 24:545-553).

Briefly, full-length cDNA encoding human IL2 or EGFP was subcloned into a dsAAV plasmid (McCarty D M, et al., 2001, Gene Ther 8:1248-1254) containing the marine pre-proinsulin II promoter (mIP). dsAAV vector packaging was carried out as previously described (Grieger J C, et al., 2006, Nat Protoc 1:1412-1428; and Johnson M C, et al., 2013, Diabetes 62:3775-3784) or produced by the Viral Vector Core at the University of Massachusetts Medical School Horae Gene Therapy Center (Worcester, Mass.). Recipient mice were injected IP with 2.5×10$^{11}$ particles of the purified AAV8-huIL2 (AAV-IL2).

Statistical Analyses

To compare individual pair-wise groupings, one-way ANOVA or 2-way ANOVA with Bonferroni post-tests and Kruskal-Wallis test with Dunns post-test were used for parametric and non-parametric data, respectively. Significant differences were assumed for p values<0.05. Statistical analyses were performed using GraphPad Prism software (version 4.0c, GraphPad, San Diego, Calif.).

Results

Phenotypic Characterization of NSG and Two Strains of NSG MHC Class I/II Double Knockout Mice.

Figure 1B:
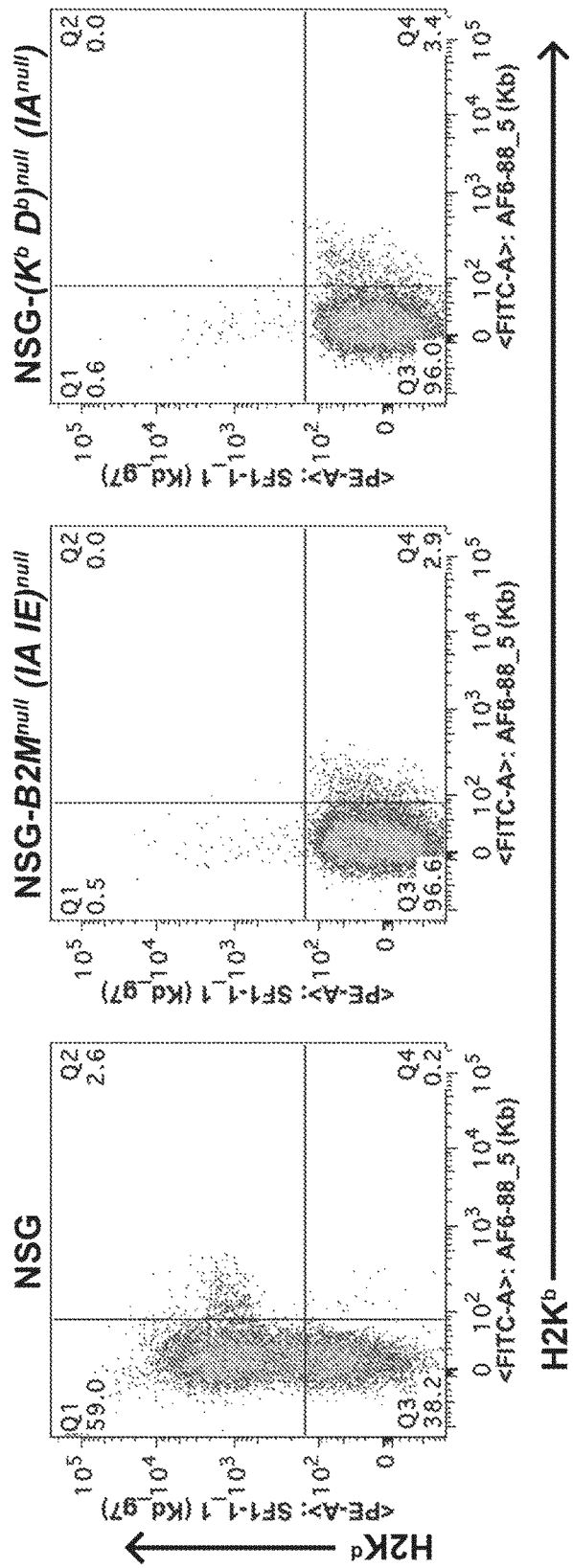
Figure 1C:
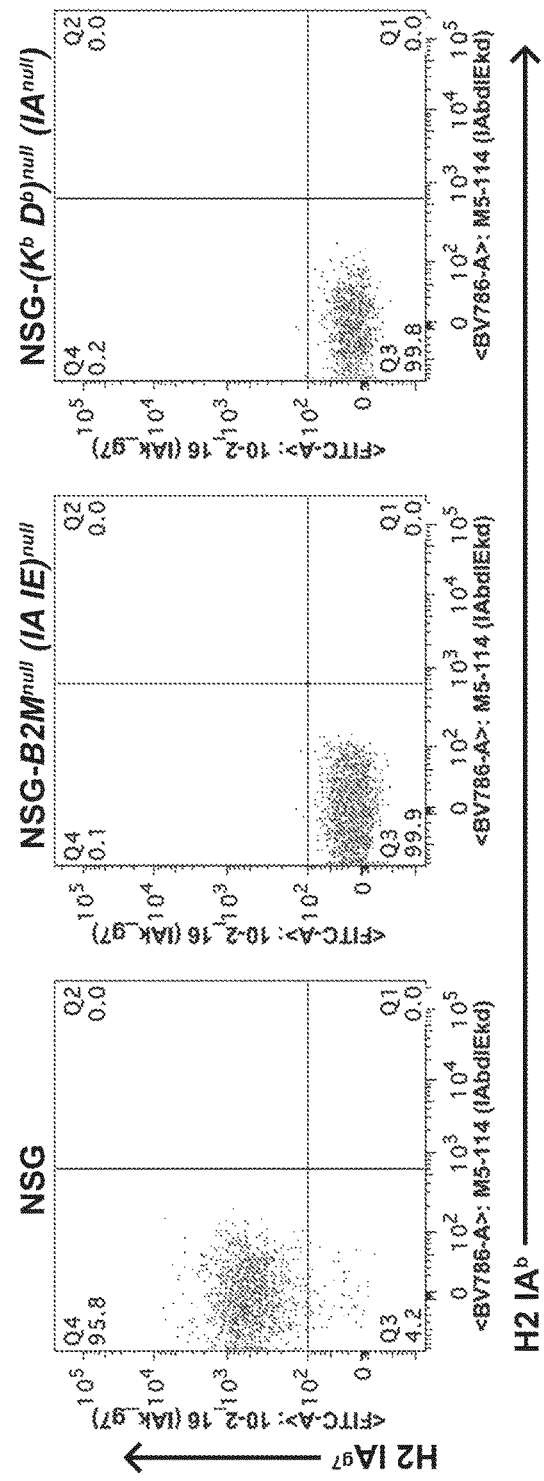

Two NSG mouse strains that are doubly deficient in MHC class I and class H were created, the NSG-($K^b$ $D^b$)$^{null}$ (IA$^{null}$) and NSG-B2M$^{null}$ (IA IE)$^{null}$ knockout strains. The absence of MHC class I and class H in both strains was confirmed by flow cytometry (FIG. 1). Due to absence of immune cells that express readily detectable levels of mouse MHC II, spleens were enzymatically disaggregated and gated to analyze the dendritic cell population. FIG. 1A demonstrates the gating strategy of excluding doublets and dead cells and proceeds to gate on monocyte derived dendritic cells (CD11b+ Ly6c$^{dim}$ CD11c+). The NSG mouse demonstrates the expected staining pattern of H2K$^d$ positive, H2K$^b$ negative for MHC class I (FIG. 1B), and I-A$^{g7}$ positive, I-A$^b$ negative for MHC class II (FIG. 1C). The NSG-(K$^b$ D$^b$)$^{null}$ (IA$^{null}$) and NSG-B2M$^{null}$ (IA IE)$^{null}$ knockout mice both lack MHC class I and II molecules normally expressed by NOD and C57BL/6 mice.

Figure 2:
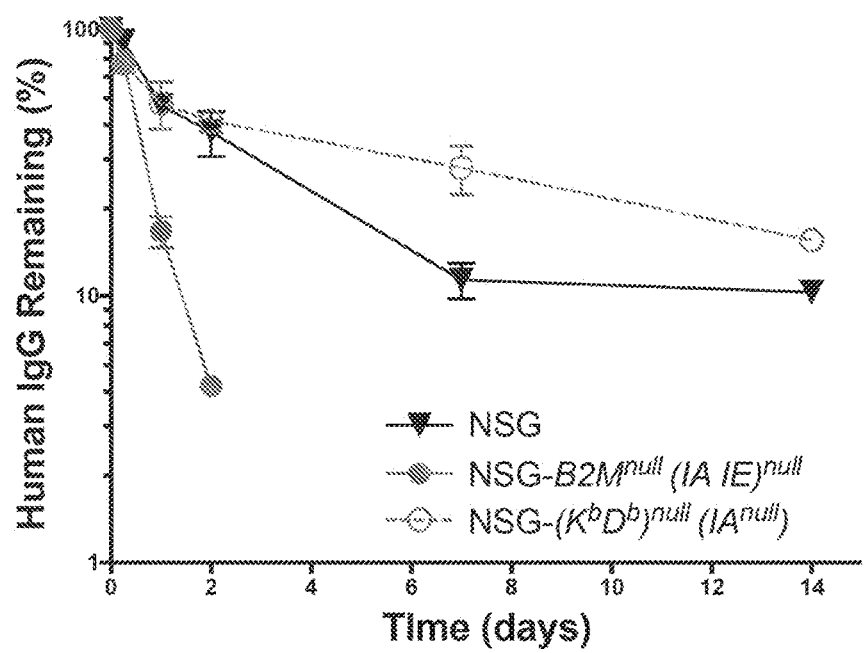
FIG. 2 is a graph showing human IgG half-life in the serum of NSG-(K$^b$D$^b)^{null}$ (IA$^{null}$) and NSG-B2M$^{null}$ (IA IE)$^{null}$ mice. Mice were injected IV with 200 µg of human IgG and bled at the indicated time points to recover serum. Serum was used for ELISA analysis of circulating human IgG. The first bleed at 2 minutes post-injection was considered as 100% serum IgG. Each point represents the mean±standard error of IgG in 5 males who were 2-3 months of age.

Due to the requirement of B2M for appropriate expression of murine FcRn, the receptor responsible for prolonging the half-life of IgG in the circulation, the clearance of human IgG in both stocks of mice was compared. Mice were injected IV with 200 µg of human IgG and bled at intervals for ELISA analysis of circulating human IgG. The first bleed at 2 minutes post-injection was considered as 100% serum IgG. Rapid clearance of human IgG in NSG-B2M$^{null}$ (IA IE)$^{null}$ mice was observed whereas IgG clearance in NSG-(K$^b$ D$^b$)$^{null}$ (IA$^{null}$) mice was similar to that observed in NSG mice (FIG. 2).

Figure 3A:
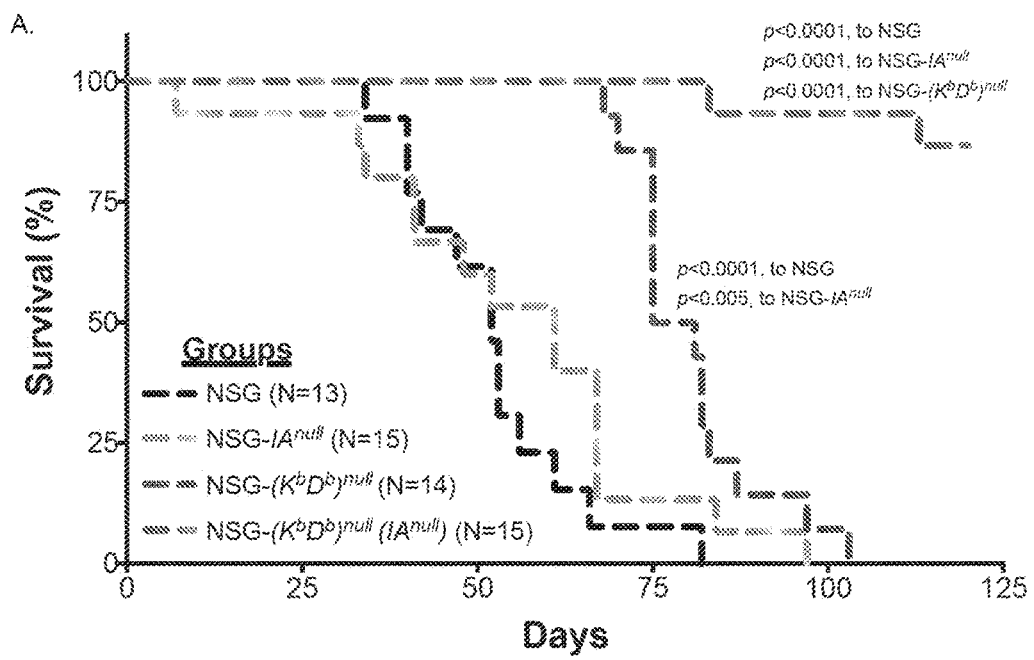
FIGS. 3A and 3B show survival of NSG mice lacking the expression of both mouse MHC class I and II following injection of Human Peripheral Blood Mononuclear Cells (PBMC). Recipient mice were injected intravenously (IV) with 10×10$^6$ PBMC, and mice were monitored for overall health and survival.

Survival of PBMC-Engrafted NSG and NSG-MHC Class I Knockout, NSG-MHC Class II Knockout, and NSG-MHC I/II Knockout Mice NSG-(K$^b$ D$^b$)$^{null}$ (IA$^{null}$):

To determine whether the absence of mouse MHC class I and II altered the incidence and kinetics of xenogeneic GVHD following human PBMC engraftment in NSG MHC I/II knockout mice, NSG strains deficient in MHC class I, MHC class II or the two NSG double knockout strains were engrafted with 10×10$^6$ PBMC and their survival was compared to that of NSG mice. As previously reported, NSG and NSG-(IA$^{null}$) showed relatively similar short survival, similar to that observed in NSG mice. In contrast, as expected, NSG-(K$^b$ D$^b$)$^{null}$ mice had an extended period of survival as compared to NSG mice. However, when both MHC class I and class II were knocked-out in NSG-(K$^b$ D$^b$)$^{null}$ (IA$^{null}$) mice, survival was past 100 days, and 13 of 15 of these MHC I/II knockout mice still alive at the end of the observation period (125 days) with no symptoms of GVHD, (FIG. 3A).

Figure 3B:
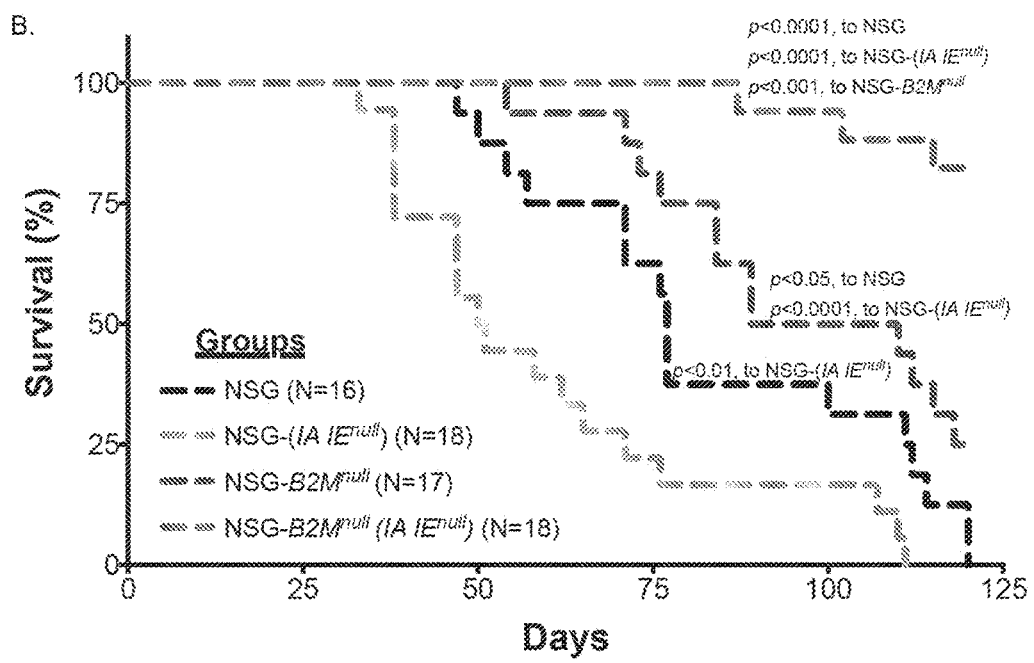

NSG-B2M$^{null}$ (IA IE$^{null}$):

Similar extended survival results were observed in PBMC-engrafted NSG-B2M$^{null}$ (IA IE$^{null}$) mice. For this MHC I/II knockout strain, the NSG-B2M$^{null}$ strain was used as the control rather than the NSG-(K$^b$ D$^b$)$^{null}$ strain. Again, NSG and NSG-(IA$^{null}$) knockout mice had relatively short survival. Survival of NSG-B2M$^{null}$ mice was significantly increased. As observed in NSG-(K$^b$ D$^b$)$^{null}$ (IA$^{null}$) mice, long term survival of the NSG-B2M$^{null}$ (IA IE$^{null}$) strain was achieved, with 15 of 18 surviving to the termination of the experiment (125 days) with no symptoms of GVHD (FIG. 3B).

Human Cell Chimerism in PBMC-Engrafted NSG and NSG-MHC Class I Knockout, NSG-MHC Class II Knockout, and NSG-MHC I/II Knockout Mice The long term survival of PBMC-engrafted NSG MHC I/II knockout mice could be the result of either a lack of human cell engraftment or a lack of GVHD due to the absence of MHC class I and II. To distinguish between these two possibilities, 10×10$^6$ PBMC were injected IP into both NSG MHC I/II knockout strains and the levels of CD45+ cells in the circulation over time was compared with that of NSG, NSG-class I knockout and MHC class II knockout mice.

Figure 4A:
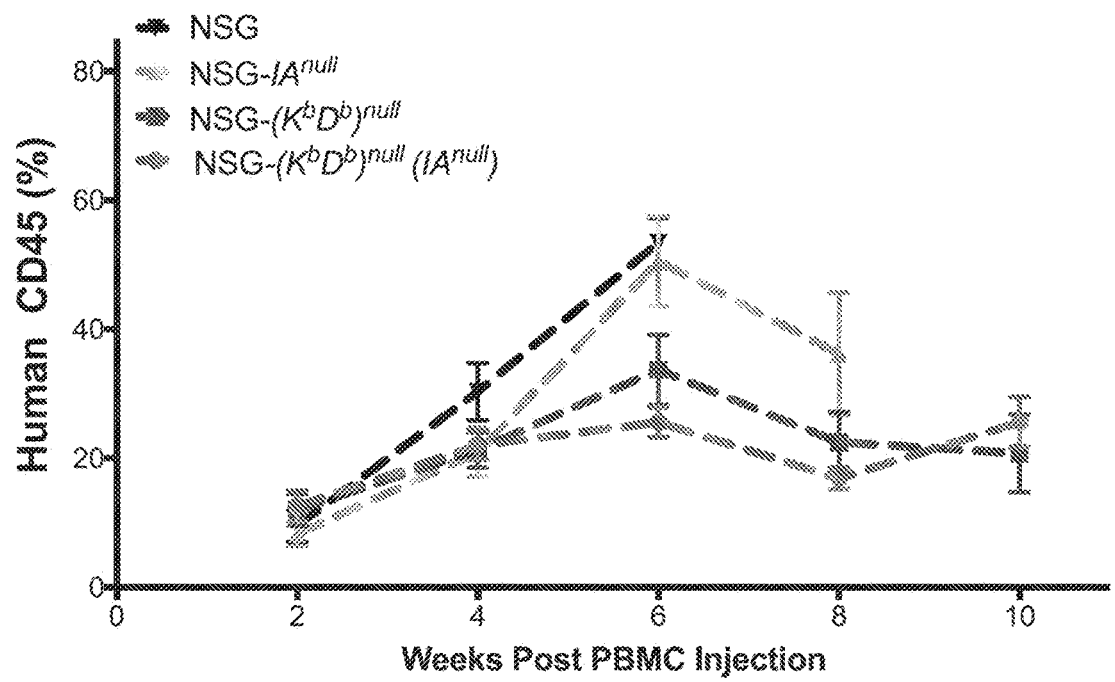
FIGS. 4A-4D show human CD45+ cell chimerism levels in NSG mice lacking the expression of both mouse MHC class I and II following injection of PBMC. Recipient mice were injected IV with 10×10$^6$ PBMC, and mice were monitored for levels of human cell chimerism by determining the proportion of human CD45+ cells in the peripheral blood (FIG. 4A and FIG. 4C) and spleen (FIG. 4B and FIG. 4D).
Figure 4B:
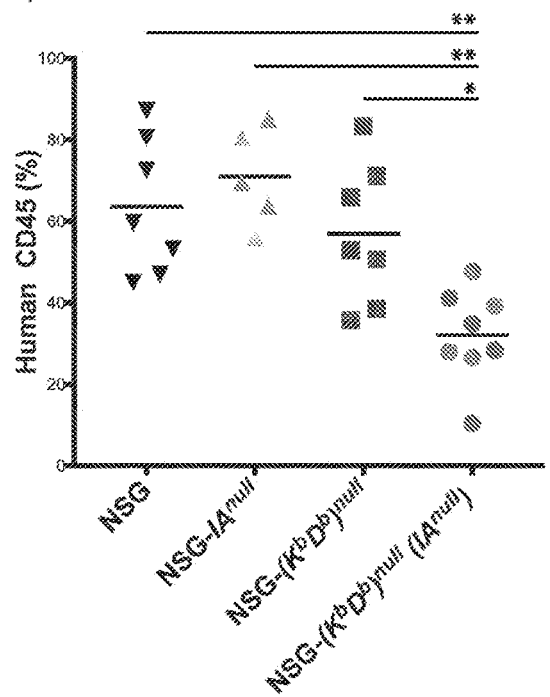

NSG-(K$^b$ D$^b$)$^{null}$ (IA$^{null}$) Mice:

human CD45 cell engraftment increased rapidly in NSG mice and NSG-(IA$^{null}$) mice (FIG. 4A). The percentages of circulating human CD45+ cells over time were lower in NSG-(K$^b$ D$^b$)$^{null}$ and NSG-(K$^b$ D$^b$)$^{null}$ (IA$^{null}$) mice as compared to NSG and NSG-(IA$^{null}$) mice. In the spleen, the percentages of human CD45+ cells in NSG-(IA$^{null}$) and NSG-(K$^b$ D$^b$)$^{null}$ mice were comparable to that observed in NSG mice, but the percentages of human CD45+ cells in the spleen of NSG-(K$^b$ D$^b$)$^{null}$ (IA$^{null}$) mice were significantly decreased (FIG. 4B).

Figure 4C:
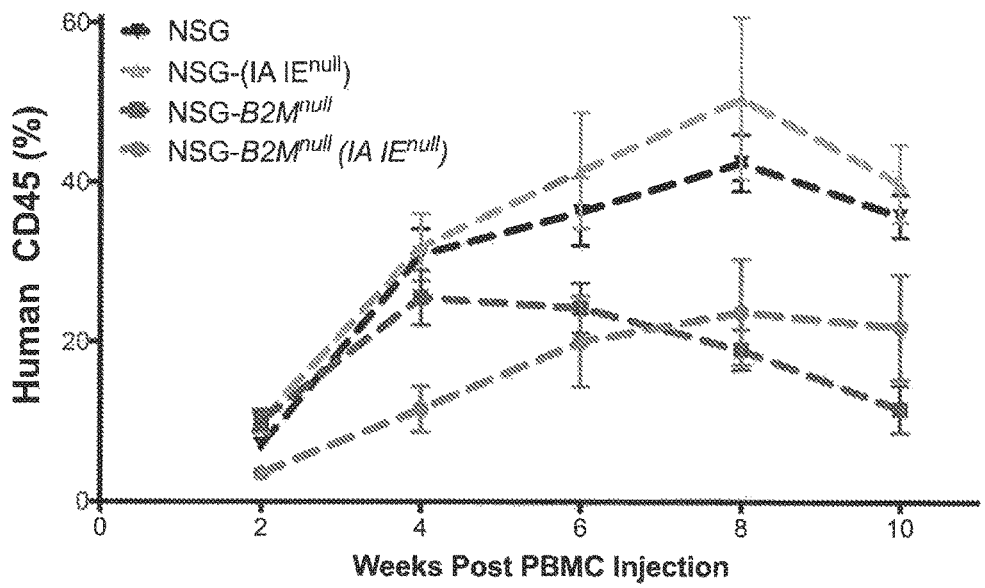
Figure 4D:
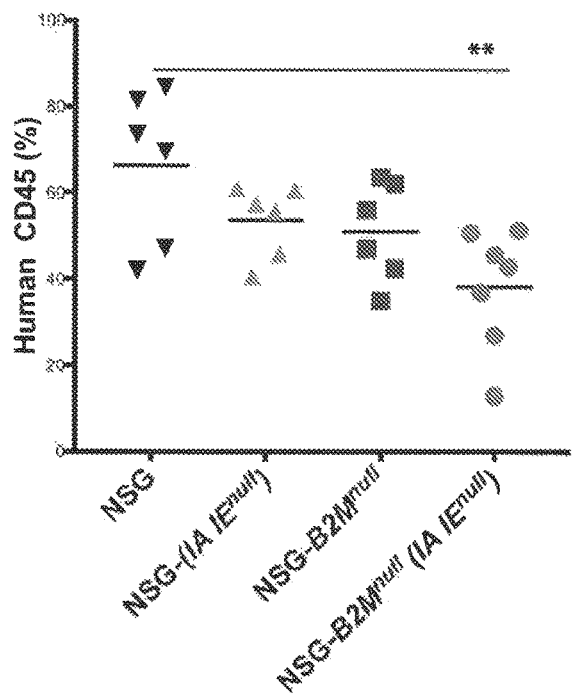

NSG-B2M$^{null}$ (IA IE)$^{null}$ Mice:

The NSG-B2M$^{null}$ strain was used as the NSG MHC class I knockout (KO) control. As observed in the NSG, NSG-(IA$^{null}$) mice, NSG-(K$^b$ D$^b$)$^{null}$ and NSG-(K$^b$ D$^b$)$^{null}$ (IA$^{null}$) mice, the percentages of circulating human CD45+ cells were higher in the NSG and NSG-(IA$^{null}$) mice as compared to that observed in NSG-B2M$^{null}$ and NSG-B2M$^{null}$ (IA IE$^{null}$) mice (FIG. 4C). The percentages of human CD45+ cells in the spleen of NSG-B2M$^{null}$ (IA IE$^{null}$) mice were significantly lower than in the other three strains (FIG. 4D).

Figure 5A:
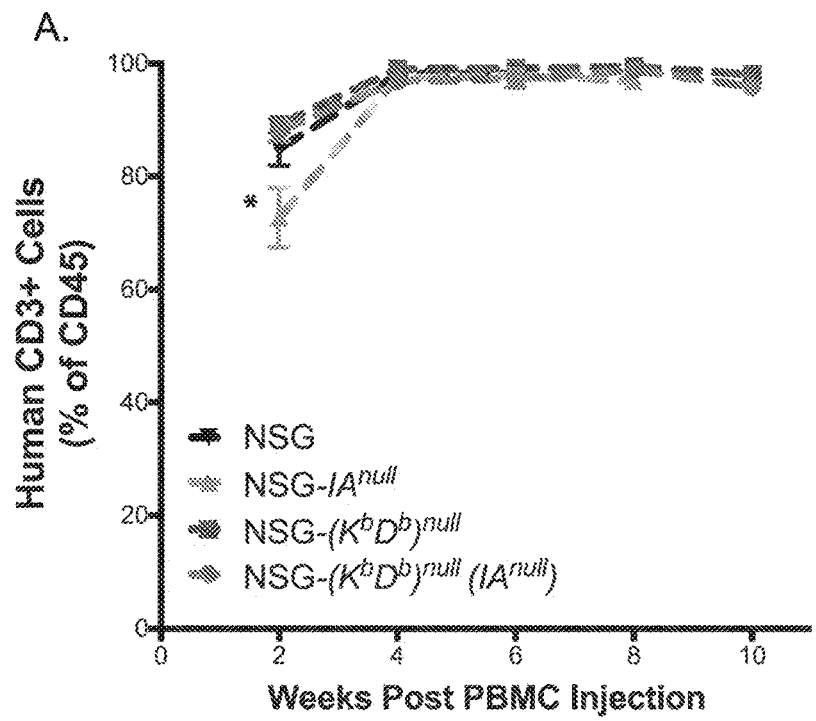
FIGS. 5A-5D show engraftment of human T cells and B cells in NSG mice lacking the expression of both mouse MHC class I and II following injection of PBMC. Recipient mice were injected IV with 10×10$^6$ PBMC, and mice were monitored for levels of human CD3+ T cells (FIG. 5A and FIG. 5C) and CD20+ B cells (FIG. 5B and FIG. 5D) in peripheral blood.
Figure 5B:
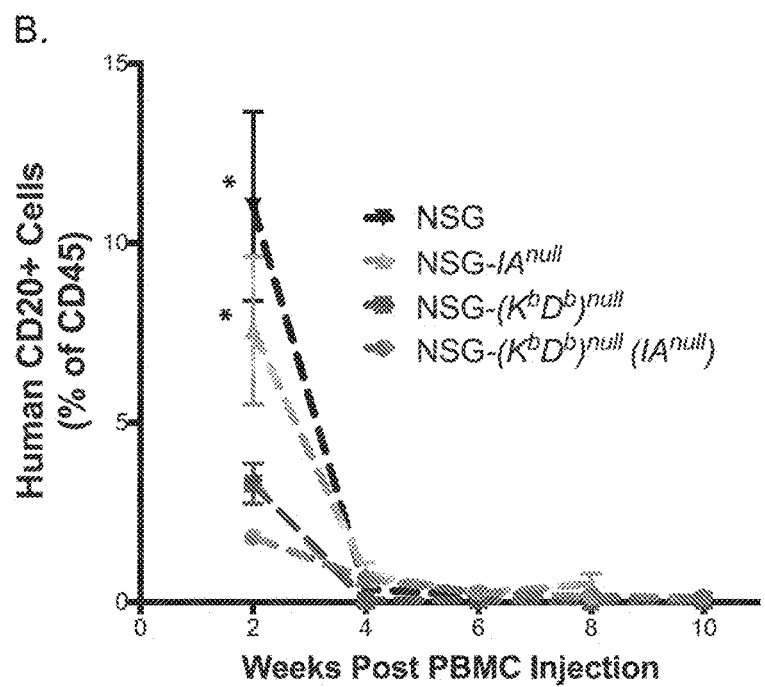

Engraftment of Human T Cells and B Cells in PBMC-Engrafted NSG, NSG-MHC Class I Knockout, NSG-MHC Class II Knockout, and NSG-MHC I/II Knockout Mice NSG-(K$^b$ D$^b$)$^{null}$ (IA$^{null}$):

Circulating human CD45+ cells were predominately CD3+ T cells in NSG, NSG-(IA$^{null}$), and NSG-(K$^b$ D$^b$)$^{null}$ mice (FIG. 5A). Similarly, the majority of CD45+ in cells NSG-(K$^b$ D$^b$)$^{null}$ (IA$^{null}$) were also CD3+ T cells. In the NSG and NSG-(IA$^{null}$) mice, there were readily detectable numbers of CD20+ B cells at two weeks post engraftment, but these were essentially undetectable by four weeks post engraftment (FIG. 5B).

Figure 5C:
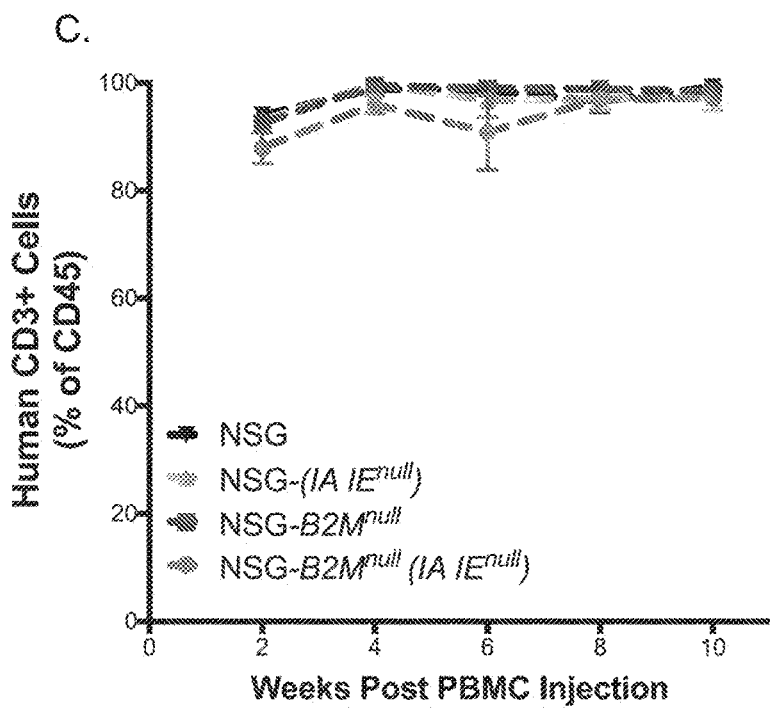
Figure 5D:
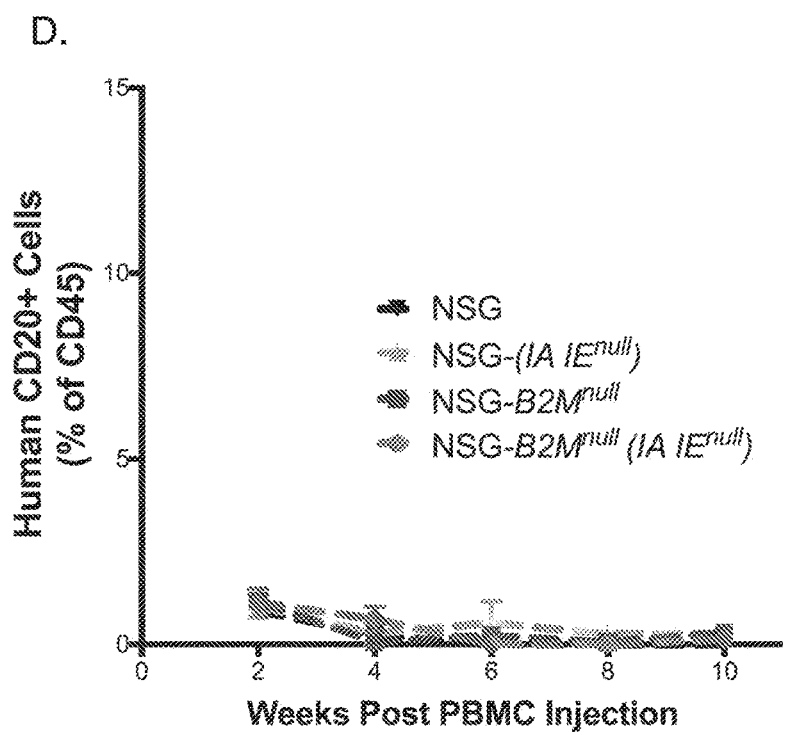

NSG-B2M$^{null}$ (IA IE)$^{null}$:

NSG-B2M$^{null}$ mice were used as an MHC class I knockout control for comparison. PBMC engraftment in NSG, NSG-(IA$^{null}$), and NSG-B2M$^{null}$ mice consisted of predominately CD3+ T cells as was observed in NSG-B2M$^{null}$ (IA IE)$^{null}$ mice (FIG. 5C). Although human CD20+ B cells were readily apparent in the NSG and NSG-IA$^{null}$ mice at two weeks in the first experiments, they were present at extremely low levels in all four strains examined (FIG. 5D), which likely reflects donor variability as we sometimes observe this in PBMC-engrafted NSG mice.

Figures 6A, 6B, 6C:
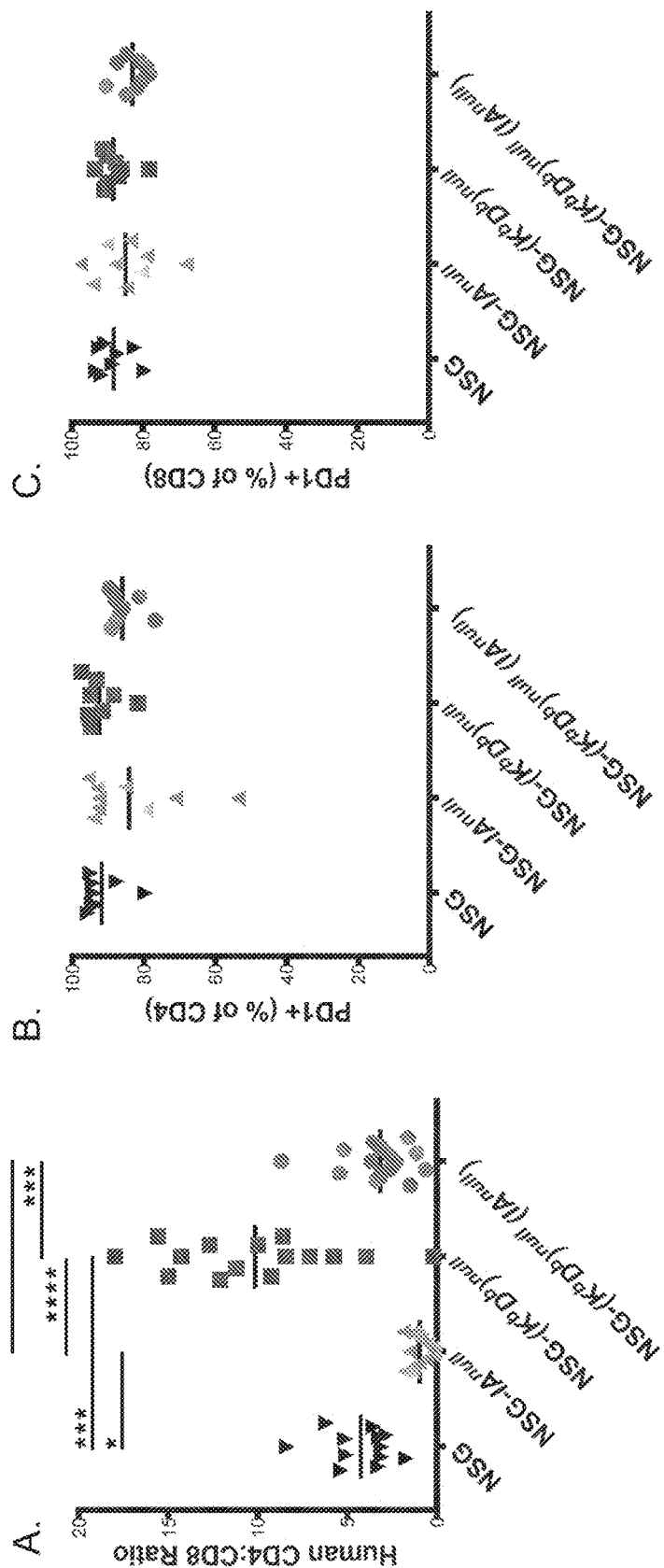
FIGS. 6A-6H show phenotypic analysis of human T cells engrafting in NSG, NSG-(IA$^{null}$), NSG-(K$^b$ D$^b$)$^{null}$, and NSG-(K$^b$ D$^b$)$^{null}$ (IA$^{null}$) mice injected with PBMC. Recipient mice were injected IV with 10×10$^6$ PBMC, and at 4 weeks post-injection mice were monitored for levels of human CD3+/CD4+ and CD3/CD8+ T cells (FIG. 6A and FIG. 6D) and T cell phenotype (FIG. 6B, FIG. 6C and FIG. 6E-FIG. 6H) in peripheral blood. The data are representative of 2 independent experiments. A one-way ANOVA was used to determine significant differences between groups. * represents p<0.05,  represents p<0.01, * represents p<0.005, and **** represents p<0.001.
Figures 6D, 6E, 6F:
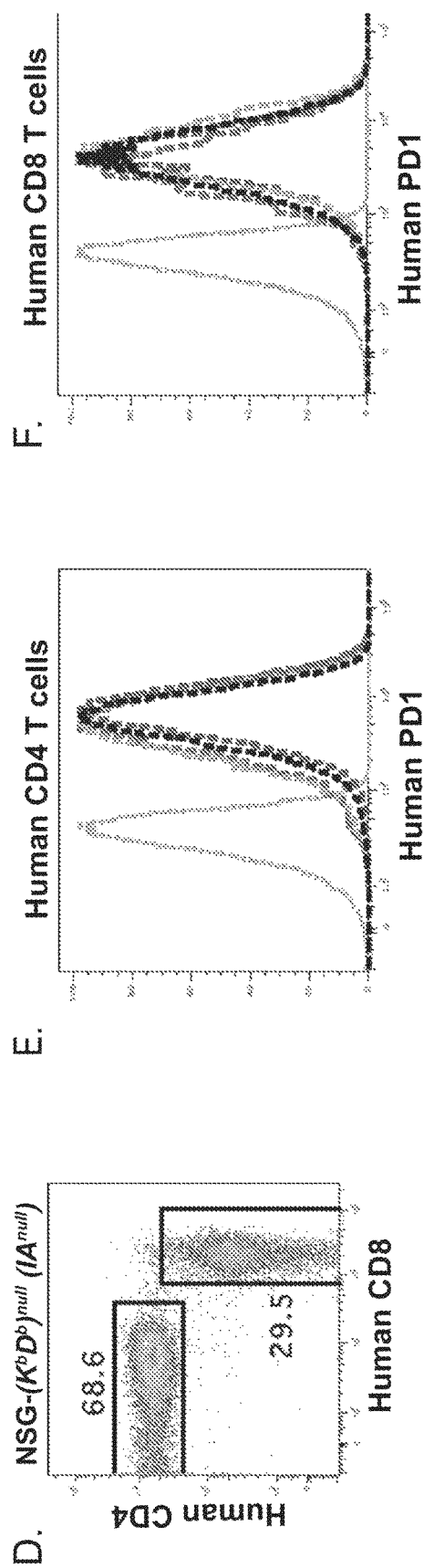
Figure 6G:
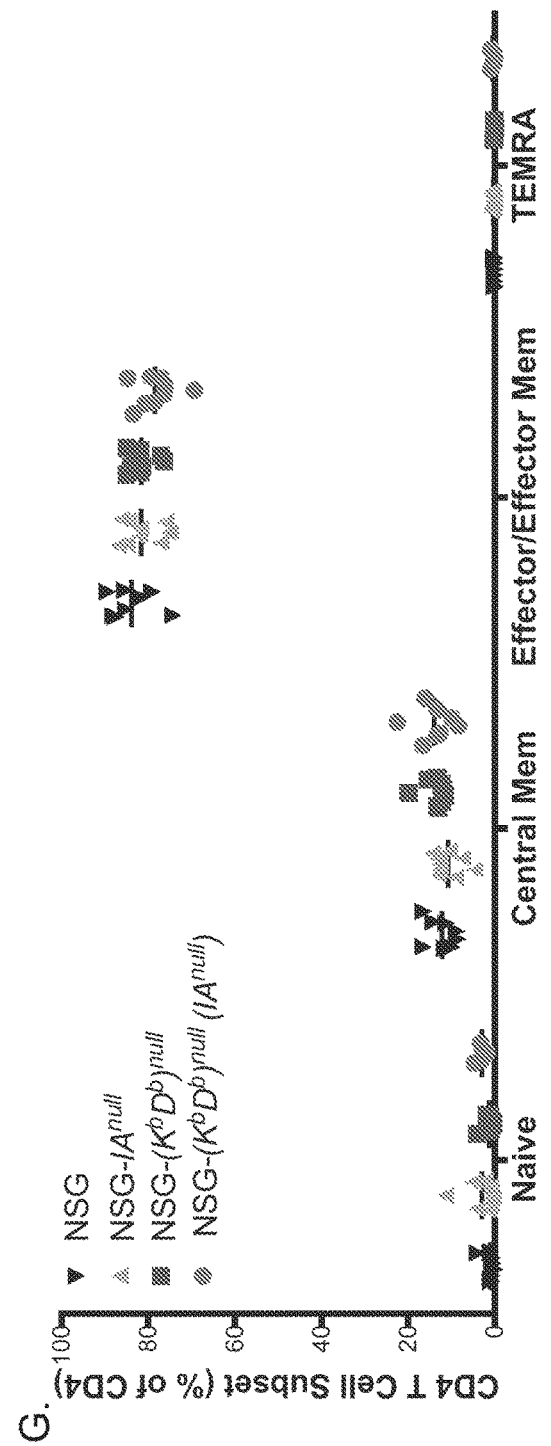
Figure 6H:
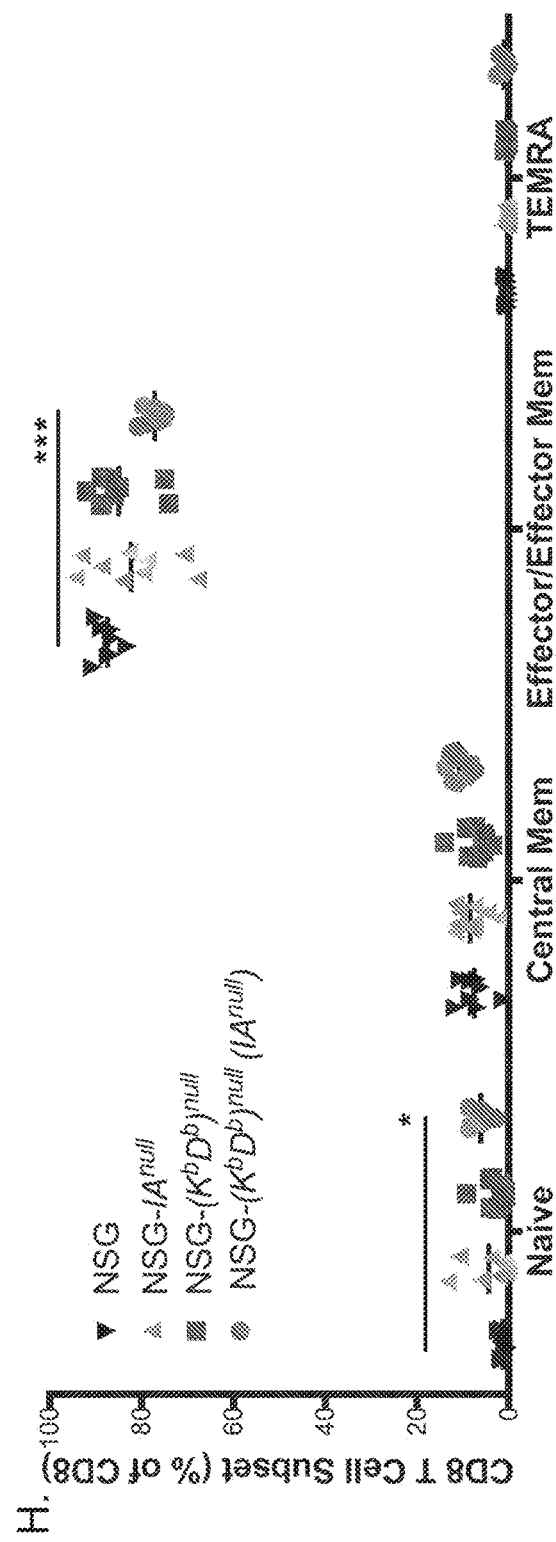

Phenotypic Analysis of Human T Cells Engrafted in NSG, NSG-(IA$^{null}$), NSG-(K$^b$ D$^b$)$^{null}$, and NSG-(K$^b$ D$^b$)$^{null}$ (IA$^{null}$) Mice Injected with PBMC The CD4:CD8 ratio in NSG mice at 4 weeks post PBMC-engraftment was approximately 4:1 (FIG. 6A). In contrast, very few CD4+ T cells engrafted in NSG-(IA$^{null}$) mice, while high levels of CD4+ T cells engrafted in NSG-(K$^b$ D$^b$)$^{null}$ mice, resulting in very low and high CD4:CD8 ratios, respectively. The CD4:CD8 ratio of CD3+ T cells in NSG-(K$^b$ D$^b$)$^{null}$ (IA$^{null}$) mice was similar to that observed in NSG mice (FIG. 6A), suggesting that neither human T cell subset had a selective advantage for engraftment in mice that lack both MHC class I and class II. The majority of CD4+ and CD8+ T cells in all four strains expressed the activation marker, PD-1 ((FIG. 6B, FIG. 6C). A representative histogram of CD4+ and CD8+ CD3+ T cells (FIG. 6D) and of PD-1 staining of CD4+ and CD8+ cells (FIG. 6E, FIG. 6F) is shown. To determine the activation state of the CD4+ and CD8+ T cells, each subset was stained for CD45RA and CCR7. CD45RA+CCR7+ cells are labeled as naïve T cells, CD45RA−CCR7+ cells are labeled as central memory T cells, CD45RA−CCR7− cells are labeled as T effector/effector memory T cells, and CD45RA+CCR7− cells are labeled as effector memory RA (TEMRA) T cells. In both the CD4+ (FIG. 6G) and CD8+ T cell populations (FIG. 6H), very few naïve T cells were observed in the blood at 4 weeks post PBMC injection. A few central memory CD4+ and CD8+ T cells were detected, while almost no TEMRA CD4+ or CD8+ T cells were present. The majority of CD4+ and CD8+ T cells were effector/memory CD45RA−CCR7− T cells (FIG. 6G, FIG. 6H).

Figures 7A, 7B, 7C:
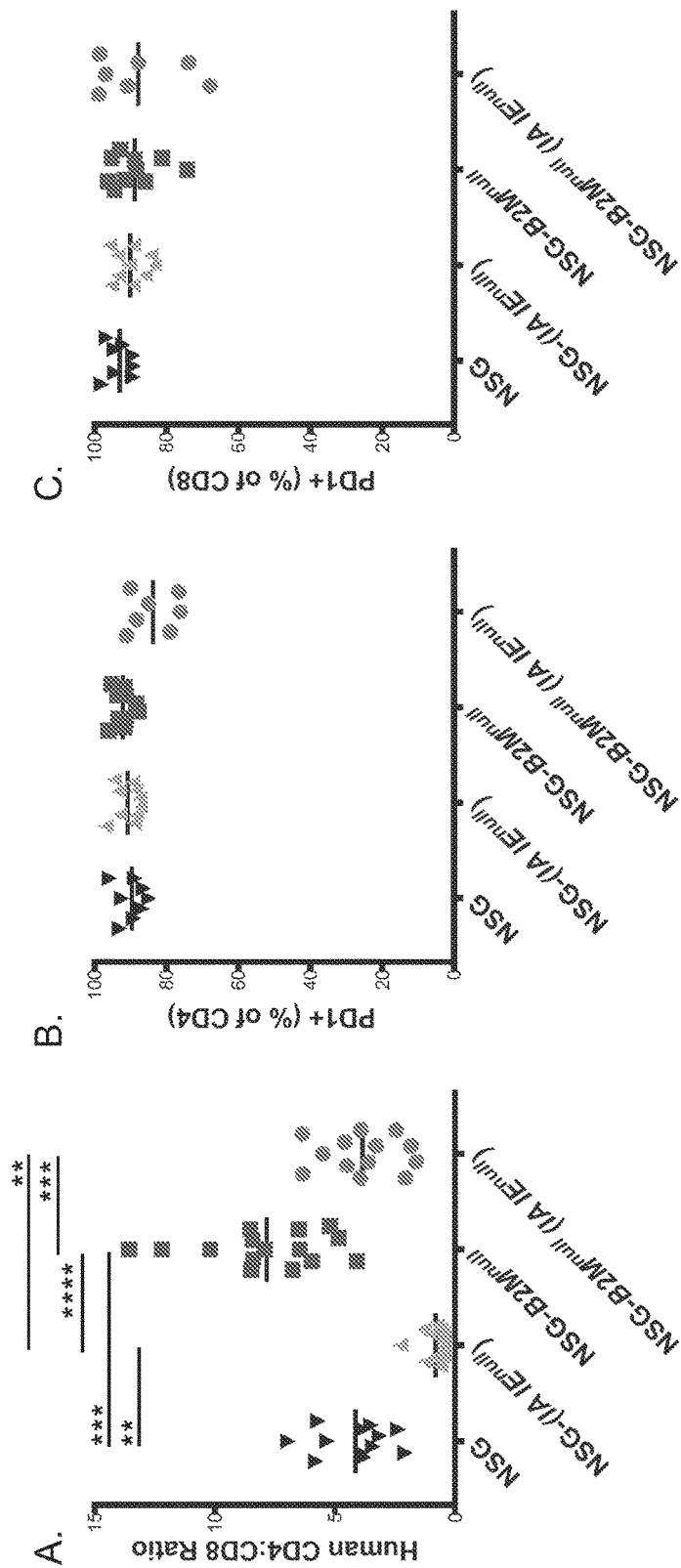
FIGS. 7A-7H show phenotypic analysis of human T cells engrafting in NSG, NSG-(IA IE)$^{null}$, NSG-B2M$^{null}$, and NSG-B2M$^{null}$ (IA IE)$^{null}$ mice injected with PBMC. Recipient mice were injected IV with 10×10$^6$ PBMC, and at 4 weeks post-injection mice were monitored for levels of human CD3+/CD4+ and CD3/CD8+ T cells (FIG. 7A and FIG. 7D) and T cell phenotype (FIG. 7B, FIG. 7C and FIG. 7E-FIG. 7H) in peripheral blood. The data are representative of 2 independent experiments. A one-way ANOVA was used to determine significant differences between groups. * represents p<0.05,  represents p<0.01, * represents p<0.005, and **** represents p<0.001.
Figure 7F:
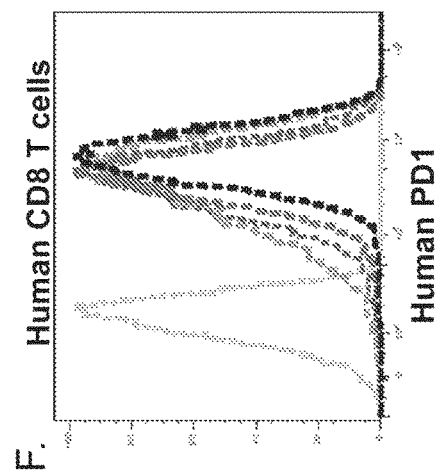
Figure 7E:
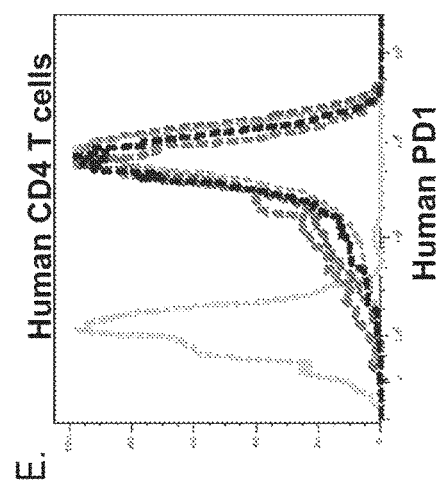
Figure 7D:
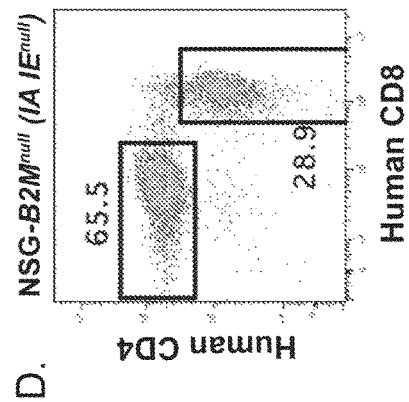
Figure 7G:
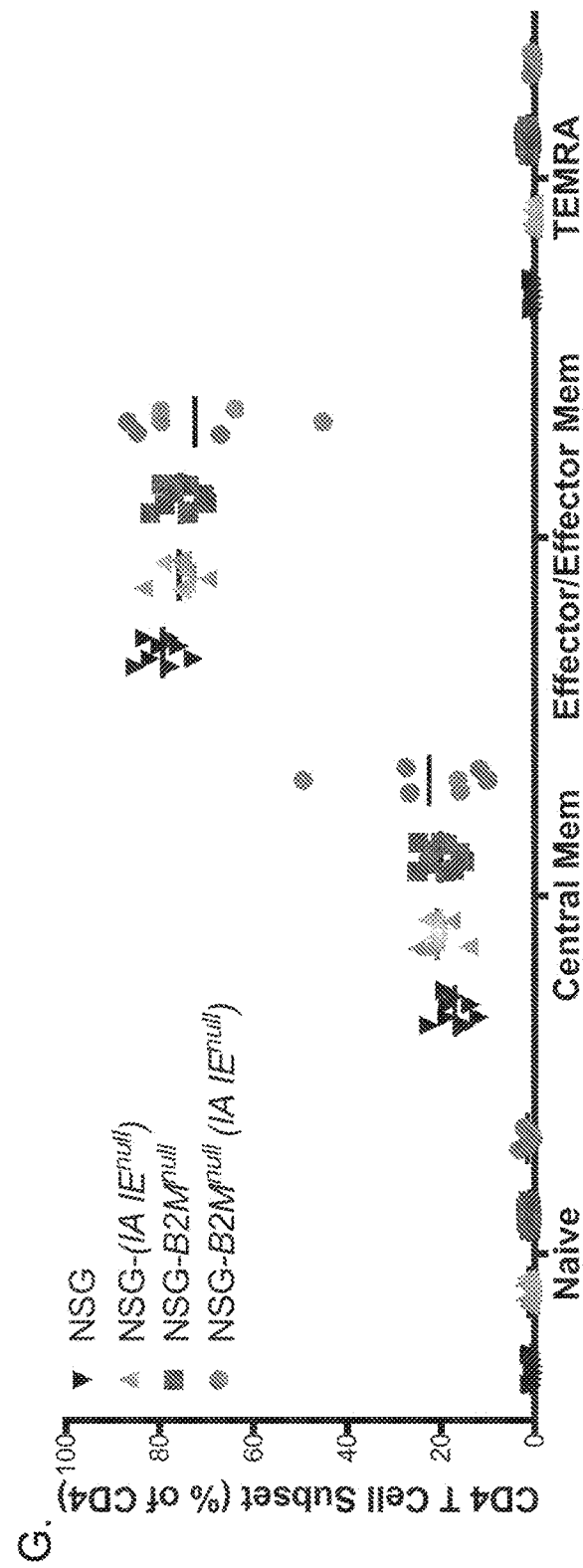
Figure 7H:
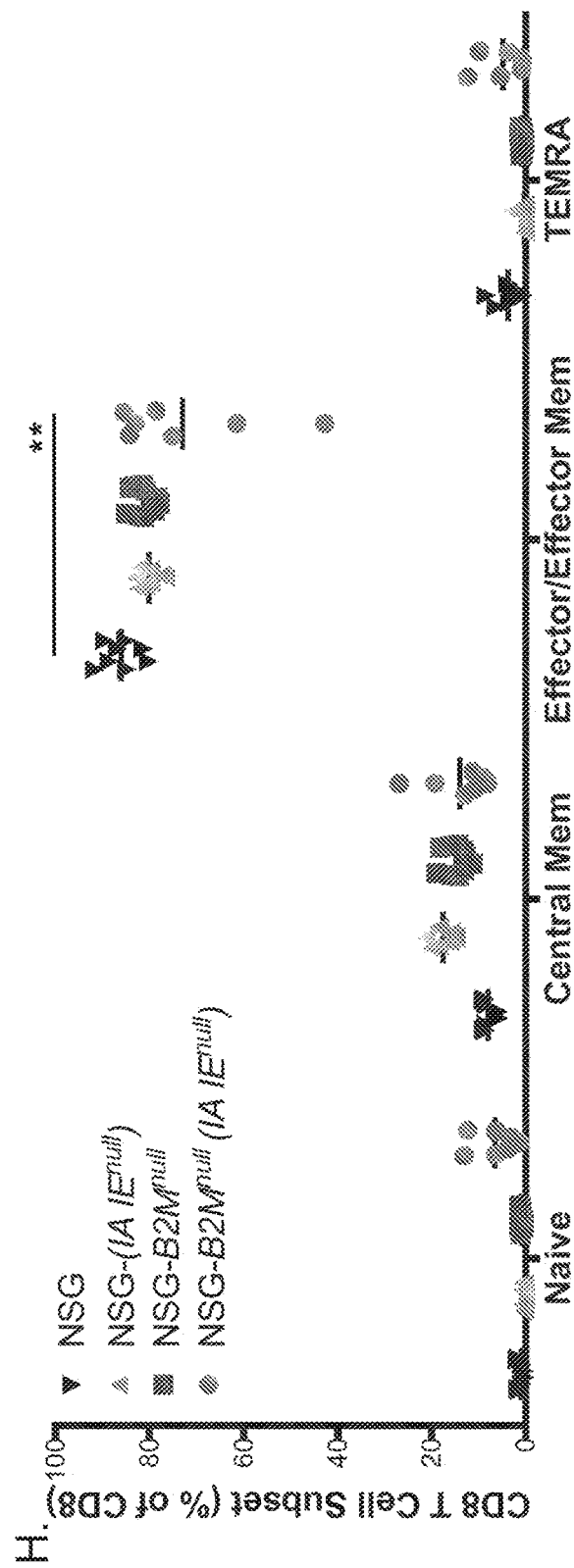

Phenotypic Analysis of Human T Cells Engrafting in NSG, NSG-(IA IE)$^{null}$, NSG-B2M$^{null}$, NSG-B2M$^{null}$ (IA IE)$^{null}$, and NSG-B2M$^{null}$(IA IE)$^{null}$ Mice Injected with PBMC The CD4:CD8 T cell ratios in NSG mice were again approximately 4:1 (FIG. 7A). MHC class II (IA IE)$^{null}$ and class I KO B2M$^{null}$ mice similarly had CD4:CD8 low and high T cell ratios, respectively, as observed in the NSG-(IA$^{null}$) and NSG-(K$^b$ D$^b$)$^{null}$ mice (FIG. 6A). NSG-B2M$^{null}$ (IA IE)$^{null}$ mice (FIG. 7A) showed the 3:1 CD4:CD8 ratio of ~3:1 observed in NSG and in NSG-B2M$^{null}$ (IA IE)$^{null}$ mice (FIG. 6A). The majority of CD4 (FIG. 7B) and CD8 (FIG. 7C) cells in all four strains of MHC KO mice expressed the activation marker PD-1. Representative histograms of CD4 and CD8 staining (FIG. 7D) and of CD4 (FIG. 7E) and CD8 (FIG. 7F) staining with anti-PD-1 are shown. In all four strains, there were few CD4 (FIG. 7G) or CD8 (FIG. 7I) naïve or TEMRA cells observed while some central memory cells were present. The majority of T cells were in the CD45−CCR7+ effector/effector memory subset (FIG. 7G, FIG. 7H).

Figures 8A, 8B:
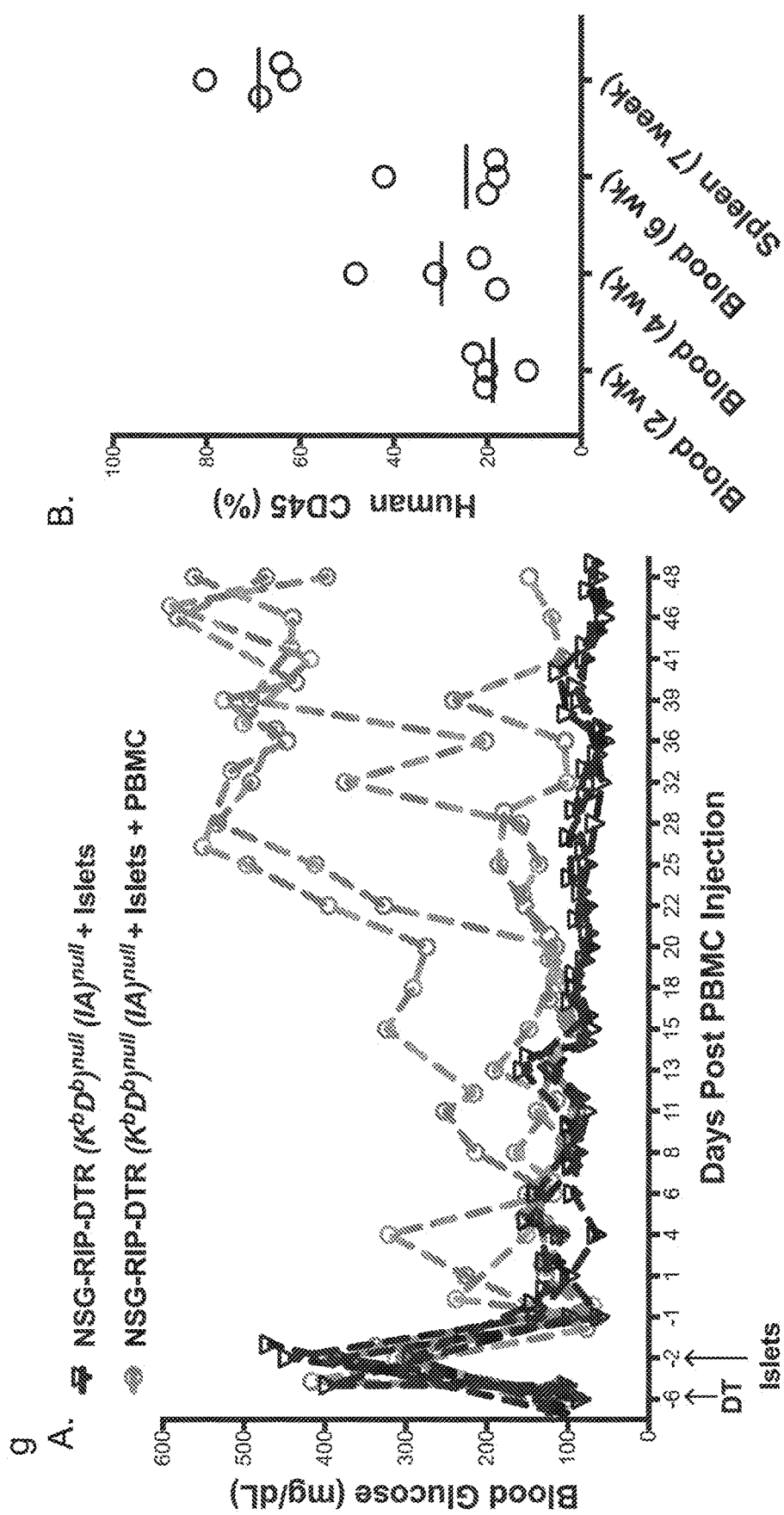
FIGS. 8A-8F show rejection of human islet allografts in PBMC-engrafted NSG-RIP-DTR (K$^b$ D$^b$)$^{null}$ (IA$^{null}$) mice. The data are representative of 2 independent experiments. A t-test was used to determine significant differences between groups. * represents p<0.05,  represents p<0.01, * represents p<0.005.

Engrafted Human T Cells in NSG-(K$^b$ D$^b$)$^{null}$ (IA$^{null}$) Mice are Functional Injection of human PBMC into NSG mice engrafted with human allogeneic islets leads to islet allograft rejection. To determine if the human immune cells engrafted in NSG MHC I/II knockout mice were functional, a new strain of mice, NSG-RIP-DTR (K$^b$D$^b$)$^{null}$ (IA$^{null}$), was created expressing the diphtheria toxin receptor under the control of the rat insulin promoter. Injection of diphtheria toxin (DT) into male mice expressing the diphtheria toxin receptor under the control of the rat insulin promoter leads to mouse beta cell death and hyperglycemia. The NSG-RIP-DTR (K$^b$ D$^b$)$^{null}$ (IA$^{null}$) strain permits the complete and specific ablation of mouse pancreatic beta cells, avoiding the broadly toxic effects of diabetogenic drugs such as streptozotocin. As shown in FIG. 8A, injection of NSG-RIP-DTR (K$^b$ D$^b$)$^{null}$ (IA$^{null}$) mice with DT led to the rapid development of diabetes. The NSG-RIP-DTR (K$^b$ D$^b$)$^{null}$ (IA$^{null}$) strain, was used to test the ability of human PBMC to reject islet allografts in hyperglycemic NSG MHC I/II knockout mice.

Intrasplenic transplantation of 4000 human IEQ restored normoglycemia in the mice within 1-2 days. These mice were then divided into two groups. One islet transplanted group was injected IP with 50×10$^6$ allogeneic PBMC whereas the other group received no PBMC to confirm the function of the human islets in the absence of an allogeneic immune system. Control mice that received only human islets remained normoglycemic through the experimental period (N=3). In contrast, 3 of 4 mice that received allogeneic human PBMC reverted to hyperglycemia after 3 to 4 weeks (FIG. 8A).

Figures 8C, 8D:
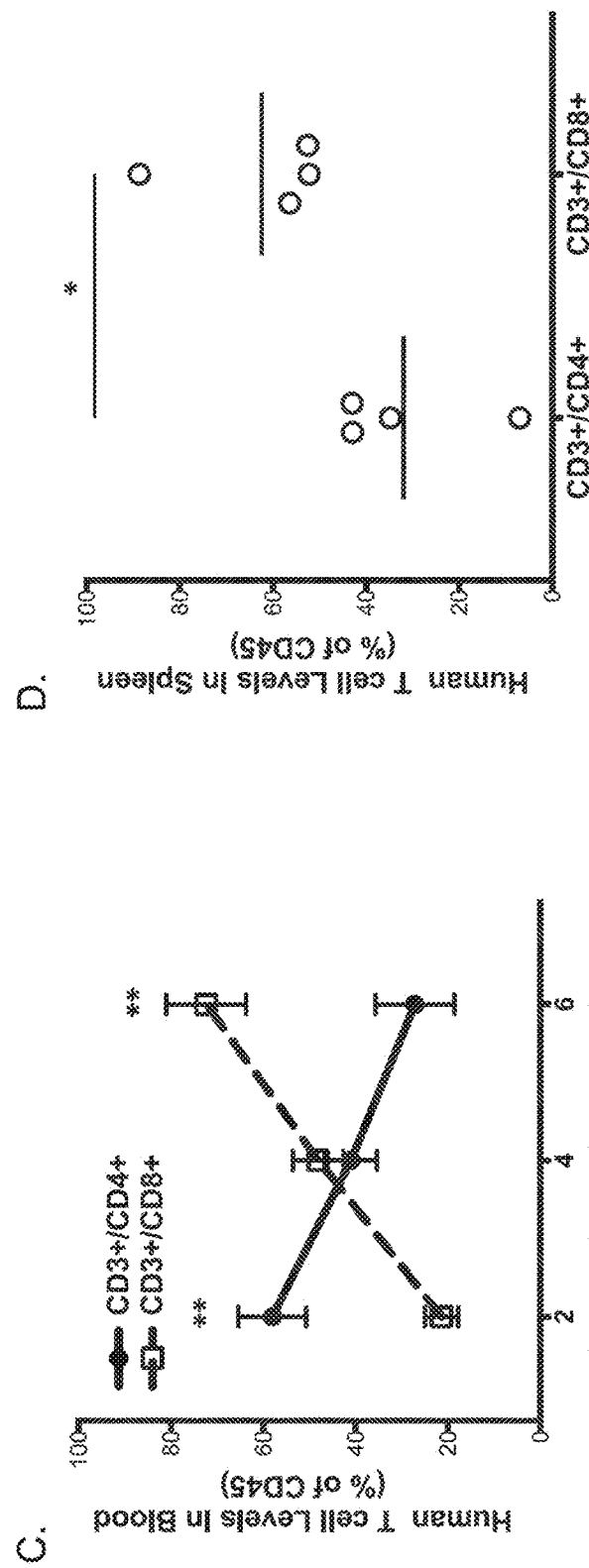
Figure 8F:
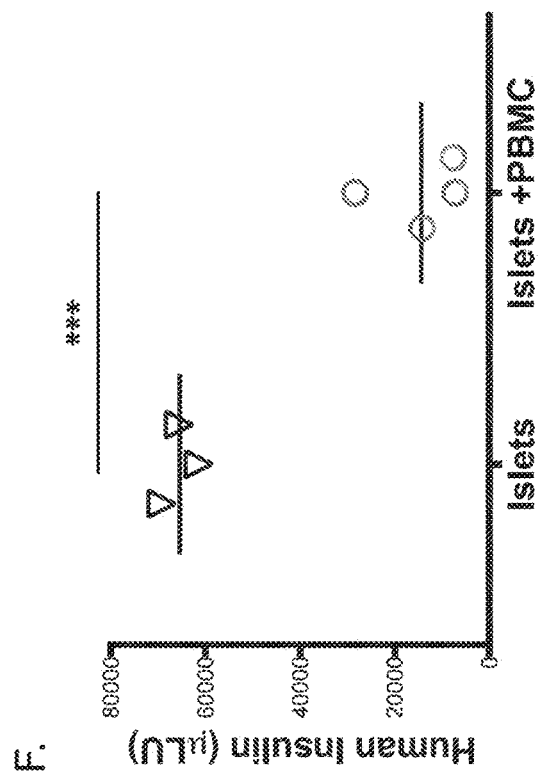
Figure 8E:
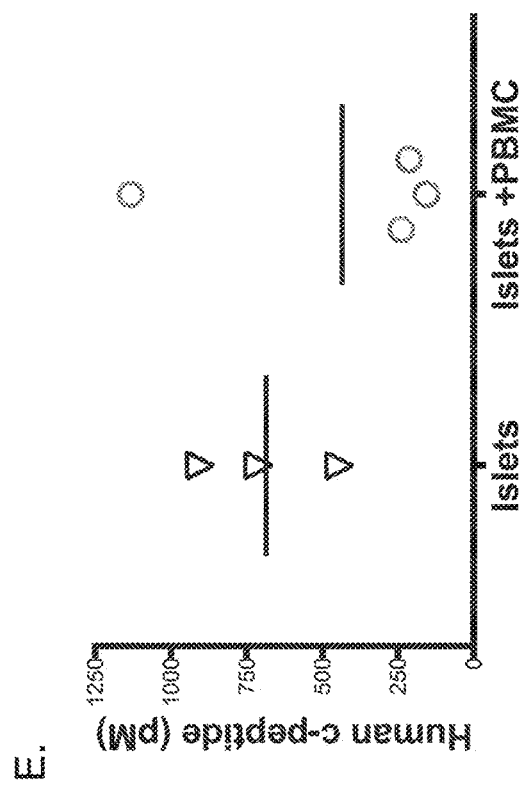

The engraftment levels of human CD45+ cells in PBMC injected islet-transplanted mice trended towards higher percentages in the blood over time, and there were up to ~70% human CD45+ cells in the spleen when analyzed at 7 weeks post PBMC injection. This level of human CD45+ cell engraftment in the NSG-RIP-DTR (K$^b$D$^b$)$^{null}$ (IA$^{null}$) strain was higher than that observed in PBMC-engrafted NSG-(K$^b$ D$^b$)$^{null}$ (IA$^{null}$) mice (FIG. 4B), although five-fold higher numbers of human PBMC (50×10$^6$) were injected in the NSG-RIP-DTR (K$^b$ D$^b$)$^{null}$ (IA$^{null}$) mice as compared to the 10×10$^6$ cells injected into NSG-(K$^b$ D$^b$)$^{null}$ (IA$^{null}$) mice. The CD4:CD8 cell ratio changed dramatically in the blood over the course the experiment as the percentages of CD4+ T cells dropped while the percentages of CD8+ T cells in the blood increased dramatically (FIG. 8C). At the termination of the experiment, the ratios of CD4:CD8 T cells in the spleen also showed a dramatic increase of CD8 T cells (FIG. 8D). The levels of human C-peptide in the blood at 6 weeks was decreased in 3 of 4 islet-engrafted mice that received human PBMCs; the one mouse that did not revert to hyperglycemia had levels of C-peptide similar to that observed in islet recipients that were not transplanted with allogeneic PBMCs (FIG. 8E). However, in all 4 mice that were given the allogeneic PBMCs, the quantity of human insulin observed in the islet grafts was significantly lower as compared islet transplant recipients that were not given human PBMCs (FIG. 8F).

Thus, human PBMC engrafted in the NSG-RIP-DTR (K$^b$ D$^b$)$^{null}$ (IA$^{null}$) mice readily engrafted into hyperglycemic NSG-RIP-DTR (K$^b$ D$^b$)$^{null}$ (IA$^{null}$) mice. The human islet allografts were rejected as evidenced by the return of hyperglycemia, which was confirmed histologically. This was also confirmed by the reduction of circulating C peptide and a decrease in the absolute amount of insulin remaining in the graft. The islet transplanted mice increased the proportion of CD8 T cells in both the blood and the spleen. This suggests that the presence of islet allografts preferentially stimulated and expanded the cytotoxic CD8 T cell population. These data document that human PBMC function can be evaluated in NSG MHC I/II knockout mice in the absence of an ongoing GVHD response.

Modulation of Engrafted Human T Cells by Treatment with AAV-IL2 in NSG and NSG-(K$^b$ D$^b$)$^{null}$ (IA$^{null}$) Mice Transplanted with PBMC Many of the drugs being advanced to the clinic are immune modulators, and one of these entering clinical trials is the administration of recombinant IL2. High dose IL2 has been used for cancer therapy whereas low doses of IL2 have been used to treat autoimmune diseases.

Figures 9A, 9B, 9C:
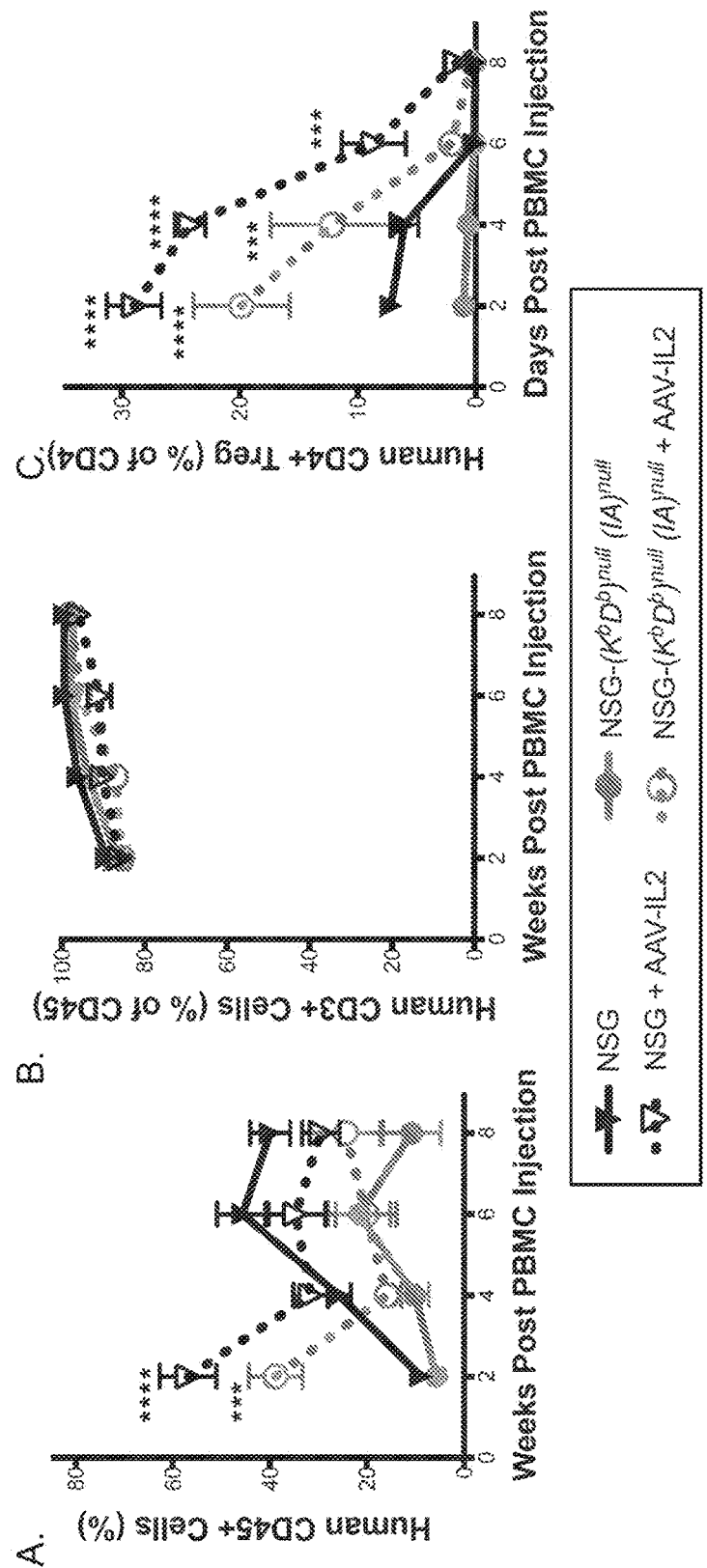
FIGS. 9A-9H show expression of human IL2 in PBMC engrafted NSG mice and NSG-(K$^b$ D$^b$)$^{null}$ (IA$^{null}$) mice enhances survival of human CD4+ Treg. Recipient NSG and NSG-(K$^b$ D$^b$)$^{null}$ (IA$^{null}$) mice were injected IP with 2.5× 10$^{11}$ particles of AAV-IL2 or injected with PBS. Two weeks later mice were injected intraperitoneally (IP) with 1×10$^6$ PBMC.
Figures 9D, 9E:
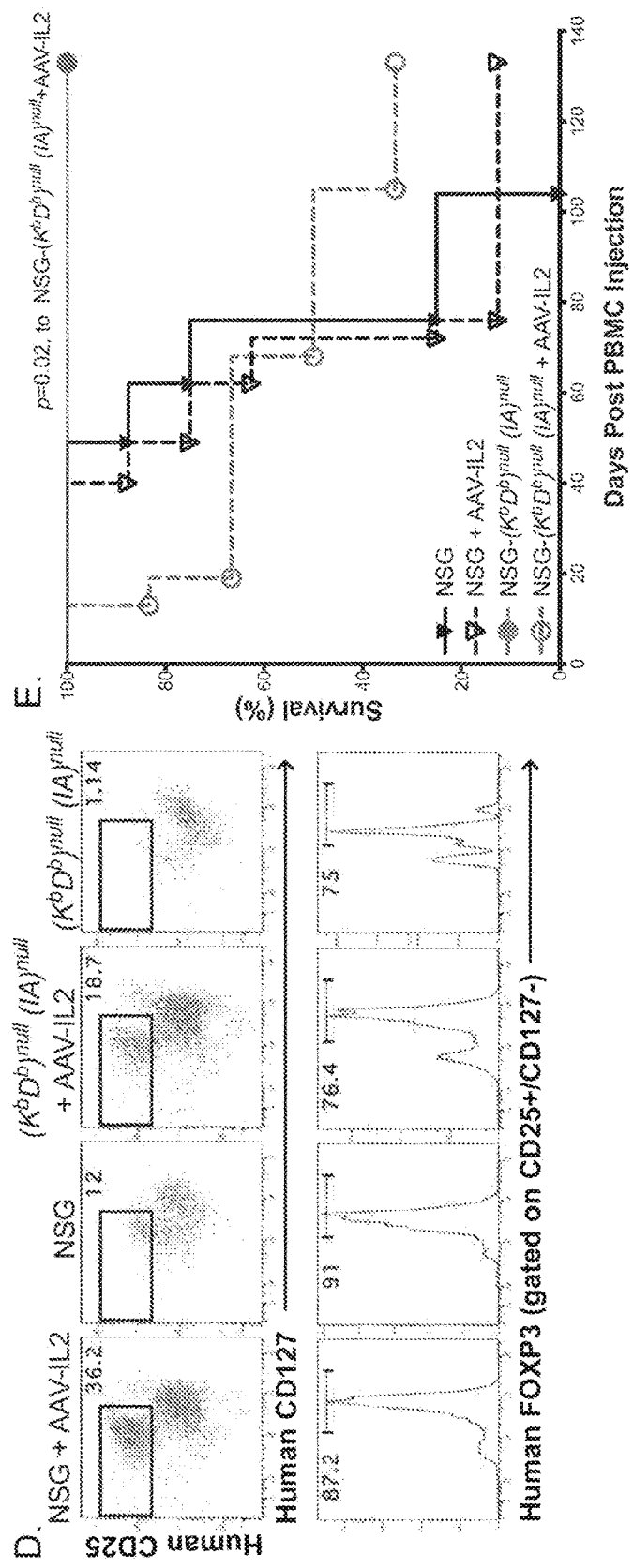

Having shown that the engrafted human T cells in the NSG-(K$^b$ D$^b$)$^{null}$ (IA$^{null}$) mice are functional (FIG. 8A) but do not mediate acute GVHD (FIG. 3), it was next determined whether administration of human recombinant IL2 could modulate the T cell populations. Administration of human IL2 by injection of an AAV8-human IL2 expressing vector increased the proportion of human Tregs in NSG mice humanized by engraftment of human fetal liver and thymus, i.e., the BLT model. Injection of AAV-huIL2 led to a transient expansion of human CD45+ cells in the blood of NSG and NSG-(K$^b$ D$^b$)$^{null}$ (IA$^{null}$) mice that had been engrafted with 10×10$^6$ PBMC for 2 weeks (FIG. 9A). AAV-IL2 did not alter the proportion of human CD45+ cells that were CD3+ over the 8 week course of the experiment (FIG. 9B). However, there was a significant increase in the proportion of CD4+ cells that expressed a T regulatory (Treg) phenotype (CD4+CD25+CD127−FOXP3+) at 2, 4 and 6 weeks in NSG mice and at 2 and 4 weeks in NSG-(K$^b$ D$^b$)$^{null}$ (IA$^{null}$) mice post PBMC injection (FIG. 9C). Representative staining of CD4+ T cells with antibodies to CD25 and CD127 is shown in the upper row and the expression of FOXP3 in the putative CD4+CD25+CD127− T cells in NSG and NSG-(K$^b$ D$^b$)$^{null}$ (IA$^{null}$) mice with or without administration of AAVIL2 is shown in the lower row (FIG. 9D). The relative percentage of Treg cells declined steadily from 2 weeks through 8 weeks and was at normal levels of CD4+ T cells by 8 weeks post PBMC engraftment in both strains. Using the AAV-IL2 vector given to NSG and NSG-($K^b$ $D^b$)$^{null}$ (IA$^{null}$) mice, the levels of IL2 decreased each week from week 2 (219±48 and 262±40 pg/ml), respectively to week 4 (159±59 and 214±62 pg/ml), respectively to week 6 (110±53 and 130±72 pg/ml; N=8 at weeks 2, 4, and 6 for NSG and 5 for NSG-($K^b$ $D^b$)$^{null}$ (IA$^{null}$) mice at 2 weeks and 4 mice at 4 and 6 weeks). This decrease in circulating IL2 correlates with the loss of Tregs in the present experiment.

Figures 9F, 9G, 9H:
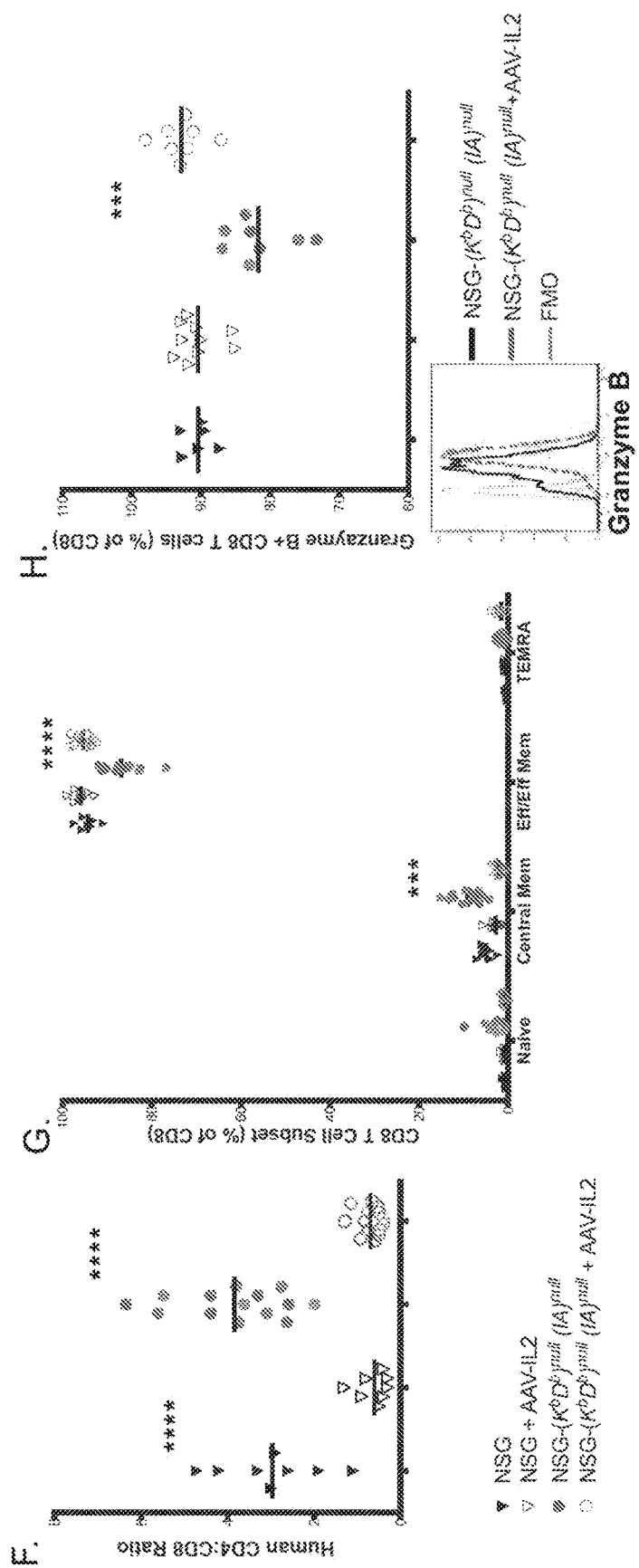

However, the administration of AAV-IL2 also shortened the survival of NSG-($K^b$ $D^b$)$^{null}$ (IA$^{null}$) mice to that observed in NSG and NSG mice treated with AAV-IL2 (FIG. 9E). The injection of AAV-IL2 also altered the CD4:CD8 ratio to that of predominately CD8 T cells in both NSG and NSG-($K^b$ $D^b$)$^{null}$ (IA$^{null}$) mice as compared to those not injected with AAV-IL2 (FIG. 9F). The proportions of CD4 and CD8 naïve, central memory, effector/effector memory and TEMRA subsets in the CD4+ T cell population were not different in the blood of NSG and NSG-($K^b$ $D^b$)$^{null}$ (IA$^{null}$) mice with or without AAV-IL2 treatment. The only difference in the proportions of T cell subset in the CD8 T cell population was in the effector/effector memory T cell subset which was increased in mice treated with AAV-IL2 (FIG. 9G). Correlating with the increase in CD8+ effector/effector memory T cells in AAV-IL2 treated NSG-($K^b$ $D^b$)$^{null}$ (IA$^{null}$) mice was an increase in the percentage of CD8 T cells that expressed granzyme B (FIG. 9H).

Co-Administration of PBMC and Human Patient-Derived Tumor Cells

NSG and NSG-$K^b$ $D^b$)$^{null}$ (IA$^{null}$) mice were implanted SQ with PDX colon tumors (2 mm$^3$) and 10 days later injected IP with 20×10$^6$ PBMC from an non-matched donor. Mice were monitored for survival and for tumor growth.

Figure 10A:
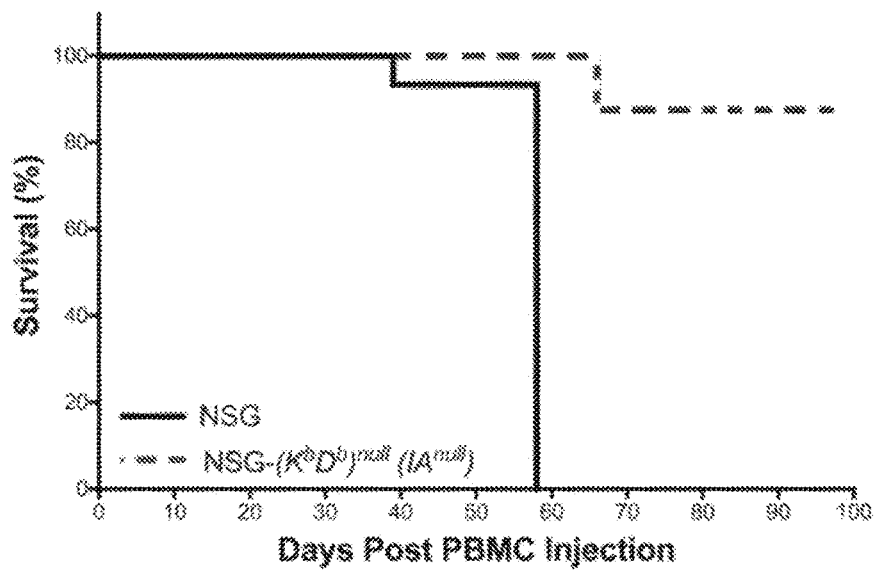
FIG. 10A is a graph showing percent survival of a group of NSG mice co-injected with PBMC and human patient-derived tumor cells and a group of NSG-$(K^b D^b)^{null}$ $(IA^{null})$ mice co-injected with PBMC and human patient-derived tumor cells.

FIG. 10A is a graph showing percent survival of a group of NSG mice co-injected with PBMC and human patient-derived tumor cells and a group of NSG-($K^b$ $D^b$)$^{null}$ (IA$^{null}$) mice co-injected with PBMC and human patient-derived tumor cells.

Figure 10B:
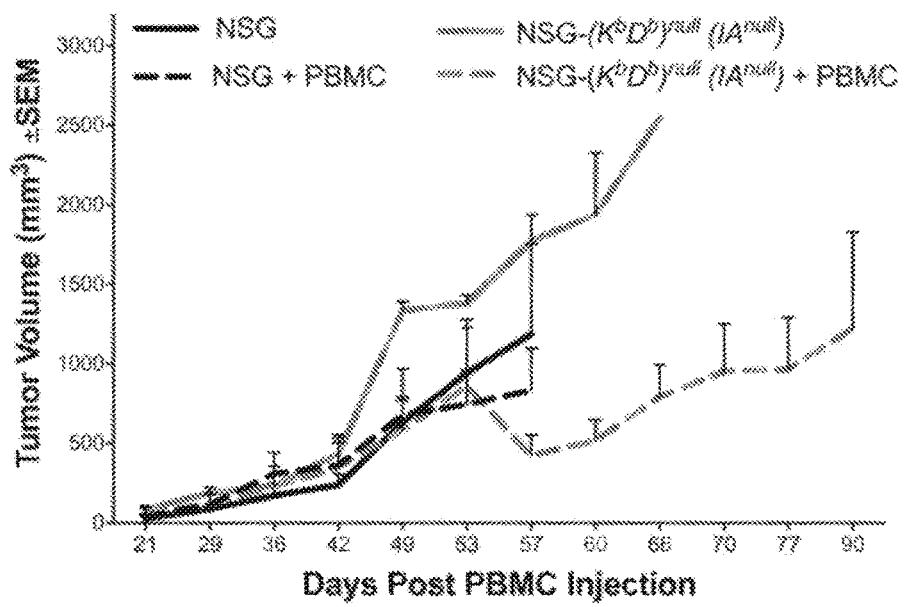
FIG. 10B is a graph showing tumor growth in 1) NSG mice injected with human patient-derived tumor cells; 2) NSG mice co-injected with PBMC and human patient-derived tumor cells; NSG-$(K^b D^b)^{null}$ $(IA^{null})$ mice injected with PBMC; and NSG-$(K^b D^b)^{null}$ $(IA^{null})$ mice co-injected with PBMC and human patient-derived tumor cells.

FIG. 10B is a graph showing tumor growth in 1) NSG mice injected with human patient-derived tumor cells; 2) NSG mice co-injected with PBMC and human patient-derived tumor cells; NSG-($K^b$ $D^b$)$^{null}$ (IA$^{null}$) mice injected with PBMC; and NSG-($K^b$ $D^b$)$^{null}$ (IA$^{null}$) mice co-injected with PBMC and human patient-derived tumor cells. Thus, NSG-($K^b$ $D^b$)$^{null}$ (IA$^{null}$) mice support co-engraftment of PDX tumor and PBMC.

Using two different NSG MHC class I/II knockout mouse models, the NSG-($K^b$ $D^b$)$^{null}$ (IA$^{null}$) strain and the NSG-B2M$^{null}$ (IA IE$^{null}$) strain, these examples demonstrate that the human PBMC engrafted but the mice did not develop an acute GVHD-like disease through the end of the experimental period, in some cases over 125 days after PBMC engraftment. These engrafted human T cells were functional as shown by their ability to reject human islet allografts. Moreover, the human T cells could be modulated in vivo as evidenced by providing recombinant human IL2 using AAV vectors leading to human T cell expansion. In the NSG-($K^b$ $D^b$)$^{null}$ (IA$^{null}$) strain, human IgG clearance was comparable to observed in NSG mice whereas IgG clearance in the NSG-B2M$^{null}$ (IA IE$^{null}$) strain was extremely rapid.

Any patents or publications mentioned in this specification are incorporated herein by reference to the same extent as if each individual publication is specifically and individually indicated to be incorporated by reference.

The compositions and methods described herein are presently representative of preferred embodiments, exemplary, and not intended as limitations on the scope of the invention. Changes therein and other uses will occur to those skilled in the art. Such changes and other uses can be made without departing from the scope of the invention as set forth in the claims.

The invention claimed is:

1. An immunodeficient non-obese diabetic mouse whose genome comprises: (a) a homozygous scid mutation in the endogenous Prkdc gene; (b) a homozygous null mutation in the endogenous Il2rg gene; (c) a homozygous null mutation in the endogenous H2-K1 gene; (d) a homozygous null mutation in the endogenous H2-D1 gene; and (e) a homozygous null mutation in the endogenous H2-Ab1 gene; wherein the genotype of the mouse is NOD.Cg-Prkdc$^{scid}$ H2-K1$^{tm1Bpe}$ H2-Ab1$^{em1Mvw}$ H2-D1$^{tm1Bpe}$ Il2rg$^{tm1Wjl}$/SzJ, and the mouse lacks functional major histocompatibility complex (MHC) I, lacks functional MHC II, and has a human immunoglobulin G (IgG) clearance rate of no more than 60% two days after administration of human IgG to the mouse.

2. The mouse of claim 1, further comprising human immune cells.

3. The mouse of claim 2, wherein the human immune cells are human peripheral blood mononuclear cells (PBMCs).

4. The mouse of claim 2, wherein the human immune cells are human T cells.

5. The mouse of claim 1, further comprising human tumor cells.

6. A method for testing an effect of a test substance on human immune cells in the mouse of claim 2, comprising:
 administering a test substance to the mouse of claim 5; and
 assaying the effect of the test substance on the human immune cells in the mouse, wherein the human immune cells are selected from the group consisting of human T cells and human PBMCs.

7. The method of claim 6 wherein the test substance is an anti-cancer agent.

8. The method of claim 6, wherein the test substance is an immunotherapeutic agent.

9. The method of claim 6, wherein the test substance is an anti-cancer immunotherapeutic agent.

10. The method of claim 6, wherein the test substance is an immune checkpoint inhibitor.

11. The method of claim 10, wherein the immune checkpoint inhibitor is a PD-1 inhibitor, PD-L1 inhibitor, or CTLA-4 inhibitor.

12. The method of claim 10, wherein the immune checkpoint inhibitor is atezolizumab, avelumab, durvalumab, ipilimumab, nivolumab, pembrolizumab, or an antigen-binding fragment of any one of the foregoing.

* * * * *

UNITED STATES PATENT AND TRADEMARK OFFICE
CERTIFICATE OF CORRECTION

PATENT NO. : 11,778,994 B2
APPLICATION NO. : 16/612450
DATED : October 10, 2023
INVENTOR(S) : Michael A. Brehm et al.

Page 1 of 1

It is certified that error appears in the above-identified patent and that said Letters Patent is hereby corrected as shown below:

In the Specification

At Column 1, Lines 6-9, REFERENCE TO RELATED APPLICATIONS section should read:
This application is a national stage filing under 35 U.S.C. § 371 of international application number PCT/US2018/032548, filed May 14, 2018, which was published under PCT Article 21(2) in English and claims priority from U.S. Provisional Patent Application Serial Nos. 62/505,264, filed May 12, 2017 and 62/649,099, filed March 28, 2018, the entire content of each of which is incorporated herein by reference.

At Column 1, Lines 13-15, GOVERNMENT SUPPORT section should read:
This invention was made with government support under Grant No. OD018259 and Grant No. OD011190, both awarded by the National Institutes of Health. The Government has certain rights in the application.

Signed and Sealed this
Thirty-first Day of December, 2024

Derrick Brent
*Acting Director of the United States Patent and Trademark Office*